(12) United States Patent
Bebbington et al.

(10) Patent No.: US 6,897,034 B2
(45) Date of Patent: May 24, 2005

(54) CD10-ACTIVATED PRODRUG COMPOUNDS

(75) Inventors: Christopher R. Bebbington, San Mateo, CA (US); Matthew H. Nieder, Seattle, WA (US); Pina M. Cardarelli, San Carlos, CA (US); Sanjeev Gangwar, San Mateo, CA (US); Lesley B. Pickford, Menlo Park, CA (US); Chin Pan, Los Altos, CA (US)

(73) Assignee: Medarex, Inc., Princeton, NJ (US)

( * ) Notice: Subject to any disclaimer, the term of this patent is extended or adjusted under 35 U.S.C. 154(b) by 117 days.

(21) Appl. No.: 10/167,627

(22) Filed: Jun. 11, 2002

(65) Prior Publication Data

US 2004/0087497 A1 May 6, 2004

Related U.S. Application Data

(60) Provisional application No. 60/297,596, filed on Jun. 11, 2001.

(51) Int. Cl.[7] .............................. C07K 1/113; C12Q 1/37
(52) U.S. Cl. ......................................... 435/24; 530/345
(58) Field of Search ................................. 530/329, 330, 530/331, 344, 345; 514/17, 18; 435/24

(56) References Cited

U.S. PATENT DOCUMENTS

| 5,599,686 A | 2/1997 | DeFeo-Jones et al. ........ 435/23 |
| 5,962,216 A | 10/1999 | Trouet et al. ................... 435/4 |
| 2002/0103133 A1 | 8/2002 | Copeland et al. ............. 514/16 |

FOREIGN PATENT DOCUMENTS

| WO | WO 96/05863 A1 | 2/1996 |
| WO | WO 98/52966 A1 | 11/1998 |
| WO | WO 00/33888 A2 | 6/2000 |
| WO | WO 00/69472 A3 | 11/2000 |

OTHER PUBLICATIONS

DATABASE: GenBank, Acc. No. Y00811, Sep. 12, 1993.
Baraniuk JN, et al., "Identification of neutral endopeptidase mRNA in human nasal mucosa." J Appl Physiol. Jan 1993;74(1):272–9.
Barker PE, et al., "The common acute lymphoblastic leukemia antigen gene maps to chromosomal region 3 (q21–q27)." J Immunol. Jan. 1, 1989;142(1):283–7.
Bateman RC Jr, et al., "Identification of the active–site arginine in rat neutral endopeptidase 24.11 (enkephalinase) as arginine 102 and analysis of a glutamine 102 mutant." J Biol Chem. Apr. 15, 1989;264(11):6151–7.
Bricout H, et al., "Synthetic and Kinetic Aspects of Nickel–Catalysed Amination of Allylic Alcohol Derivatives," Tet. Lett., 54:1073 (1998).
Casey ML, et al., "Progesterone–regulated cyclic modulation of membrane metalloendopeptidase (enkephalinase) in human endometrium." J Biol Chem. Dec. 5, 1991;266(34):23041–7.

Casimir Jr, et al., "First Application of the Dakin–West Reaction to Fmoc Chemistry: Synthesis of the ketomethylene tripeptide Fmox–Nα–Asp(tBu)–(R,S)Tyr(tBu) ψ(CO–CH2)Gly–OH," Tet. Lett. 36(27):4797–4800 (1995).
Chaires JB, et al., "Self–association of daunomycin." Biochemistry. Aug. 17, 1982;21(17):3927–32.
Chu P, and Arber DA. "Paraffin–section detection of CD10 in 505 nonhematopoietic neoplasms. Frequent expression in renal cell carcinoma and endometrial stromal sarcoma." Am J Clin Pathol. Mar. 2000;113(3):374–82.
Connelly JC, et al., "Neutral endopeptidase 24.11 in human neutrophils: cleavage of chemotactic peptide." Proc Natl Acad Sci U S A Dec. 1985;82(24):8737–41.
Devault A, et al. "Amino acid sequence of rabbit kidney neutral endopeptidase 24.11 (enkephalinase) deduced from a complementary DNA." EMBO J. May 1987;6(5):1317–22. Erratum in: EMBO J Aug. 1987;6(8):2506.
Genet J–P, et al., "Practical Palladium–Mediated Deprotective Method of Allyloxycarbonly in Aqueous Media," Tetrahedron, 50(2):497–503 (1994).
Genet J–P, et al., "A General and Simple Removal of the Allyloxycarbonyl Protecting Group by Palladium–Catalyzed Reactions Using Nitrogen and Sulfur Necleophiles," Synlett, 680–682 (1993).
Greaves MF, et al., "Selective expression of the common acute lymphoblastic leukemia (gp 100) antigen on immature lymphoid cells and their malignant counterparts." Blood. Apr. 1983;61(4):628–39.
Hayakawa E, et al., "Viscosity Study on the Self–Association of Doxorubicin in Aqueous Solution," Chem. Pharm. Bull., 39:1282–6 (1991).
Head JR, et al., "Cellular localizaton of membrane metalloendopeptidase (enkephalinase) in human endometrium during the ovarian cycle." J Clin Endocrinol Metab. Mar. 1993;76(3):769–76.
Hersh LB, and Morihara K. "Comparison of the subsite specificity of the mammalian neutral endopeptidase 24.11 (enkephalinase) to the bacterial neutral endopeptidase thermolysin." J Biol Chem. May 15, 1986;261(14):6433–7.
Indig FE, et al., "Investigation of neutral endopeptidases (EC 3.4.24.11) and of neutral proteinases (EC 3.4.24.4) using a new sensitive two–stage enzymatic reaction." FEBS Lett. Sep. 25, 1989;255(2):237–40. Erratum in: FEBS Lett Feb. 12, 1990;261(1):217.

(Continued)

*Primary Examiner*—Jeffrey Edwin Russel
(74) *Attorney, Agent, or Firm*—Lahive & Cockfield, LLP; Jane E. Remillard, Esq.; Cynthia M. Soroos, Esq.

(57) ABSTRACT

The compounds of the invention are modified forms of therapeutic agents. A typical prodrug compound of the invention comprises a therapeutic agent, an oligopeptide, a stabilizing group and, optionally, a linker group. The prodrug is cleavable by the CD10 enzyme. Methods of treatment using the prodrug and methods of designing a prodrug are also disclosed.

10 Claims, 38 Drawing Sheets

OTHER PUBLICATIONS

Kenny, A.J. et al., "Cell surface peptidases," in *Mammalian Ectoenzymes*, Kenny, A.J. et al. (eds). pp. 169–210 Elsevier, Amsterdam, New York, Oxford (1987).

Kenny, A.J., "Cell surface peptidases are neither peptide–nor organ–specific," Trends Biochem. Sci. 11:40–42 (1986).

Krongrad A, et al., "Endopeptidase 24.11 activity in the human prostate cancer cell lines LNCaP and PPC–1." Urol Res. 1997;25(2):113–6.

Letarte M, et al., "Common acute lymphocytic leukemia antigen is identical to neutral endopeptidase." J Exp Med. Oct. 1, 1988;168(4):1247–53.

Li C, and Hersh LB. "Neprilysin: assay methods, purification, and characterization." Methods Enzymol. 1995;248:253–63.

Liu AY. "Differential expression of cell surface molecules in prostate cancer cells." Cancer Res. Jul. 1, 2000;60(13):3429–34.

Malfroy B, et al., "High–affinity enkephalin–degrading peptidase in brain is increased after morphine." Nature. Nov. 30, 1978;276(5687):523–6.

Matsas R, et al., "The metabolism of neuropeptides. The hydrolysis of peptides, including enkephalins, tachykinins and their analogues, by endopeptidase–24.11." Biochem J. Oct. 15, 1984,223(2):433–40.

Matzanke BF, et al., "Evidence for polynuclear aggregates of ferric daunomycin. A Mossbauer, EPR, X–ray absorption spectroscopy and magnetic susceptibility study." Eur J Biochem. Jul. 15, 1992;207(2):747–55.

Pozsgay M, et al., "Substrate and Inhibitor studies of thermolysin–like neutral metalloendopeptidase from kidney membrane fractions. Comparison with bacterial thermolycin." Biochemistry. Mar. 25, 1986;25(6):1292–9.

Sales, N. et al., "Neutral endopeptidase 24.11 in rat peripheral tissues: comparative localization by 'ex vivo' and 'in vitro' autoradiography," Regul. Pept. 33:209 (1991).

Schmittberger T and Waldman H, "Synthesis of the Palmitoylated and Prenylated C–terminal Lipopeptides of the Human R– and N–Ras Proteins," Bioorg. Med. Chem., 7:749–762 (1999).

Shapiro G, and Buechler D., "Mild and Rapid Azide–Mediated, Palladium Catalyzed Cleavage of Allylester Based Protecting Groups," Tet. Lett., 35(30):5421–5424 (1994).

Suzuki T, et al., "Imbalance between neutral endopeptidase 24.11 and endothelin–1 expression in human endometrial carcinoma." Oncology. 2001;60(3):258–67.

Tabrizi–Fard, et al., "Evaluation of the Pharmacokinetic Properties of a Doxorubicin Prodrug in Female ICR (CDI® Mice following intravenous administration." Proc. American Association for Cancer Research, 42:324 (2001).

Turner, A.J., "Neprilysin" in Handbook of Proteolytic Enzymes, Barrett, A.J. et al, (eds.) Ch. 362, pp. 1080–1085 Academic Press (1998).

Van Der Vijgh WJ, et al., "Comparative metabolism and pharmacokinetics of doxorubicin and 4'–epidoxorubicin in plasma, heart and tumor of tumor–bearing mice." Cancer Chemother Pharmacol. 1990;26(1):9–12.

Waksman G, et al., "Binding of the bidentate inhibitor [3H]HACBO–Gly to the rat brain neutral endopeptidase "enkephalinase"." Biochem Biophys Res Commun. Aug. 30, 1985;131(1):262–8.

Weiss LM, et al., "Lymphobalstic lymphoma: an immunophenotype study of 26 cases with comparison to T cell acute lymphoblastic leukemia." Blood. Feb. 1986;67(2):474–8.

Wong–Leung YL, and Kenny AJ. "Some properties of a microsomal peptidase in rat kidney." Biochem J. Nov. 1968;110(2):5P.

Zajac JM, et al., "Enkephalin–degrading enzymes and angiotensin–converting enzyme in human and rat meninges." FEBS Lett. May 25, 1987;216(1):118–22.

| Symbol | Name | Structure |
|---|---|---|
| Aib | Aminoisobutyric Acid | H₂N COOH<br>H₃C CH₃ |
| Amb | 4-(Aminomethyl)benzoic Acid | H₂N—⟨benzene⟩—COOH |
| APP | 3-Amino-3-phenylpropionic Acid | Ph-CH(NH₂)-CH₂-COOH |
| Dg | Diglycolic Acid | HOOC-CH₂-O-CH₂-COOH |
| Gl | Glutaric Acid | HOOC-(CH₂)₃-COOH |

FIG. 1A

| Symbol | Name | Structure |
|---|---|---|
| Mal | Maleic Acid | 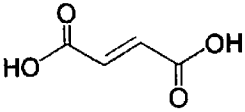 |
| NAA | 3-Amino-4,4-diphenylbutyric Acid | 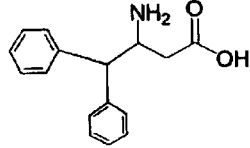 |
| Nal | 2-Naphthylalanine | 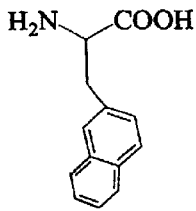 |
| Naph | 1,8-Naphthalene dicarboxylic Acid | 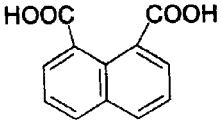 |
| PEG | Polyethylene Glycol$_{5000}$ Hemisuccinyl Ester | 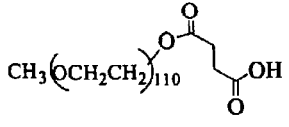 |
FIG. 1B

| Symbol | Name | Structure |
|---|---|---|
| Pyg | Pyroglutamic Acid | 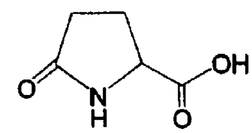 |
| Pyr | 3-Pyridylalanine | 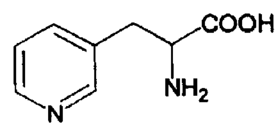 |
| Suc | Succinic Acid | 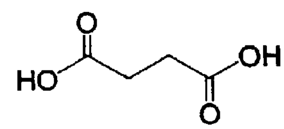 |
| Thi | 2-Thienylalanine | 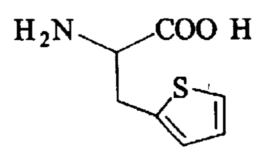 |
| Thz | 3-Thioproline or Thiazolidine-4-carboxylic Acid | 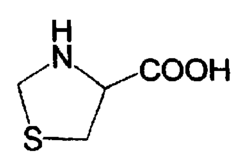 |

FIG. 1C

| Symbol | Name | Structure |
|---|---|---|
| Tic | Tetrahydroisoquinoline-3-carboxylic Acid | 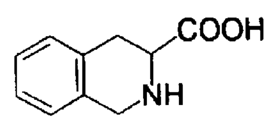 |

| No: | (AA4) | (AA3) | (AA2) | (AA1) | SEQ ID NO: |
|---|---|---|---|---|---|
| 1 | βAla | Ile | Ala | Phe | SEQ ID NO: 1 |
| 2 | βAla | Ile | Ala | Ile | SEQ ID NO: 2 |
| 3 | Tic | Ile | Ala | Leu | SEQ ID NO: 3 |
| 4 | Thi | Ile | Ala | Leu | SEQ ID NO: 4 |
| 5 | Nal | Ile | Ala | Leu | SEQ ID NO: 5 |
| 6 | Amb | Ile | Ala | Leu | SEQ ID NO: 6 |
| 7 | Aib | Ile | Ala | Leu | SEQ ID NO: 7 |
| 8 | βAla | Ile | Ala | Leu | SEQ ID NO: 8 |
| 9 | Thi | Ile | Aib | Leu | SEQ ID NO: 9 |
| 10 | Nal | Ile | Aib | Leu | SEQ ID NO: 10 |
| 11 | βAla | Ile | Aib | Leu | SEQ ID NO: 11 |
| 12 | Amb | Ile | Aib | Leu | SEQ ID NO: 12 |
| 13 | Aib | Ile | Aib | Leu | SEQ ID NO: 13 |
| 14 | βAla | Ile | Gly | Phe | SEQ ID NO: 14 |
| 15 | βAla | Ile | Gly | Ile | SEQ ID NO: 15 |
| 16 | Tic | Ile | Gly | Leu | SEQ ID NO: 16 |
| 17 | Thi | Ile | Gly | Leu | SEQ ID NO: 17 |
| 18 | Nal | Ile | Gly | Leu | SEQ ID NO: 18 |
| 19 | βAla | Ile | Gly | Leu | SEQ ID NO: 19 |
| 20 | Amb | Ile | Gly | Leu | SEQ ID NO: 20 |
| 21 | Aib | Ile | Gly | Leu | SEQ ID NO: 21 |
| 22 | βAla | Ile | Thr | Ile | SEQ ID NO: 22 |
| 23 | βAla | Ile | Tyr | Ile | SEQ ID NO: 23 |
| 24 | βAla | Ile | Ala | Gly | SEQ ID NO: 24 |
| 25 | Ø | Ile | Ala | Leu | SEQ ID NO: 25 |
| 26 | Ø | Ile | N(Me)Ala | Leu | SEQ ID NO: 26 |
| 27 | Ø | Ile | Ala | Phe | SEQ ID NO: 27 |
| 28 | Ø | Ile | Ala | Ile | SEQ ID NO: 28 |
| 29 | Ø | Ile | Aib | Leu | SEQ ID NO: 29 |
| 30 | Ø | Ile | Gly | Phe | SEQ ID NO: 30 |
| 31 | Ø | Ile | Gly | Ile | SEQ ID NO: 31 |
| 32 | Ø | Ile | Gly | Leu | SEQ ID NO: 32 |
| 33 | Ø | Ile | Thr | Ile | SEQ ID NO: 33 |
| 34 | Ø | Ile | Ala | Gly | SEQ ID NO: 34 |
| 35 | βAla | Ile | Tyr | Leu | SEQ ID NO: 35 |
| 36 | βAla | Ile | Tyr | Gly | SEQ ID NO: 36 |

Ø = not present

CD10-ACTIVATED PRODRUG COMPOUNDS

RELATED APPLICATIONS

This application claims priority to U.S. Provisional Application Ser. No. 60/297,596, filed Jun. 11, 2001.

TECHNICAL FIELD

The present invention is directed to new compounds useful as prodrugs. Such prodrugs may be used for treating disease, especially tumors, in patients.

BACKGROUND

Many therapeutic agents, such as anthracyclines and vinca alkaloids, are especially effective for the treatment of cancers. However, these molecules are often characterized in vivo by an acute toxicity, especially a bone marrow and mucosal toxicity, as well as a chronic cardiac toxicity in the case of the anthracyclines and chronic neurological toxicity in the case of the vinca alkaloids. Similarly, methotrexate may be used for the treatment of inflammatory reactions, such as rheumatic diseases, but its high toxicity limits its applications. Development of more specific and safer anti-tumor agents is desirable for greater effectiveness against tumor cells and a decrease in the number and severity of the side effects of these products (toxicity, destruction of non-tumor cells, etc.). Development of more specific anti-inflammatory agents is also desirable.

In order to minimize toxicity problems, therapeutic agents are advantageously presented to patients in the form of prodrugs. Prodrugs are molecules capable of being converted to drugs (active therapeutic compounds) in vivo by certain chemical or enzymatic modifications of their structure. For purposes of reducing toxicity, this conversion should be confined to the site of action or target tissue rather than the circulatory system or non-target tissue. Prodrugs are often characterized by a low stability in blood and serum, however. This is due to the presence of enzymes in blood and serum that degrade, and consequently may activate, the prodrugs before the prodrugs reach the desired sites within the patient's body.

A desirable class of prodrugs that overcomes such problems have been disclosed in Patent Cooperation Treaty International Publication No. WO 96/05863 and in U.S. Pat. No. 5,962,216, both incorporated herein by reference. Further useful prodrug compounds and methods of making such prodrugs are desirable, however, as are methods of making the prodrugs.

Prodrugs that display a high specificity of action, a reduced toxicity, and an improved stability in blood especially relative to prodrugs of similar structure that have existed in the public domain are particularly desirable.

SUMMARY OF THE INVENTION

The compound of the invention is a prodrug form of a therapeutic agent, in which the therapeutic agent is linked directly or indirectly to an oligopeptide, which in turn, is linked to a stabilizing group. The compound is cleavable by CD10. The prodrugs of the invention display a high specificity of action, a reduced toxicity, an improved stability in the serum and blood, and do not move into target cells or do so only miminally until activated by CD10. Also included are conjugates cleavable by CD10 or another thermolysin-like enzyme.

The present invention also relates to a pharmaceutical composition comprising the compound according to the invention and optionally a pharmaceutically acceptable carrier, adjuvant, vehicle, or the like. Articles of manufacture, such as kits for diagnosis or assay are also described.

Further, methods of designing prodrugs and of decreasing toxicity by modifying a therapeutic agent to create a prodrug are disclosed. Such modification provides an improved therapeutic index as compared to the free therapeutic agent. A method of screening for an oligopeptide of appropriate sequence that is cleavable by CD10 can be utilized in designing a prodrug.

The present invention further includes methods of treating a medical condition or disorder, such as a tumor, by administering the prodrug of the invention. The condition involves CD10-associated target cells.

Several processes for making the prodrugs are included, as well.

BRIEF DESCRIPTION OF THE DRAWINGS

FIGS. 1A–1D are a table of abbreviations, names, and structures.

FIG. 10 is a table of oligopeptides useful in the prodrug of the invention.

DETAILED DESCRIPTION

Figure 1D:
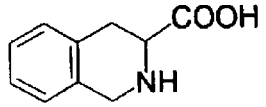

Abbreviations
ACN=Acetonitrile
Aib=Aminoisobutyric acid
All=Allyl
Aloc=Allyloxycarbonyl
Amb=4-(Aminomethyl)benzoic acid
APP=3-Amino-3-phenylpropionic acid
DCC=N,N'-Dicyclohexylcarbodiimide
Boc=t-butyloxycarbonyl
Cap=amino caproic acid
DBN=1,5 Diazabicyclo [4.3.0] non-5-ene
DBO=1,4 Diazabicyclo [2.2.2] octane
DBU=1,8-Diazabicyclo [5.4.0] undec-7-ene
Dox-HCL=Hydrochloride salt of Doxorubicin
DCM=Dichloromethane
DIC=N,N'-Diisopropylcarbodiimide
DIEA=Diisopropylethylamine
Dg=Diglycolic Acid
DMF=Dimethylformamide
Dnr=Daunorubicin
Dox=Doxorubicin
$Et_2O$=diethyl ether
Fmoc=9-Fluorenylmethyloxycarbonyl
Gl=Glutaric Acid
HATU=O-(7-Azabenzotrazol-1-yl)-1,1,3,3-tetramethyluronium-hexafluorophosphate
HBTU=2-(1H-Benzotriazole-1-yl) 1,1,3,3-tetramethyluronium-hexafluorophosphate
HEPES-Hydroxethylpiperidine
HOBt=N-Hydroxybenzotriazole
HPLC=High pressure liquid chromatography
MeOH=Methanol
MeOSuc=Methyl hemisuccinyl/Methyl hemisuccinate
MTD=Maximum tolerated dose
NAA=3-Amino-4,4-diphenylbutyric Acid
Nal=2-Naphthylalanine
Naph=1,8-Naphthalene dicarboxylic acid
Nle=Norleucine
NMP=N-methylpyrrolidine
Nva=Norvaline
PAM resin=4-hydroxymethylphenylacetamidomethyl
Pyg=Pyroglutamic acid
Pyr=3-Pyridylalanine
rRTOP=recombinant Rat TOP
RT, rt=Room temperature
Suc=Succinic Acid/Succinyl
TCE=trichloroethyl
TFA=Trifluoroacetic acid
THF=Tetrahydrofuran
Thi=2-Thienylalanine
Thz=Thiazolidine-4-carboxylic acid
Tic=Tetrahydroisoquinoline-3-carboxylic acid
TOP=Thimet oligopeptidase The invention includes compounds that may be described as prodrug forms of therapeutic agents. The therapeutic agent is linked directly or indirectly to an oligopeptide, which in turn, is linked to a stabilizing group. A linker group between the therapeutic agent and the oligopeptide may optionally be present. The oligopeptide is at least three amino acids in length and preferably three to six amino acids in length. The compound is characterized by its susceptibility to cleavage by the CD10 enzyme.

Prodrug

More particularly, the prodrug of the invention is a modified form of a therapeutic agent and comprises several portions, including:

(1) a therapeutic agent,
(2) an oligopeptide,
(3) a stabilizing group, and
(4) optionally, a linker group.

Each of the portions of the prodrug are discussed in greater detail below. The typical orientation of these portions of the prodrug is as follows:

(stabilizing group)-(oligopeptide)-(optional linker group)-(therapeutic agent).

The stabilizing group is directly linked to the oligopeptide at a first attachment site of the oligopeptide. The oligopeptide is directly or indirectly linked to the therapeutic agent at a second attachment site of the oligopeptide. If the oligopeptide and the therapeutic agent are indirectly linked, then a linker group is present.

Direct linkage of two portions of the prodrug means a covalent bond exists between the two portions. The stabilizing group and the oligopeptide are therefore directly linked via a covalent chemical bond at the first attachment site of the oligopeptide, typically the N-terminus of the oligopeptide. When the oligopeptide and the therapeutic agent are directly linked then they are covalently bound to one another at the second attachment site of the oligopeptide. The second attachment site of the oligopeptide is typically the C-terminus of the oligopeptide, but may be elsewhere on the oligopeptide.

Indirect linkage of two portions of the prodrug means each of the two portions is covalently bound to a linker group. In an alternative embodiment, the prodrug has indirect linkage of the oligopeptide to the therapeutic agent. Therefore, the oligopeptide is covalently bound to the linker group which, in turn, is covalently bound to the therapeutic agent.

In another alternative embodiment, the orientation of the prodrug may be reversed so that a stabilizing group is attached to the oligopeptide at the C-terminus of these oligopeptides and the therapeutic agent is directly or indirectly linked to the N-terminus of the oligopeptide. Thus, in the alternative embodiment, the first attachment site of the oligopeptide may be the C-terminus of the oligopeptide and the second attachment site by the oligopeptide may be the N-terminus of the oligopeptide. The linker group may optimally be present between the therapeutic agent and the oligopeptide. The alternative embodiment of the prodrug of the invention functions in the same manner as does the primary embodiment.

The prodrug of the invention is typically cleavable within its oligopeptide portion. In order for the prodrug to be effective, the prodrug typically undergoes in vivo modification producing a portion of the prodrug that is able to enter the target cell. A first cleavage within the oligopeptide portion of the prodrug may leave an active portion of the prodrug, i.e., a portion of the prodrug that is competent for transport into the target cell, as one of the cleavage products. Alternatively, further cleavage by one or more peptidases may be required to result in a transport-competent portion of the prodrug. The active or transport-competent portion of the prodrug has at least the therapeutic agent and is that part of the prodrug that can enter the target cell to exert a therapeutic effect directly or upon further conversion within the target cell.

Thus, the compound has an active portion, and the active portion is more capable of entering the target cell after cleavage by an enzyme associated with a target cell than prior to such cleavage. The structures of the stabilizing group and oligopeptide are selected to limit clearance and metabolism of the prodrug by enzymes, that may be present in blood or non-target tissues and are further selected to limit transport of the prodrug into cells. The stabilizing group blocks cleavage of the prodrug by exopeptidase in vivo and, additionally, may act in providing preferable charge or other physical characteristics of the prodrug. The amino acid sequence of the oligopeptide is selected for susceptibility to cleavage by CD10, an enzyme associated with target cells and described in greater detail below. Prodrugs having oligopeptides of varying length may be used in the invention, but oligopeptides of at least three amino acids are preferred and oligopeptides of three to six amino acids are especially preferred.

It is desirable to make a therapeutic agent, especially an antitumor and/or anti-inflammatory therapeutic agent, inactive by modification of the therapeutic agent to a prodrug form. According to the invention, the target cells are usually tumor cells or cells, such as macrophages, neutrophils, and monocytes, participating in inflammatory reactions, especially those associated with rheumatic diseases. Modification of the therapeutic agent to a prodrug form also reduces some of the side effects of the therapeutic agents.

Figure 2:
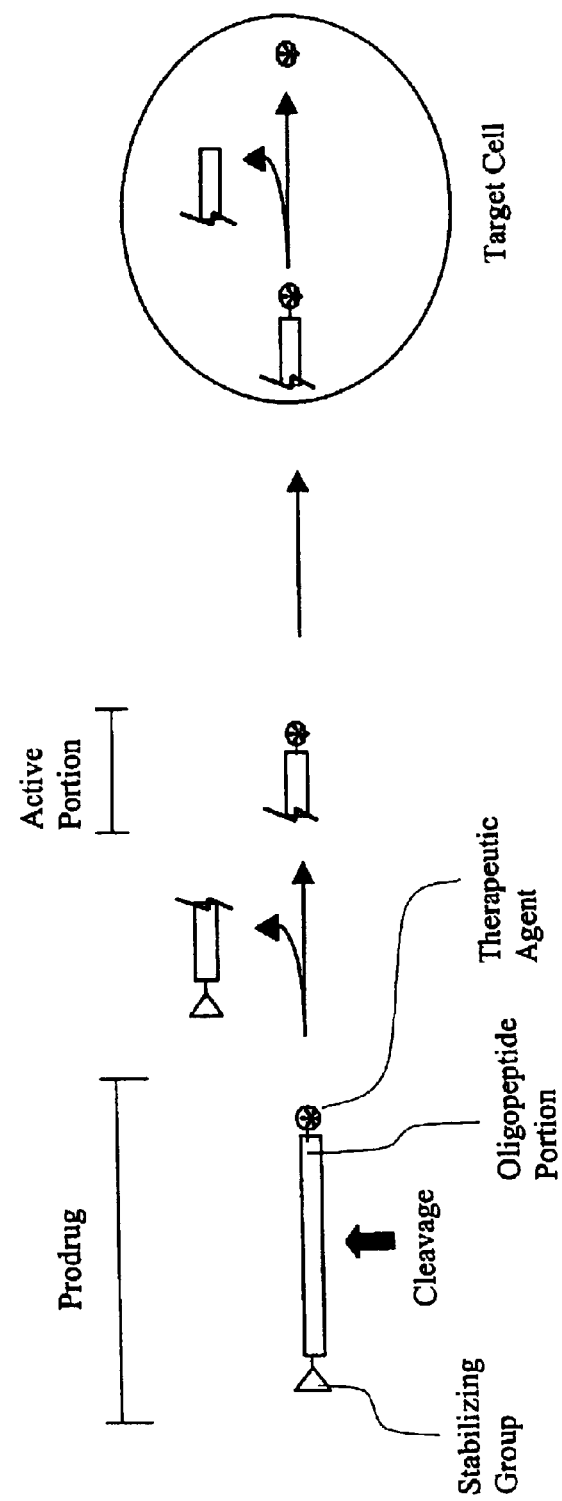
FIG. 2 is an exemplary scheme of cleavage of a prodrug of the invention in the extracellular vicinity of the target cell and within the target cell.

The prodrug is administered to the patient, carried through the blood stream in a stable form, and when in the vicinity of a target cell, is recognized and modified by a target cell associated enzyme. Since the enzyme activity is only minimally present within the extracellular vicinity of normal cells, the prodrug is not activated and its transport-component portion (including the therapeutic agent) gains entry into the normal cells only minimally at best. In the vicinity of tumor or other target cells, however, the increased presence of the relevant enzyme in the local environment causes cleavage of the prodrug. After modification from the prodrug form and entry into the target cell, the therapeutic agent (optionally attached to one or more amino acids and possibly also a linker group) acts to kill or block proliferation of the target cell. The example shown in FIG. 2 depicts a typical prodrug being cleaved extracellularly and gaining entry into the target cell. Once within the target cell, it may be further modified to provide therapeutic effect. While a portion of the prodrug may occasionally gain access to and possibly harm normal cells, the transport-competent portion of the prodrug is freed primarily in the vicinity of target cells. Thus, toxicity to normal cells is minimized.

Compounds of the invention are good prodrugs because they show high stability, i.e., a low level of release of the active therapeutic agent, in the systemic circulation and in normal tissues. Prodrugs of the invention are not activated in the blood or normal tissues to any great extent, yet are activated at tumor or other target sites. Consequently, they have an improved therapeutic index, improved toxicological profile, and favorable pharmacokinetics, as compared to known compounds.

Without limitation to a particular theory, it is believed that compounds having particular sequences recognizable by CD10 are activated in the vicinity of the target cells by the CD10 enzyme or a similar thermolysin-like enzyme. The CD10 is present at least during some portion of the target cell life cycle.

A preferred embodiment of the invention includes compounds that are cleavable in the oligopeptide portion by CD10 but are resistant to cleavage by Thimet oligopeptidase ("TOP"). TOP is believed to be a member of an enzyme class described in greater detail in WO 00/33888. In a further embodiment, the compound preferably includes an oligopeptide that is further characterized by resistance to cleavage by prostate specific antigen (PSA). Such resistance is measured under physiological conditions.

For purposes of this discussion, a compound is resistant to cleavage by a given enzyme if the rate of cleavage by a purified preparation of the given enzyme is no more than 15%, preferably no more than 5%, and ideally no more than 1%, of the rate of cleavage of SEQ ID NO: 49 Suc-βAla-Leu-Ala-Leu conjugated via the carboxyl terminus to the same therapeutic agent as the compound of interest. The rates should be compared under the same assay conditions.

A compound is cleavable by a given enzyme if greater than 10% per hour, preferably greater than 50% per hour, of the compound is cleaved upon incubation of the compound and the enzyme under experimental conditions which model physiological conditions, particularly those outside of the target cell. The concentration of the given enzyme under experimental conditions should be is representative of the concentration of the given enzyme in the extracellular milieu of the target tissue.

As described herein, a compound of the invention comprises:
(1) a therapeutic agent capable of entering a target cell,
(2) an oligopeptide of the formula $(AA)_n\text{-}AA^{P2}\text{-}AA^{P1}\text{-}AA^{P1'}\text{-}(AA)_m$,
wherein:
n and m are integers,
$AA^{P2}$ represents any amino acid,
$AA^{P1}$ represents any amino acid,
$AA^{P1'}$ represents any amino acid, and
each AA independently represents an amino acid,
(3) a stabilizing group, and
(4) optionally, a linker group,
wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the compound by enzymes present in whole blood, and
wherein the compound is cleavable by CD10.
Preferably, n is 0 to 3, m is 0 to 3, and m+n is no more than 3.
The compound is cleavable by CD10 nder physiological conditions.

The compounds of the invention do not include those specifically disclosed in the art. For example, WO 00/33888, U.S. Pat. No. 5,962,216, WO 00/69472, WO 98/52966, U.S. Pat. No. 5,599,686 and other publications may be relevant. Thus, if the oligopeptide of the compound is Leu-Ala-Leu, then the stabilizing group is not succinyl or βAla or the therapeutic agent is not one of doxorubicin and daunorubicin. Similarly, if the oligopeptide is SEQ ID NO: 125 βAla-Leu-Ala-Leu, then the stabilizing group is not succinyl or the therapeutic agent is not one of doxorubicin and daunorubicin. If the oligopeptide is SEQ ID NO: 125 βAla-Leu-Ala-Leu, then the stabilizing group is not glutaryl or the therapeutic agent is not doxorubicin. Furthermore, the compound is not selected from the group consisting of Succ-Ala-Leu-Ala-Leu-Dnr SEQ ID NO: 50, pGlu-Ala-Leu-Ala-Leu-Dox SEQ ID NO: 51, D-Ala-Leu-Ala-Leu-Dnr SEQ ID NO: 52, D-Leu-Ala-Leu-Ala-Leu-Dnr SEQ ID NO: 53, D-Leu-D-Ala-Leu-Ala-Leu-Dnr SEQ ID NO: 54, Acetyl-His-Ser-Ser-Lys-Leu-Gln-Dox SEQ ID NO: 55, Morpholinocarbonyl-His-Ser-Ser-Lys-Leu-Gln-Leu-Dox SEQ ID NO: 56, N-(2-hydroxypropyl)methacrylamide-Gly-Phe-Leu-Gly-Dox SEQ ID NO: 57, N-glutaryl-(4-hydroxyprolyl)-Ala-Ser-cyclohexylglycine-Gln-Ser-Leu-Dox SEQ ID NO: 58, N-Cbz-Gly-Phe-Ala-Leu-Dox SEQ ID NO: 59, and N-Cbz-Gly-Phe-Ala-Leu-PABC-Dox SEQ ID NO: 60.

Target Cell Associated Enzymes

The prodrugs of the invention are designed to take advantage of preferential activation, through interaction with an enzyme associated with the target cell, at or near the site targeted within the body of the patient. The whole of the target cell associated enzyme, or at least the active site of the target cell associated enzyme, may be associated with or bound on the outer cell surface. Alternatively, the target cell associated enzyme may be secreted, released, or present in some other manner in the extracellular vicinity of the target cell.

By way of background, one type of target cell associated enzyme is trouase, described in greater detail in WO 00/33888. Trouase is believed to be a class of enzymes, of which Thimet oligopeptidase ("TOP") is one member. Trouases are highly discriminating in their selectivity and cleavage. Trouase is an endopeptidase that shows a remarkable degree of discrimination between leucine and isoleucine at the carboxyl side of the oligopeptide cleavage site. A defining characteristic is that under appropriate assay conditions, trouase readily cleaves succinyl-βAla-Leu-Ala-Leu-Daunorubicin SEQ ID NO: 61 while it is at least twenty-fold less active with succinyl-βAla-Ile-Ala-Leu-Daunorubicin SEQ ID NO: 62.

Another target cell associated enzyme and of particular relevance to this invention but distinct from the trousase enzymes is CD10.

History of CD10

The first report of CD10 was an activity in the brush border membranes of rat kidney capable of hydrolyzing $^{125}$iodoinsulin B chain at neutral pH (Wong-Leung et al., "Some properties of a microsomal peptidase in rat kidney," Biochem. J. 110: 5P (1968)). The enzyme was hence referred to as kidney brush border neutral proteinase. The enzyme was shown to be a metallopeptidase (Neprilysin, Turner, Handbook of Proteolytic Enzymes 1080–1085 (1998)). CD10 was rediscovered independently as a brain membrane enzyme responsible for the inactivation of the enkephalins (Malfroy et al., "High-affinity enkephalin-degrading peptidase is increased after morphine," Nature, 276: 523–526 (1978)), which led to the use of the trivial name enkephalinase. CD10 is also commonly referred to as neprilysin or neutral endopeptidase 24.11 or EC 3.4.24.11 or NEP in the literature. Cloning and sequencing of the enzyme (Devault et al., "Amino acid sequence of rabbit kidney neutral endopeptidase-24.11 (enkephalinase) deduced from a complementary DNA," EMBO J, 6: 1317–1322 (1987)) led to the recognition that it was identical with a leukocyte cell surface antigen, the common acute lymphoblastic leukemia antigen (CALLA or CD10) which is present on a group of pre-B cell leukemias (LeTarte at al., "Common acute lymphocytic leukemia antigen is identical to neutral endopeptidase," J. Exp. Med, 168: 1247–1253 (1988)).

Biological Activity of CD10

CD10 is essentially an oligopeptidase that hydrolyzes peptides of up to about 40 amino acids in length, although generally the efficiency of hydrolysis declines with increasing length of peptide. One of the most efficiently hydrolyzed substrates is the undecapeptide substance P (Matsas et al., "The metabolism of neuropeptides: the hydrolysis of peptides, including enkephalins, tachykinins and their analogues by endopeptidase-24.11," *Biochem J*, 223: 433–440 (1984)). The principal substrates in vivo appear to be the enkephalins, tachykinins such as substance P, and the atrial natriuretic peptide family.

The primary specificity requirement, according to the literature, is a bulky hydrophobic residue in the P1' position, the enzyme normally functioning as an endopeptidase. Leu in the P1' position gives the highest rates of hydrolysis, whereas Phe exhibits the lowest Km values. The smallest identified substrate in the literature is the chemotactic peptide formyl-Met-Leu-Phe, cleavage occurring at the Met Leu bond (Connelly et al., "Neutral endopeptidase 24.11 in human neutrophils: cleavage of chemotactic peptide," *Proc. Natl. Acad. Sci.*, USA, 86: 7103–7107 (1985)).

The enzyme has an extended active site accommodating at least four amino acid side chains. A consensus sequence for efficient hydrolysis by CD10 is suggested as: -Phe-Phe-Gly+Phe-Leu-(Ala)-SEQ ID NO: 63 (Neprilysin, Turner, *Handbook of Proteolytic Enzymes* 1080–1085 (1998)). With some substrates, CD10 displays peptidyl-dipeptidase character, for example in the hydrolysis of [Leu]-enkephalin: Tyr-Gly-Gly+Phe-Leu SEQ ID NO: 64 (kcat/Km43.9 min-1 mM−1). The C-terminally amidated derivative of [Leu]-enkephalin is hydrolyzed much less efficiently (kcat/Km1.7 min-1 mM−1), reflecting the interaction of the free C-terminal carboxylate group in [Leu]-enkephalin with an arginyl residue (Arg102) in the active site of the enzyme (Bateman et al., "Identification of the active site arginine in rate neutral endopeptidase 24.11 (enkephalinase) as Arg 102 and analysis of a glutamine 102 mutant," *J. Biol. Chem*, 264: 6151–6157 (1989)). Examples of cleavage positions in other biologically active substrates are for substance P, Arg-Pro-Lys-Pro-Gln-Gln+Phe Phe-Gly+Leu-Met-NH$_2$ SEQ ID NO: 65, the most rapid hydrolysis occurring at the Gly+Leu bond, consistent with the consensus sequence for hydrolysis. In neurotensin the following hydrolysis sites are seen: Pyg-Leu-Tyr-Glu-Asn-Lys-Pro-Arg-Arg-Pro-+Tyr+Ile-Leu SEQ ID NO: 66, and in cholecystokinin-8, Asp-Tyr-Met-Gly Trp-Met-Asp+Phe-NH$_2$ SEQ ID NO: 67. Km values for synthetic substrates and natural peptides are usually in the range 10 μM−1 mM.

According to the literature, CD10 exhibits a pH optimum of 6.0 (Neprilysin, Turner, *Handbook of Proteolytic Enzymes* 1080–1085 (1998)). It is inhibited by zinc-chelating reagents and a variety of synthetic inhibitors of the enzyme have been designed, of which the first was thiorphan ([DL-3-mercapto-2benzylpropanoyl]-glycine).

Structural Chemistry of CD10

CD10 is a type II integral membrane protein of the plasma membrane; it exists as an ectoenzyme with the bulk of the protein, including the active site, facing the extracellular space. It is composed of a 23-amino acid N-terminal cytoplasmic domain, a 28-amino acid membrane-spanning domain, and an approximately 700-amino acid extracellular domain that contains the active site (Li et al., "Neprilysin: Assay Methods, Purification, and Characterization," *Methods in Enzymology*, 248:253–263 (1995)). It contains 1 mol of zinc per subunit. Intrachain disulfide bonds are important for the maintenance of structure and activity. The Mr of CD10 ranges from about 85000 to 100000 depending on tissue source, the variation being attributable to differences in glycosylation. cDNA cloning revealed rabbit, rat and human enzymes to consist of 750, 742, and 742 amino acid polypeptides, respectively (Neprilysin, Turner, *Handbook of Proteolytic Enzymes* 1080–1085 (1998)).

CD10 is heavily glycosylated with five or six N-linked glycosylation sites, depending on the species. There appear to be no other post-translational modifications of the enzyme nor have any natural, circulating inhibitors been identified. The CD10 gene, located on chromosomal region 3q21-q27 exists in a single copy, spans more than 80 kb, is composed of 24 exons and is highly conserved among mammalian species (Barker et al., "The common acute lymphoblastic leukemia antigen maps to chromosomal region 3(q21-q27)," *J. Immunol*, 142: 283–287 (1989)).

The C-terminal domain of CD10 contains the HEXXH zinc-binding motif typical of many zinc peptidases. The histidines in this motif (His583 and 587 in the rabbit sequence) constitute two of the zinc ligands with a glutamate at position 646 acting as the third zinc ligand. Glu584 is essential for catalysis.

Biology of CD10

CD10 exhibits a wide tissue distribution, but activity of the enzyme is quite variable among different tissues. The kidney was found to have the highest CD10 concentration, and the enzyme is located primarily on the brush border membranes of the kidney proximal tubule (A. J. Kenny, *Trends Biochem. Sci.* 11, 40 (1986)).

A relatively high concentration of CD10 is found in membranes of the brush border epithelial cells of intestine, lymph nodes, and placenta, whereas significant levels of enzyme are localized to muscle cells in the stomach, small intestine, and colon (A. J. Kenny, S. L. Stephenson, and A. J. Turner, in "Mammalian Ectoenzymes" (A. J. Kenny and A. J. Turner, eds.), p. 169. Elsevier, Amsterdam, (1987)). CD10 is found in lower concentrations in adrenal glands, testis, prostate, fibroblasts, neutrophils, and lung (A. J. Kenny, S. L. Stephenson, and A. J. Turner, in "Mammalian Ectoenzymes" (A. J. Kenny and A. J. Turner, eds.), p. 169. Elsevier, Amsterdam, (1987); N. Sales, I. Dutriez, B. Maziere, M. Ottaviani, and B. P. Roques, Regul. Pept. 33, 209 (1991)). In the upper respiratory tract, the enzyme is thought to occur in epithelial cells, serous cells of submucosal glands, and vessel walls (J. N. Baraniuk, K. Ohkubo, O. J. Kwon, J. Mak, J. Rohde, M. A. Kaliner, S. R. Durham, and P. J. Barnes, *J. Appl. Physiol.* 74, 272 (1993)). The finding of CD10 in human endometrium, where it is confined to the stromal cells, suggests a possible role in regulating the ovulatory cycle (M. L. Casey, J. W. Smith, K. Nagai, L. B. Hersh, and P. C. MacDonald, *J. Biol. Chem.* 266, 23041 (1991); J. R. Head, P. C. MacDonald, and M. L. Casey, *J. Clin. Endocrinol. Metab.* 76, 769 (1993)).

In the mammalian brain, CD10 was found in relatively high concentrations in the choroid plexus, substantia nigra, caudate putamen, globus pallidus, olfactory tubercle, nucleus accumbens, and the substantia gelatinosa of the spinal cord. The enzyme was also detected in the meninges of rat and human spinal cord (G. Waksman, R. Bouboutou, J. Devin, R. Besselievre, M. C. Fournie-Zaluski, and B. P. Roques, *Biochem. Biophys. Res. Commun.* 131, 262 (1985); J. M. Zajac, Y. Charnay, J. M. Soleilhac, N. Sales, and B. P. Roques, *FEBS Lett.* 216, 118 (1987)).

Purification of CD10

CD10 can be purified by the application of immunoaffinity chromatography employing a monoclonal antibody after solubilization of the enzyme from the membrane by detergent treatment. Conventional chromatographic procedures have also been applied in the purification of CD10. Large-scale expression and purification of recombinant neprilysin or CD10 has been achieved from a baculovirus-infected insect cell line. Purification methods are further described in Li et al., "Neprilysin: Assay Methods, Purification, and Characterization," Methods in Enzymology, 248:253–263 (1995).

Assays for CD10

A particularly convenient and sensitive two-stage assay for CD10, which can be adapted for microtiter plate assay, involves the substrate Suc-Ala-Ala+Leu-NHPhNO$_2$ in the presence of S. griseus aminopeptidase as coupling enzyme (Indig et al., "Investigation of neutral endopeptidase (EC 3.4.24.11) and of neutral proteinases (EC 3.4.24.4) using a new two-stage enzymatic reaction," FEBS, 255: 237–240 (1989)). The release of Leu-NHPhNO$_2$ by CD10 is followed by aminopeptidase release of the 4-nitroaniline leaving group which can be monitored at 405 nm.

There are a number of other assay methods used to follow CD10 activity. These include a radiometric assay measuring the hydrolysis of tritiated enkephalin derivatives, fluorometric assays following the hydrolysis of synthetic peptides containing a fluorophor, and assays following the cleavage of internally quenched substrates (Li et al., "Neprilysin: Assay Methods, Purification, and Characterization," Methods in Enzymology, 248:253–263 (1995)).

CD10 in Target Cells

CD10 is expressed by lymphoid precursor cells, germinal center B lymphocytes, and some myelocytes and, thus, is used widely as a cell surface marker for the categorization of acute leukemias and subclassification of malignant lymphomas. CD10 is expressed widely in carcinomas of the gastrointestinal and genitourinary tracts and some sarcomas and may be a useful marker for the differential diagnosis of these tumors (Chu et al., "Paraffin-Section Detection of CD10 in 505 Nonhematopoietic Neoplasms: Frequent Expression of Renal Cell Carcinoma and Endometrial Stromal Sarcoma," Am J Clin Pathol, 113: 374–382 (2000)).

CD10 antigen has been found to be associated widely with precursor B-cell acute lymphoblastic leukemias (Greaves et al., "Selective expression of the common acute lymphoblastic leukemia (gp100) antigen on immature lymphoid cells and their malignant counterparts," Blood, 61: 628–639 (1983)). CD10 is also associated with T-cell acute lymphoblastic leukemias (Weiss et al., "Lymphoblastic lymphoma: an immunophenotype study of 26 cases with comparison to T cell acute lymphoblastic leukemia," Blood, 67: 474–478 (1986)).

CD10 is expressed widely in neoplasms of the genitourinary tract, including renal cell carcinoma, transitional cell carcinoma, and prostatic adenocarcinoma (Chu et al., "Paraffin-Section Detection of CD10 in 505 Nonhematopoietic Neoplasms: Frequent Expression of Renal Cell Carcinoma and Endometrial Stromal Sarcoma," Am J Clin Pathol, 113: 374–382 (2000)). Also, endometrial stromal sarcomas, rhabdomyosarcomas, pancreatic adenocarcinomas, schwannoma, and malignant melanoma are positive for CD10 (Chu et al., "Paraffin-Section Detection of CD10 in 505 Nonhematopoietic Neoplasms: Frequent Expression of Renal Cell Carcinoma and Endometrial Stromal Sarcoma," Am J Clin Pathol, 113: 374–382 (2000)). CD10 positivity was restricted to the apical surface of malignant glandular cells of well-differentiated colonic, pancreatic, and prostatic adenocarcinoma, whereas in poorly differentiated adenocarcinoma and other tumors, such as melanoma, transitional cell carcinoma, renal cell carcinoma, and endometrial stromal sarcoma, the CD10 positivity showed diffuse cytoplasmic or membranous/Golgi patterns (Chu et al., "Paraffin-Section Detection of CD10 in 505 Nonhematopoietic Neoplasms: Frequent Expression of Renal Cell Carcinoma and Endometrial Stromal Sarcoma," Am J Clin Pathol, 113: 374–382 (2000)).

Substrate Specificity

The literature contains several clues regarding the preferred substrates for CD10. Two studies, Pozsgay et al., "Substrate and Inhibitor Studies of Thermolysin-like Neutral Metalloendopeptidase From Kidney Membrane Fractions. Comparison with Bacterial Thermolysin," Biochemistry, 25: 1292–1299 (1986) and Hersh et al., "Comparison of the Subsite Specificity of the Mammalian Neutral Endopeptidase 24.11 (Enkephalinase) to the Bacterial Neutral Endopeptidase Thermolysin," The Journal of Biological Chemistry, 261: 6433–6437 (1986) have described in detail the substrate specificity of CD10. Both these publications are incorporated herein by reference. A brief summarization of the substrate specificity results obtained in these two publications is provided below.

The optimal substrate for CD10 would be an oligopeptide of the formula $AA^{P3}$-$AA^{P2}$-$AA^{P1}$-$AA^{P1'}$-$AA^{P2'}$-$AA^{P3'}$ wherein:

$AA^{P3}$ is Phe or Ala
$AA^{P2}$ is Phe,
$AA^{P1}$ is Gly or Ala
$AA^{P1'}$ is Phe or Leu
$AA^{P2'}$ is Leu
$AA^{P3'}$ is Ala

Of these residues the P3' position appears the least important, according to the literature.

The primary specificity of this membrane-bound metalloendopeptidase is directed toward peptide bonds on the amino side of hydrophobic amino acid residues. Like other proteases, this enzyme has an extended substrate binding site accommodating at least four amino acid residues. The active site of the enzyme apparently contains a hydrophobic pocket at the S1' subsite which interacts with the side chains of hydrophobic amino acid residues.

The turnover rate constants (kcat) and specificity constant (kcat/km) increase greatly when a Gly residue in the P1' is replaced by amino acid residues having hydrophobic side chains. Thus, replacement of the Gly residue by a Leu causes a 140-fold increase in the turnover rate constant and a 370-fold increase in the specificity contant. A decrease, however, in these parameters is seen when a Leu residue is replaced by a Phe residue and even more by a Tyr residue, per reported experiments in the literature.

The kinetic parameters obtained with substrates in which the residues binding to the hydrophobic pocket at the S1' subsite of the enzyme were varied showed that a Leu residue at P1' gave the highest kcat whereas Phe residues gave the lowest Km. Replacement of the Phe residue by a Tyr led to a marked increase in Km and to a decrease in the turnover rate constant.

The presence of a Phe residue in the P1' position, caused a pronounced decrease in the turnover rate constant that was independent of the kind of residue present in the P2' position, suggesting the presence of definite size restrictions on residues binding at the S1' subsite. Indeed, the highest reaction rates were obtained with substrates having an Ala residue in this position. Lowest Km values were obtained with a Phe residue in the P1' position, suggesting that this residue gives the highest binding affinity.

In the P1' subsite, the effect of amino acid substitution is primarily reflected in kcat and consequently kcat/Km. An Ala residue in this position results in 8- and 3.5-fold higher kcat values relative to Gly or Phe. Substitution of a D-amino acid in this position leads to an unreactive substrate. P1' interactions with the enzyme do not involve strong hydrophobic interactions.

Low Km values were obtained for the enzyme when the P2' position was represented by a Phe residue. Also, substrates with this residue gave both high reaction rates and low Km values when the P1' position was replaced by either an Ala or Gly residue.

The major effects of amino acid substitution in the P2' subsite of the enzyme are reflected in Km, with Leu binding 3-fold tighter and Gly 3-fold weaker than Ala. The enzyme hydrophobic interactions at P2' do not affect P1' interactions and thus are directly reflected in Km. Binding interactions at the P2' position appear to involve hydrophobic interactions as seen from the 4-fold lower Km values of the Phe and Ala relative to Gly. A D-Ala residue in the P2' position of the enzyme does not greatly affect catalysis. A D-Ala residue can be accepted at this position, resulting in the largest kcat values.

The fluorogenic substrate dansyl-D-Ala-Gly-(pNO$_2$)Phe-Gly SEQ ID NO: 68 is hydrolyzed at an appreciable rate by the enzyme. The enzyme shows an 8–9-fold increase in the binding of a free acid relative to its amide. This finding suggests that substrate binding to the enzyme is in part dependent on hydrophobic subsite interactions as well as a relatively strong electrostatic interaction with a free COOH-terminal carboxyl group. The consequence of this ionic interaction should be a preference for cleavage of substrates toward their COOH terminus.

The enzyme involved in the activation of the prodrugs of the invention is believed to be associated with the outer membrane of target cells, but is found in the circulation only at very low levels. Most likely it is generated either by the target cells themselves or by normal cells that are associated with the target cells, such as leukocytes, stromal cells, B-cells, neutrophils, or macrophages. The term leukocytes as used herein includes lymphocytes, monocytes, macrophages, granulocytes, polymorphonuclear leukocytes, natural killer cells, dendritic cells, and the like. So, for example, the target cell associated enzyme may be present in some other manner in the extracellular vicinity of the target cell. In many cases, the prodrug of the invention includes a therapeutic agent for the treatment of cancer and the target cell is a tumor cell. Thus, the enzyme may be bound to the tumor cell extra cellular membrane, or it may be present extracellularly because of tumor-associated cells expressing the enzymes.

Compounds which are preferentially cleaved by the enzyme of the invention and are resistant to cleavage elsewhere in the body by other endopeptidases are especially useful. Other enzymes which are known to cleave small peptides at some detectable rate and which could lead to excessive or inappropriate activation of the prodrugs of the invention include TOP, PSA and matrix metalloproteinases. Compounds that are cleavable by CD10 but resistant to cleavage by the TOP enzyme are especially useful. Examples of compounds cleavable by CD10 but resistant to cleavage by TOP are SEQ ID NO: 39 Suc-βAla-Ile-Ala-Leu-Dox and SEQ ID NO: 42 Suc-Ile-Ala-Leu-Dox.

Also useful are compounds of that are cleavable by CD10 but resistant to cleavage by prostate specific antigen (PSA). SEQ ID NO: 39 Suc-βAla-Ile-Ala-Leu-Dox and SEQ ID NO: 42 Suc-Ile-Ala-Leu-Dox are also examples of these types of compounds.

Stabilizing Group

An important portion of the prodrug is the stabilizing group, which serves to protect the prodrug compound from cleavage in circulating blood when it is administered to the patient and thus allows the prodrug to reach the vicinity of the target cell relatively intact. The stabilizing group protects the prodrug from cleavage by proteinases and peptidases present in blood, blood serum, and normal tissue. Since the stabilizing group typically caps the N-terminus of the oligopeptide, and is therefore sometimes referred to as an N-cap or N-block, it serves to ward against peptidases to which the prodrug may otherwise be susceptible.

Ideally, the stabilizing group is useful in the prodrug of the invention if it serves to protect the prodrug from degradation, i.e., cleavage, when tested by storage of the prodrug compound in human blood at 37° C. for 2 hours and results in less than 20%, preferably less than 2%, cleavage of the prodrug by the enzymes present in the human blood under the given assay conditions.

More particularly, the stabilizing group is either
(1) other than an amino acid, or
(2) an amino acid that is either (i) a non-genetically-encoded amino acid or (ii) aspartic acid or glutamic acid attached to the N-terminus of the oligopeptide at the β-carboxyl group of aspartic acid or the γ-carboxyl group of glutamic acid.

For example, dicarboxylic (or a higher order carboxylic) acid or a pharmaceutically acceptable salt thereof may be used as a stabilizing group. Since chemical radicals having more than two carboxylic acids are also acceptable as part of the prodrug, the end group having dicarboxylic (or higher order carboxylic) acids is an exemplary N-cap. The N-cap may thus be a monoamide derivative of a chemical radical containing two or more carboxylic acids where the amide is attached onto the amino terminus of the peptide and the remaining carboxylic acids are free and uncoupled. For this purpose, the N-cap is preferably succinic acid, adipic acid, glutaric acid, or phthalic acid, with succinic acid and adipic acid being most preferred. Other examples of useful N-caps in the prodrug compound of the invention include diglycolic acid, fumaric acid, naphthalene dicarboxylic acid, pyroglutamic acid, acetic acid, 1- or 2-, naphthylcarboxylic acid, 1,8-naphthyl dicarboxylic acid, aconitic acid, carboxycinnamic acid, triazole dicarboxylic acid, gluconic acid, 4-carboxyphenyl boronic acid, a (PEG)$_n$-analog such as polyethylene glycolic acid, butane disulfonic acid, maleic acid, nipecotic acid, and isonipecotic acid.

Further, a non-genetically encoded amino acid such as one of the following may also be used as the stabilizing group: β-Alanine, Thiazolidine-4-carboxylic acid, 2-Thienylalanine, 2-Naphthylalanine, D-Alanine, D-Leucine, D-Methionine, D-Phenylalanine, 3-Amino-3-phenylpropionic acid, γ-Aminobutyric acid, 3-amino-4,4-diphenylbutyric acid, Tetrahydroisoquinoline-3-carboxylic acid, 4-Aminomethylbenzoic acid, and Aminoisobutyric acid.

Additionally, in some experiments intravascular administration of an aggregating positively charged prodrug in mice resulted in acute toxicity. However, no such toxicity was observed when the charge on this prodrug was reversed by derivitization with a negatively charged stabilizing group.

Many cytotoxic compounds inherently have low solubility. Positively charged anthracyclines for example may form aggregates at high concentration and these aggregates may induce intravenous coagulation when the aggregates are administered intravenously. Since many oligopeptides have exposed, positively-charged amino termini at physiological pH, these aggregates may form a polypositively charged surface in vivo and induce a coagulation cascade within a few minutes of administration. This has the potential for rendering any positively charged prodrugs that form aggregates unsuitable for therapeutic use.

As described in greater detail in WO 00/33888, one way of addressing such a potentially dangerous obstacle is to utilize the stabilizing group on the peptide chain N-terminus of a negatively charged or a neutral functionality. For example, the use of succinyl as a stabilizing group on the prodrug may alleviate the acute toxicity of the prodrug. This solves an important problem in the use of peptide prodrugs as practical therapies for intravenous use in humans.

Oligopeptide

Oligopeptides are generally defined as polypeptides of short length, typically twenty amino acids or fewer. An oligopeptide useful in the prodrug of the invention is at least three amino acids in length and preferrably three to six amino acids in length. However, oligopeptides of length beyond the range are also useful.

Numbering Scheme

According to the invention, the oligopeptide portion of the prodrug has a formula $(AA)_n\text{-}AA^{P2}\text{-}AA^{P1}\text{-}AA^{P1'}\text{-}(AA)_m$. In this formula, n and m are integers. As used here, an integer is any positive natural number or zero. The oligopeptide is three or more amino acids in length In the preferred embodiment, n is an integer from 0 to 3 and together, 0 to 3 m+n is no more than 3. Thus, the preferred oligopeptide is 3–6 amino acids in length. Each AA in the formula independently represents an amino acid. Certain amino acids are presented with a superscript, indicating their position relative to the cleavage site by CD10. Particularly, CD10 cleaves between the amino acid at the P1 position, i.e., $AA^{P1}$, and the amino acid at the P1' position, i.e. $AA^{P1'}$.

The oligopeptide is written in the conventional manner with the carboxyl-terminus (or C-terminus) at the right and the amino-terminus (or N-terminus) at the left.

In the oligopeptide of the invention, $AA^{P2}$ represents any amino acid. $AA^{P1}$ also represents any amino acid, as does $AA^{P1'}$. Additional amino acids may be present attached to the core $AA^{P2}\text{-}AA^{P1}\text{-}AA^{P1'}$ section of the oligopeptide. Generally, from 0 to 3 additional amino acids are attached to either $AA^{P2}$ or to $AA^{P1'}$, but more than three are possible. These additional amino acids are presented in the formula as $(AA)_n$ or $(AA)_m$. Each AA in the series represented by $(AA)_n$ or $(AA)_m$ independently represents an amino acid, as well. Thus, when m=1, then $(AA)_m$ represents $AA_{m=1}$ and $AA_{m=1}$ is linked to $AA^{P1'}$. $AA_{m=1}$ is then in the P2' position and may be represented by $AA^{P2'}$. When m=2, then $(AA)_m$ represents $AA^{m=1}\text{-}AA^{m=2}$, with $AA_{m=1}$ in the P2' position and $AA_{m=2}$ in the P3' position and $AA_{m=1}$ is linked to $AA^{P1'}$. When m=3, then $(AA)_m$ represents $AA_{m=1}\text{-}AA_{m=2}\text{-}AA_{m=3}$, (i.e., $AA^{P2'}$ $AA_{P3'}$ $AA^{P4'}$) and $AA_{m=1}$ is linked to $AA^{P1'}$. Similarly, $AA_{n=1}$ or $AA_{n=2}\text{-}AA_{n=1}$ or $AA_{n=3}\text{-}AA_{n=2}\text{-}AA_{n=1}$ may be present, with the $AA_{n=1}$ attached to $AA^{P2}$ and representing $AA^{P3}$. $AA_{n=2}$ is thus in the $P^4$ position, $AA_{n=3}$ is in the $P^5$ position, etc.

Preferred Amino Acids

Unless otherwise indicated, all amino acids are in the L configuration. Although any amino acids may be present in the oligopeptide portion of the prodrug, certain amino acids are preferred.

Particularly, $AA^{P1}$ is preferably selected from the group consisting of arginine, alanine, glycine, leucine, methionine, proline, phenylalanine, tyrosine, glutamine, valine, and serine.

Similarly, $AA^{P1'}$ is preferably selected from the group consisting of leucine, isoleucine, phenylalanine, valine, tyrosine, and proline. $AA^{P1'}$ is preferably a hydrophobic amino acid.

In some embodiments of the invention, particular $A^{P1}$-$AA^{P1'}$ pairings are preferred. Specifically, the $AA^{P1}$-$AA^{P1'}$ combination is preferably selected from the group consisting of Arg-Leu, Arg-Ile, Arg-Phe, Arg-Val, Ala-Phe, Ala-Leu, Gly-Phe, Gly-Leu, Leu-Phe, Leu-Tyr, Met-Leu, Pro-Phe, Pro-Tyr, Pro-Leu, Phe-Leu, Phe-Phe, Tyr-Ile, Tyr-Pro, Tyr-Leu, Gln-Phe, Val-Tyr, Val-Phe, and Ser-Leu.

A hydrophobic amino acid is preferably present as $AA^{P2}$. Thus, isoleucine is a particularly useful amino acid in the P2 position. If m is 1 to 3, then $AA^{m=1}$ is preferably a hydrophobic amino acid, as well.

As examples, the following amino acid sequences may be present in the oligopeptide as at least a portion of the CD10-cleavable sequence: SEQ ID NO: 48 βAla-Leu-Ala-Leu, SEQ ID NO: 25 Ile-Ala-Leu, SEQ ID NO: 8 βAla-Ile-Ala-Leu, Leu-Ala-Leu, Met-Ala-Leu, and Phe-Ala-Leu.

Therapeutic Agents

Therapeutic agents that are particularly advantageous to modify to a prodrug form are those with a narrow therapeutic window. A drug or therapeutic agent with a narrow therapeutic window is one in which the dose at which toxicity is evident, by general medical standards, is very close to the dose at which efficacy is evident.

The therapeutic agent conjugated to the stabilizing group and oligopeptide and, optionally, the linker group to form the prodrug of the invention may be useful for treatment of cancer, inflammatory disease, or some other medical condition. Preferably, the therapeutic agent is selected from the following classes of compounds: Alkylating Agents, Antiproliferative agents, Tubulin Binding agents, Vinca Alkaloids, Enediynes, Podophyllotoxins or Podophyllotoxin derivatives, the Pteridine family of drugs, Taxanes, Anthracyclines, Dolastatins, Topoisomerase inhibitors, Platinum-coordination-complex chemotherapeutic agents, and Maytansinoids.

Particularly, the therapeutic agent is advantageously selected from the following compounds, or a derivative or analog thereof: Doxorubicin, Daunorubicin, Vinblastine, Vincristine, Calicheamicin, Etoposide, Etoposide phosphate, CC-1065, Duocarmycin, KW-2189, Methotrexate, Methopterin, Aminopterin, Dichloromethotrexate, Docetaxel, Paclitaxel, Epithiolone, Combretastatin, Combretastatin $A_4$ Phosphate, Dolastatin 10, Dolastatin 11, Dolastatin 15, Topotecan, Camptothecin, Mitomycin C, Porfiromycin, 5-Fluorouracil, 6-Mercaptopurine, Fludarabine, Tamoxifen, Cytosine arabinoside, Adenosine Arabinoside, Colchicine, Halichondrin B, Cisplatin, Carboplatin, Mitomycin C, Bleomycin, Melphalan, chloroquine, cyclosporin A, and Maytansine. By derivative is intended a compound that results from reacting the named compound with another chemical moiety, and includes a pharmaceutically acceptable salt, acid, base or ester of the named compound. By analog is intended a compound having similar structural and functional properties, such as biological activities, to the named compound.

Linker Groups

A linker group between the oligopeptide and the therapeutic agent may be advantageous for reasons such as the following:

1. As a spacer for steric considerations in order to facilitate enzymatic release of the amino acid linked to the therapeutic agent or other enzymatic activation steps.
2. To provide an appropriate attachment chemistry between the therapeutic agent and the oligopeptide.
3. To improve the synthetic process of making the prodrug conjugate (e.g., by pre-derivitizing the therapeutic agent or oligopeptide with the linker group before conjugation to enhance yield or specificity.)

4. To improve physical properties of the prodrug.

5. To provide an additional mechanism for intracellular release of the drug.

Linker structures are dictated by the required functionality. Examples of potential linker chemistries are hydrazide, ester, ether, and sulfhydryl. Amino caproic acid is an example of a bifunctional linker group. When amino caproic acid is used as part of the linker group, it is not counted as an amino acid in the numbering scheme of the oligopeptide.

Prodrug Design

A method of designing a prodrug is another aspect of the invention and entails initially identifying an oligopeptide of the invention as described above. Then the oligopeptide is linked at a first attachment site of the oligopeptide to a stabilizing group that hinders cleavage of the oligopeptide by enzymes present in whole blood, and directly or indirectly linked to a therapeutic agent at a second attachment site of the oligopeptide. The first attachment site is usually the N-terminus of the oligopeptide but may be the C-terminus of the oligopeptide or another part of the oligopeptide. The second attachment site is usually the C-terminus of the oligopeptide, but may be the N-terminus of the oligopeptide or another part of the oligopeptide. The linkage of the oligopeptide to the therapeutic agent and the stabilizing group may be performed in any order or concurrently.

The resulting conjugate may be tested for cleavability by CD10 utilizing methods known to those of skill in the art. For example the conjugate may be tested for cleavability by CD10 by incubating the conjugate with CD10 purified from a cellular source and analyzing the resulting products by HPLC using fluorescence detection as described in Example 2. The conjugate may be selected as a prodrug if it is cleavable by CD10.

An oligopeptide that is yet not conjugated to the stabilizing group or the therapeutic group may also tested for cleavability by CD10 by the methods used to test cleavability of the conjugate. Cleavability by CD10 is indicative of the oligopeptide as a candidate for designing a prodrug.

Another aspect of the invention is a method of screening to identify an oligopeptide useful for designing a prodrug. Oligopeptides of three or more amino acids are provided and tested for cleavage by CD10. As discussed above, cleavability by CD10 is indicative of the oligopeptide as a candidate for designing a prodrug.

Further testing for cleavability by CD10, but resistance to cleavage by TOP is preferred. Even further testing for cleavability by CD10, but resistance to cleavage by prostate specific antigen (PSA) is preferred. The resulting conjugate may also be tested for stability in whole blood. Test compounds stable in whole blood are selected. Selection is made of compounds cleavable by CD10 and preferably resistant to cleavage by other enzymes. A prodrug designed by such a method is also part of the invention.

Further, the invention includes a method for decreasing toxicity of a therapeutic agent that is intended for administration to a patient. Specifically, a modified, prodrug form of the therapeutic agent is formed by directly or indirectly linking the therapeutic agent to an oligopeptide cleavable by CD10 and preferably also resistant to cleavage by TOP and PSA. The oligopeptide is also linked to a stabilizing group. Preferably, the oligopeptide has the formula $(AA)_n\text{-}AA^{P2}\text{-}AA^{P1}\text{-}AA^{P1'}\text{-}(AA)_m$, wherein:

n and m are integers, $AA^{P2}$ represents any amino acid, $AA^{P1}$ represents any amino acid, $AA^{P1'}$ represents any amino acid, and each AA independently represents an amino acid.

More preferably, n is 0 to 3, m is 0 to 3, and m+n is no more than 3.

The prodrug thus formed provides for decreased toxicity of the therapeutic agent when administered to the patient. The modification of the therapeutic agent in this manner also allows for administration of an increased dosage of the therapeutic agent to the patient relative to the dosage of the therapeutic agent in unconjugated form.

Pharmaceutical Compositions

The invention also includes a pharmaceutical composition comprising a compound, particularly a prodrug compound, according to the invention and, optionally, a pharmaceutically acceptable carrier, for example an adjuvant or vehicle or the like.

More specifically, the invention includes a pharmaceutical composition comprising:

(1) a compound comprising:

(a) a therapeutic agent capable of entering a target cell, (b) an oligopeptide of the formula $(AA)_n\text{-}AA^{P2}\text{-}AA^{P1}\text{-}AA^{P1'}\text{-}(AA)_m$, wherein:

n and m are integers, $AA^{P2}$ represents any amino acid, $AA^{P1}$ represents any amino acid, $AA^{P1'}$ represents any amino acid, and each AA independently represents an amino acid, (c) a stabilizing group, and (d) optionally, a linker group not cleavable by CD10, wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide, wherein the stabilizing group hinders cleavage of the compound by enzymes present in whole blood, and wherein the compound is cleavable by CD10, and (2) a pharmaceutically acceptable carrier.

Preferably, n is 0 to 3, m is 0 to 3, and m+n is no more than 3 in the oligopeptide of the formula $(AA)_n\text{-}AA^{P2}\text{-}AA^{P1}\text{-}AA^{P1'}\text{-}(AA)_m$ of the compound.

The invention also relates to the use of the pharmaceutical composition for the preparation of a medicinal product intended for the treatment of a medical condition.

The pharmaceutical composition may, for example, be administered to the patient parenterally, especially intravenously, intramuscularly, or intraperitoneally. Pharmaceutical compositions of the invention for parenteral administration comprise sterile, aqueous or nonaqueous solutions, suspensions, or emulsions. As a pharmaceutically acceptable carrier or solvent or vehicle, propylene glycol, polyethylene glycol, injectable organic esters, for example ethyl oleate, or cyclodextrins may be employed. Isotonic saline may be part of the pharmaceutical composition. These compositions can also comprise wetting, emulsifying and/or dispersing agents.

The sterilization may be carried out in several ways, for example using a bacteriological filter, by incorporating sterilizing agents in the composition or by irradiation. They may also be prepared in the form of sterile solid compositions that may be dissolved at the time of use in sterile water or any other sterile injectable medium.

The pharmaceutical composition may also comprise adjuvants which are well known in the art (e.g., vitamin C, malic acid, antioxidant agents, etc.) and capable of being used in combination with the compound of the invention in order to improve and prolong the treatment of the medical condition for which they are administered.

Doses for administration to a patient of the compounds according to the invention are generally at least the usual doses of the therapeutic agents known in the field, described in Bruce A. Chabner and Jerry M. Collins, *Cancer Chemotherapy, Lippincott Ed., ISBN* 0-397-50900-6 (1990) or they may be adjusted, within the judgment of the treating physician, to accommodate the superior effectiveness of the prodrug formulations or the particular circumstances of the patient being treated. Hence, the doses administered vary in accordance with the therapeutic agent used for the preparation of the compound according to the invention.

Treatment with Prodrug Compound

A method for ththerapeutic treatment of a medical condition that involves administering, preferably parenterally and more preferably intravenously, to the patient a therapeutically effective dose of the pharmaceutical composition is also within the scope of the invention.

Thus, a method for treating a patient includes administering to the patient a therapeutically effective amount of a compound of the invention.

The prodrug compound is generally useful for the treatment of many medical conditions including cancer, neoplastic diseases, tumors, inflammatory diseases, and infectious diseases. Examples of preferred diseases for treatment are breast cancer, colorectal cancer, liver cancer, lung cancer, prostate cancer, ovarian cancer, brain cancer, and pancreatic cancer. More specifically, since several specific tumor types have been identified as being positive for CD10, treatment for these types of tumors is especially advantageous with the compounds taught herein. Specifically, treatment for one of the following tumor types may be effected: B-cell lymphoblastic leukemia, T-cell lymphoblastic leukemia, lymphoma, including Hodgkin's lymphoma and non-Hodgkin's lymphoma, follicular lymphoma, Burkitt lymphoma, melanoma, ocular melanoma, cutaneous melanoma, colon adenocarcinomas, hepatocellular carcinomas, renal cell carcinoma, ovarian carcinoma, prostate adenocarcinoma, liver carcinoma, transitional cell carcinoma, pancreatic adenocarcinoma, lung carcinoma, breast carcinoma, and colon carcinoma.

Formulated in pharmaceutically acceptable vehicles (such as isotonic saline), the prodrug compound can be administered to animals or humans in intravenous doses ranging from 0.05 mg/kg/dose/day to 300 mg/kg/dose/day. It can also be administered via intravenous drip or other slow infusion method.

Human patients are the usual recipients of the prodrug of the invention, although veterinary usage is also contemplated.

The invention includes a method for treating a disorder having CD10-associated target cells, the method comprising administering to a patient a therapeutically effective amount of a compound comprising:

(1) a therapeutic agent capable of entering a target cell,
(2) an oligopeptide of the formula $(AA)_n\text{-}AA^{P2}\text{-}AA^{P1}\text{-}AA^{P1'}\text{-}(AA)_m$, wherein:
   n and m are integers,
   $AA^{P2}$ represents any amino acid,
   $AA^{P1}$ represents any amino acid,
   $AA^{P1'}$ represents any amino acid, and
   each AA independently represents an amino acid,
(3) a stabilizing group, and
(4) optionally, a linker group not cleavable by CD10, wherein the oligopeptide is directly linked to the stabilizing group at a first attachment site of the oligopeptide and the oligopeptide is directly linked to the therapeutic agent or indirectly linked through the linker group to the therapeutic agent at a second attachment site of the oligopeptide,
wherein the stabilizing group hinders cleavage of the compound by enzymes present in whole blood, and
wherein the compound is cleavable by CD10.

Preferably, n is 0 to 3, m is 0 to 3, and m+n is no more than 3. The compound is cleavable by CD10 under physiological conditions.

The invention also includes, described in greater detail below, a method for treating a disorder such as a tumor in a patient. The method includes the steps of detecting CD10 in a target cell and administering a CD10 cleavable prodrug to the patient if CD10 is associated with the target cell. The detecting step further includes the steps of obtaining a sample of tissue from the patient, combining the sample with a CD10 antibody, and determining if binding of the CD10 antibody to the sample has occurred.

A method for treating a CD10-positive tumor or other CD10-positive target cell comprising administering a CD10 cleavable prodrug to the tumor or other target cell is clearly within the scope of the invention. The CD10 cleavable prodrug is characterized as described above. Also particularly included is a method of treating prostate cancer in a patient comprising administering a prodrug cleavable by CD10 to the patient. The prodrug has a therapeutic agent generally useful for treatment of prostate cancer. Another aspect of the invention is the use of a compound as described for the manufacture of a medicament for treatment of a patient with a disorder having CD10-associated target cells.

As described above, a target cell may be CD10 associated if CD10 is generated by the target cell or by normal cells that are associated with the target cells, such as leukocytes, stromal cells, B-cells, neutrophils, or macrophages. Thus, the CDIO may be bound to the target cell extra cellular membrane, or it may be present extracellularly because of target cell associated cells expressing the enzyme.

Use of Immunoreactivity of CD10 on Human Tumor Tissue to Diagnose And Treat CD10 Positive Tumors The prodrugs of this invention have particularly novel uses in the case of tumors which express CD10 as a surface marker on some or all of the cells in the tumor. Immunohistochemical staining reagents for CD10 can be used as diagnostic markers for tumors with particular susceptibility to CD10-cleavable prodrugs, so that patients can be preselected for treatment. For example, localized production of doxorubicin that is released from CD10-cleavable prodrugs by CD10 on tumor cells would be expected to increase the relative safety of the prodrug compared with treatment with free doxorubicin, which, by contrast, would be expected to act on all cells indiscriminately.

Patients with solid tumors, or suspected presence of tumor cells in tissue, could be screened by biopsy of tumor tissue, following identification of the presence of a tumor by conventional medical procedures. Standard diagnostic monoclonal antibodies are routinely used by histopathologists to identify and classify tumors based on CD10 immunoreactivity. In particular, mouse monoclonal antibody against human CD10, clone 56C6, Novocastra Laboratories, Newcastle, UK is widely used for this purpose (Suzuki, et al., "Imbalance between neutral endopeptidase 24.11 and endothelin-1 expression in human endometrial carcinoma" *Oncology* 60:258–267 (2001); and Chu and Arber, "Paraffin-section detection of CD10 in 505 nonhematopoietic neoplasms. Frequent expression in renal cell carcinoma and endometrial stromal sarcoma," *Am. J. Pathol.* 113:374–382 (2000)).

Small biopsies of tumor may be treated for immunohistochemistry as follows. Biopsies may be fixed in neutral buffered formalin, then paraffin-embedded and sectioned (6–10 microns). The sections may be deparaffinized and rehydrated. For heat-induced epitope retrieval, deparaffinized sections in 0.01 M citrate buffer may be treated in a microwave oven. Immunohistochemical staining may be performed using the avidin-biotin immunoperoxidase technique. Mouse monoclonal antibody against human CD10, clone 56C6, may be used as a 1:20 dilution. Mouse IgG1 MOPC-31C antibody may be used as a negative isotype matching control. The sections are then counterstained with Mayer's hematoxylin. CD10 immunoreactivity is indicated by brown staining specifically around the periphery of positive cells on tissue treated with human anti-CD10, but not the isotype control. These tumors are targets for treatment with a prodrug that is susceptible to cleavage by CD10.

Similarly, other non-solid human tumors that may be positive for CD10, such as hematologic tumors which may not be accessible to biopsy, may be screened for the presence of CD10 by immunochemistry and analyzed by standard clinical flow cytometer (e.g., FACS) methods. Such tumors which screen as positive would also be targets for a prodrug cleavable by CD10. In vitro assays with Ramos (human B cell lymphoma) cell line indicate that CD10 can readily be detected on cells by this method.

Diagnosis or Assay

An article of manufacture, such as a kit, for diagnosis or assay is also within the scope of the invention. Such an article of manufacture would preferably utilize a compound as described above, except that a marker, such as coumarin, is conjugated to the oligopeptide and stabilizing group instead of a therapeutic agent. A marker as used is defined as any moiety that can be conjugated to the oligopeptide and its readily detectable by any method known in the art. At least one reagent useful in the detection of the marker is typically included as part of the kit. Thus, the article of manufacture would include the following:

(1) a compound comprising:
  (a) a marker,
  (b) an oligopeptide of the formula $(AA)_n\text{-}AA^{P2}\text{-}AA^{P1}\text{-}AA^{P1'}\text{-}(AA)_m$, wherein:
    n and m are integers,
    $AA^{P2}$ represents any amino acid,
    $AA^{P1}$ represents any amino acid,
    $AA^{P1'}$ represents any amino acid, and
    each AA independently represents an amino acid,
  (c) a stabilizing group, and
  (d) optionally, a linker group,
  wherein the oligopeptide is directly linked to the stabilizing group at a first attachment site of the oligopeptide and the oligopeptide is directly linked to the marker or indirectly linked through the linker group to the marker at a second attachment site of the oligopeptide,
  wherein the stabilizing group hinders cleavage of the compound by enzymes present in whole blood, and
  wherein the compound is cleavable by CD10, and
(2) at least one reagent useful in the detection of said marker.

Preferably, n is 0 to 3, m is 0 to 3, and m+n is no more than 3,

The article of manufacture may be used, for example, with patient samples to diagnose tumors or to identify patients susceptible to treatment by prodrug therapy.

Process Chemistry General Procedures

Oligopeptide: General Method for the Synthesis of Peptides

The peptide, or oligopeptide, sequences in the prodrug conjugates of this invention may be synthesized by the solid phase peptide synthesis (using either Boc or Fmoc chemistry) methods or by solution phase synthesis. The general Boc and Fmoc methods are widely used and are described in the following references: Merrifield, J. A. Chem. Soc., 88:2149 (1963); Bodanszky and Bodanszky, The Practice of Peptide Synthesis, Springer-Verlag Berlin, 7–161(1994); Stewart, Solid Phase Peptide Synthesis, Pierce Chemical Rockford, (1984).

General Fmoc Solid Phase Method

Figure 3:
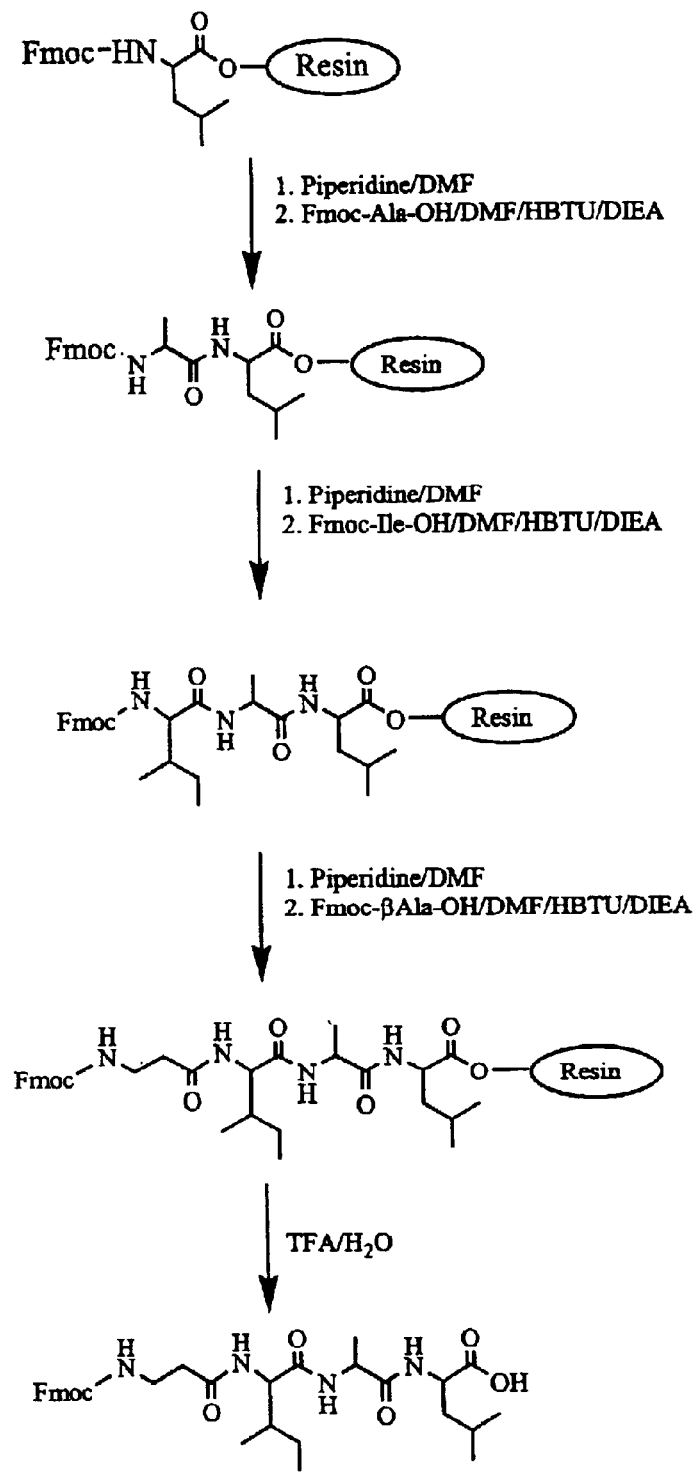
FIG. 3 illustrates a synthesis of Fmoc-βAla-Ile-Ala-Leu (SEQ ID NO: 37), a typical intermediate of the invention.

Using the preferred solid phase synthesis method, either automated or manual, a peptide of desired length and sequence is synthesized through the stepwise addition of amino acids to a growing chain which is linked to a solid resin. Examples of useful Fmoc compatible resins include, but are not limited to, Wang resin, HMPA-PEGA resin, Rink acid resin, or a hydroxyethyl-photolinker resin. The C-terminus of the peptide chain is covalently linked to a polymeric resin and protected α-amino acids were added in a stepwise manner with a coupling reagent. A preferred α-amino protecting group is the Fmoc group, which is stable to coupling conditions and can readily be removed under mild alkaline conditions. The reaction solvents are preferably but not limited to DMF, NMP, DCM, MeOH, and EtOH. Examples of coupling agents are: DCC, DIC, HATU, HBTU. Cleavage of the N-terminal protecting group is accomplished in 10–100% piperidine in DMF at 0–40° C., with ambient temperature being preferred. At the end of synthesis, the final Fmoc protecting group is removed using the above N-terminal cleavage procedure. The remaining peptide on resin is cleaved from the resin along with any acid sensitive side chain protecting groups by treating the resin under acidic conditions. For example, an acidic cleavage condition is a mixture of trifluoroacetic acid (TFA) in dichloromethane. If the hydroxyethyl-photolinker resin is used, the appropriate wavelength for inducing cleavage is λ 365 nm ultraviolet light. A diagrammatic representation of this process is given in FIG. 3.

General N-cap Method via Solid Phase Synthesis

The preparation of N-terminus derivatized peptides is conveniently accomplished on solid phase. When the peptide synthesis is complete, the terminal Fmoc is removed while the peptide is still on the solid support. The N-cap of choice is coupled next using standard peptide coupling conditions onto the N-terminus of the peptide. On completion of the N-cap coupling, the peptide is cleaved from the resin using the procedure described above if the Fmoc synthesis procedure is used.

General Boc Solid Phase Method

For the solid phase method using Boc chemistry, either the Merrifield resin or PAM resin is useful. The amino acids are coupled to the growing chain on solid phase by successive additions of coupling agent activated Boc-protected amino acids. Examples of coupling agents are: DCC, DIC, HATU, and HBTU. The reaction solvents may be DMF, DCM, MeOH, or NMP. Cleavage of the Boc protecting group is accomplished in 10–100% TFA in DCM at 0–40° C., with ambient temperature being preferred. On completion of the peptide chain assembly, the N-terminus protecting group (usually Boc) is removed as described above. The peptide is removed from the resin using liquid HF or trifluoromethane sulfonic acid in dichloromethane.

General Procedure for the Preparation of Fmoc Oligopeptide by Solution Phase Synthesis Alternatively, the prodrug peptide intermediate may be made via a solution phase synthesis, utilizing either Boc or Fmoc chemistry. In the diagrammatic presentation of the methods (FIG. 4), the C-terminal Leu tetrapeptide is generally used as an example, but it will be understood that similar reactions may be performed with other C-terminal peptides of whatever length, as well. The peptide can be built up by the stepwise assembly in analogy to the solid phase method (in the N-terminal direction or in the C-terminal direction) or through the coupling of, for example, two suitably protected dipeptides or a tripeptide with a single amino acid.

Figure 4:
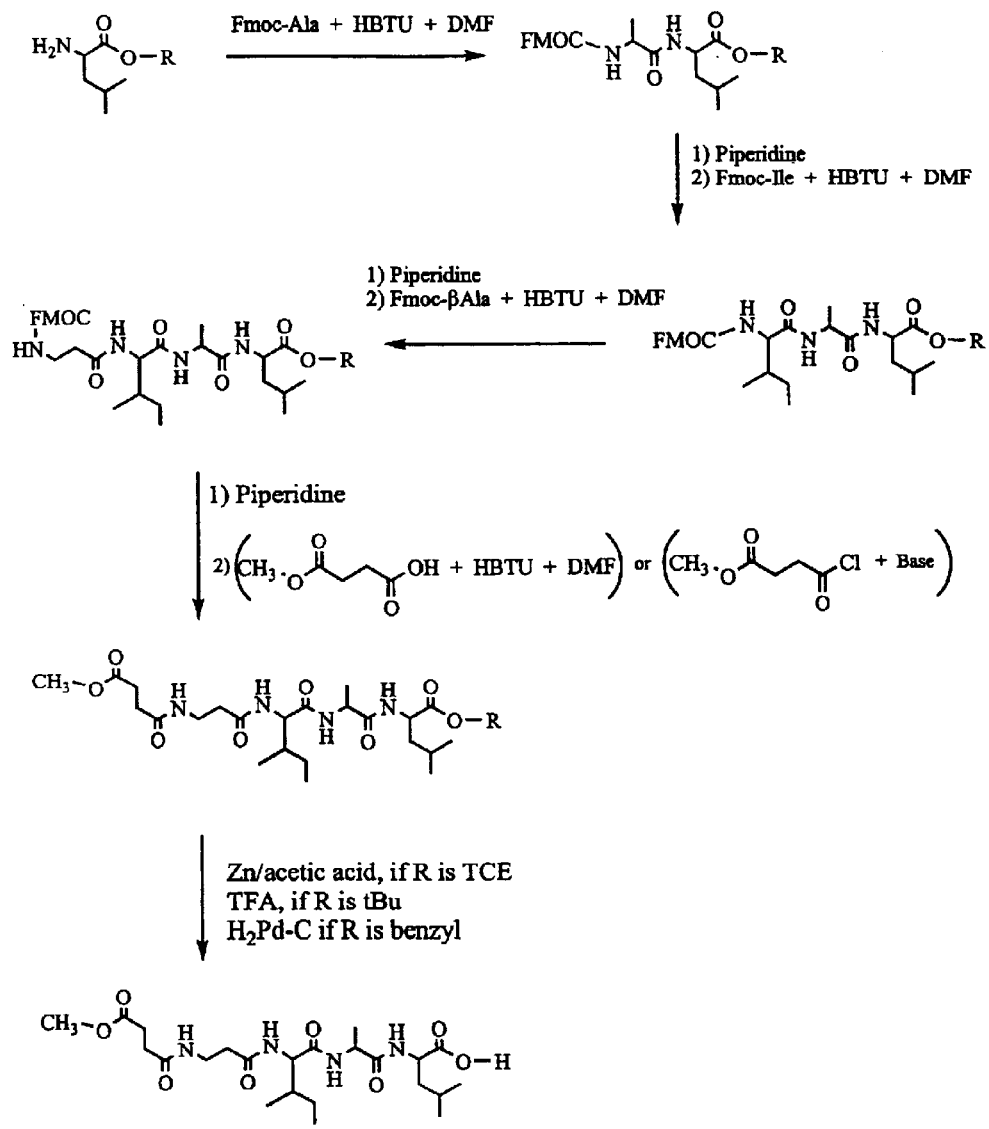
FIG. 4 illustrates an "Fmoc-route" synthesis of Methyl-succinyl-βAla-Ile-Ala-Leu (SEQ ID NO: 38), a typical intermediate of the invention.

One method of solution phase synthesis is a stepwise building up of the prodrug peptide intermediate using Fmoc chemistry, shown in FIG. 4. The C-terminus must be protected to reduce the formation of side products. The C-terminal R group in FIG. 4 is Me, tBu, benzyl or TCE. (Note that when the N-cap is methyl succinyl, the C-terminus R group cannot be Methyl.) Although DMF is given as the solvent, other solvents such as DMSO, $CH_3CN$, or NMP (or mixtures thereof) may be substituted therefor. Pyridine, $Et_3N$ or other bases may be substituted for piperidine in deprotecting the growing peptide chain protected amino terminus. Similarly, although HBTU is given in the diagram above as the activating agent, other activating agents such as DCC, DIC, DCC+HOBt, OSu, activated esters, azide, or triphenyl phosphoryl azide may be used. Additionally, the protected peptide acid chloride or acid bromide may be used to couple directly to the amino acid or peptide fragment. On completion of the oligopeptide assembly, the N-terminus is deprotected and the C-terminus protected peptide is ready to accept the desired N-cap.

General Procedure for the Preparation of N-capped Oligopeptide via Solution Phase Synthesis When constructing the N-capped oligopeptide by solution phase synthesis, the N-cap needs to be synthesized by a slightly modified procedure (FIG. 4). First the C-terminus of the Fmoc oligopeptide needs to be protected with an acid labile or hydrogenation sensitive protecting group compatible with the selective deprotection of the C-terminus over the N-cap. Then the Fmoc protecting group needs to be removed from the oligopeptide to reveal the N-terminus. With the N-terminus deprotected and the C-terminus protected, the oligopeptide is reacted with the activated hemiester of the desired N-cap. The N-cap can be activated using methods for activating amino acids such as DCC or HATU in base and an appropriate solvent. Alternatively, where the methyl-hemisuccinate is used, the coupling may also be done via methyl hemisuccinyl chloride (or other acid halide) (FIG. 4) using an inert solvent in the presence of an organic or inorganic base, such as DIEA, triethylamine or $Cs_2CO_3$. One example of such a synthesis includes reacting methyl-hemisuccinate and βAla-Ile-Ala-Leu benzyl ester SEQ ID NO: 69. The coupling method can be any one of the methods generally used in the art (see for example: Bodanszky, M., *The Practice of Peptide Synthesis*, Springer Verlag, 185 (1984); Bodanszky, M., *Principles of Peptide Synthesis*, Springer Verlag, 159 (1984). The benzyl group then can be removed by catalytic hydrogenation providing the desired N-cap methyl-succinyl form of an oligopeptide. Other examples of suitable, selectively removable C-terminal protecting groups can be, but are not limited to, tBu, alkoxy-methyl and TCE. Other methods of accomplishing this step are described in the literature.

Any combination of the above method can be considered, such as "fragment condensation" of di-, or tripeptides. The reaction conditions are well known in the art and detailed in the citations given. The advantage of the above described methods is the facile purification of the product produced by solution phase synthesis.

Prodrug Conjugate

General Methods for the Conjugation and Deprotection Steps

Figure 5:
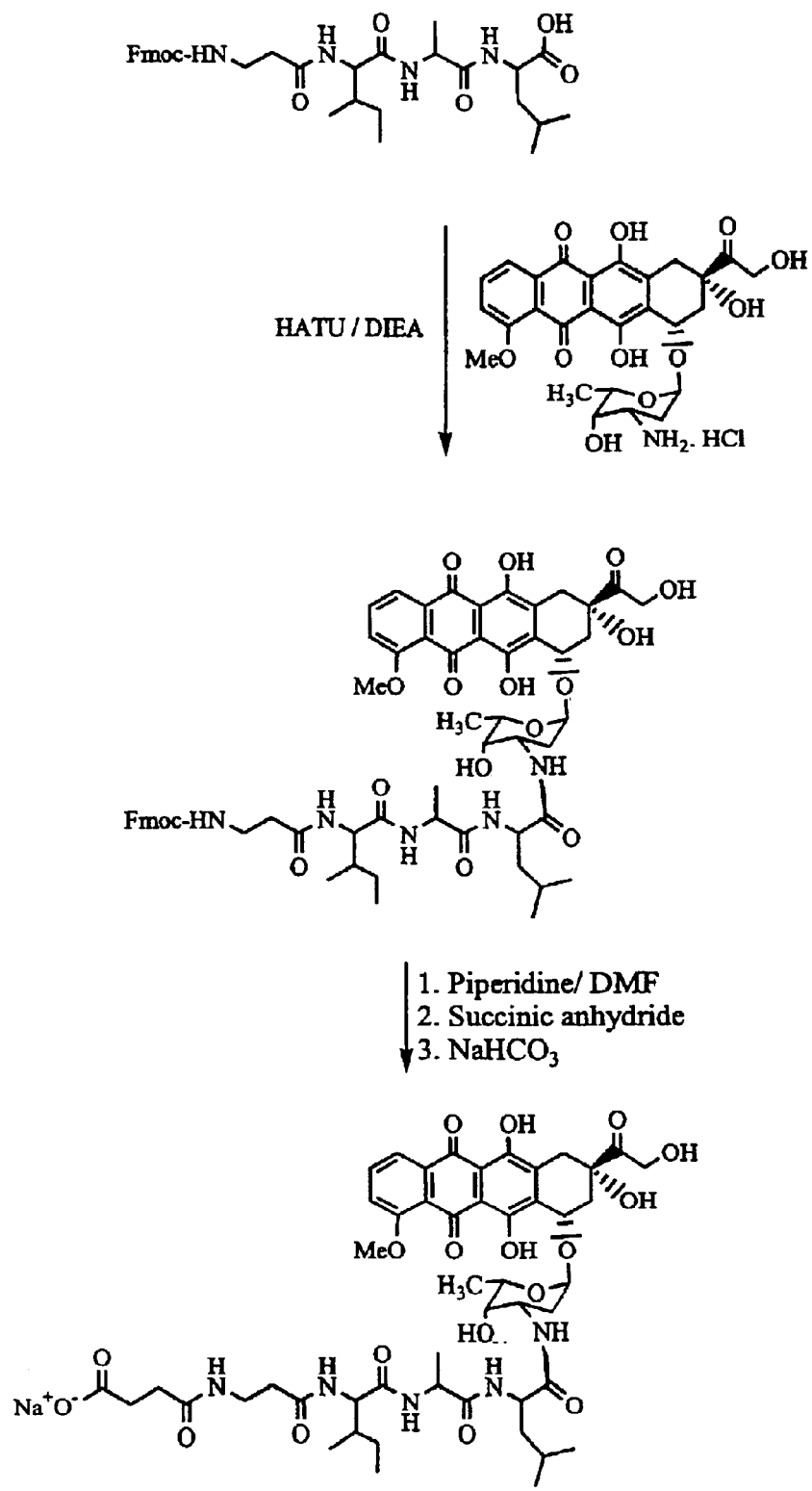
FIG. 5 illustrates an "Fmoc route" synthesis of a salt form of Suc-βAla-Ile-Ala-Leu-DOX (SEQ ID NO: 39), a typical compound of the invention.

The N-cap form of the oligopeptide-therapeutic agent described in this invention can be synthesized by coupling an Fmoc form (which means Fmoc is attached to the N-terminus of the oligopeptide) of the oligopeptide with daunorubicin, doxorubicin, or any appropriate therapeutic agent using any of the standard activating reagents used in peptide synthesis (FIG. 5). The solvent may be toluene, ethyl acetate, DMF, DMSO, $CH_3CN$, NMP, THF, DCM or any other suitable inert solvent as is known in the art and the reagents are soluble therein. The preferred solvents are DMF and NMP. The appropriate temperature range is −25 to +25° C., with ambient temperature being preferred. The activating agent may be selected from one of the following: PyBOP, HBTU, HATU, EDC, DIC, DCC, DCC+HOBT, OSu activated esters, azide, or triphenylphosphorylazide. HBTU or HATU is the preferred activating agent. Alternatively, the acid chloride or the acid bromide of the protected peptide can also be used for this coupling reaction. 2–4 equivalent, advantageously 2–2.5 equivalent of a base is required for the coupling reaction. The base can be selected from inorganic bases such as $CsCO_3$, $Na_2CO_3$, or $K_2CO_3$, or organic bases, such as TEA, DIEA, DBU, DBN, DBO, pyridine, substituted pyridines, N-methyl-morpholine etc., preferably TEA, or DIEA. The reaction can be carried out at temperatures between −15° C. and 50° C., advantageously between −10° C. and 10° C. The reaction time is between 5–90 minutes and is advantageously 20–40 minutes. The product is isolated by pouring the reaction mixture into water and filtering the precipitate formed. The crude product can be further purified by recrystallization from DCM, THF, ethyl acetate, or acetonitrile, preferably from dichloromethane or acetonitrile. The isolated Fmoc form of the oligopeptide therapeutic agent conjugate is then deprotected over 2–90 minutes, preferably 3–8 minutes, using a ten- to hundred-fold excess of base at a temperature between −10° C. and 50° C. Ideally, 5–60 equivalents of the base are preferred. Piperidine is the preferred base to deprotect Fmoc groups. The deprotected amino terminus of the oligopeptide-therapeutic agent conjugate is acylated by a diacid anhydride or a hemi protected activated diacid (i.e., a mono ester which is subsequently deprotected) to give the final N-cap form of the oligopeptide-therapeutic agent.

Figure 6:
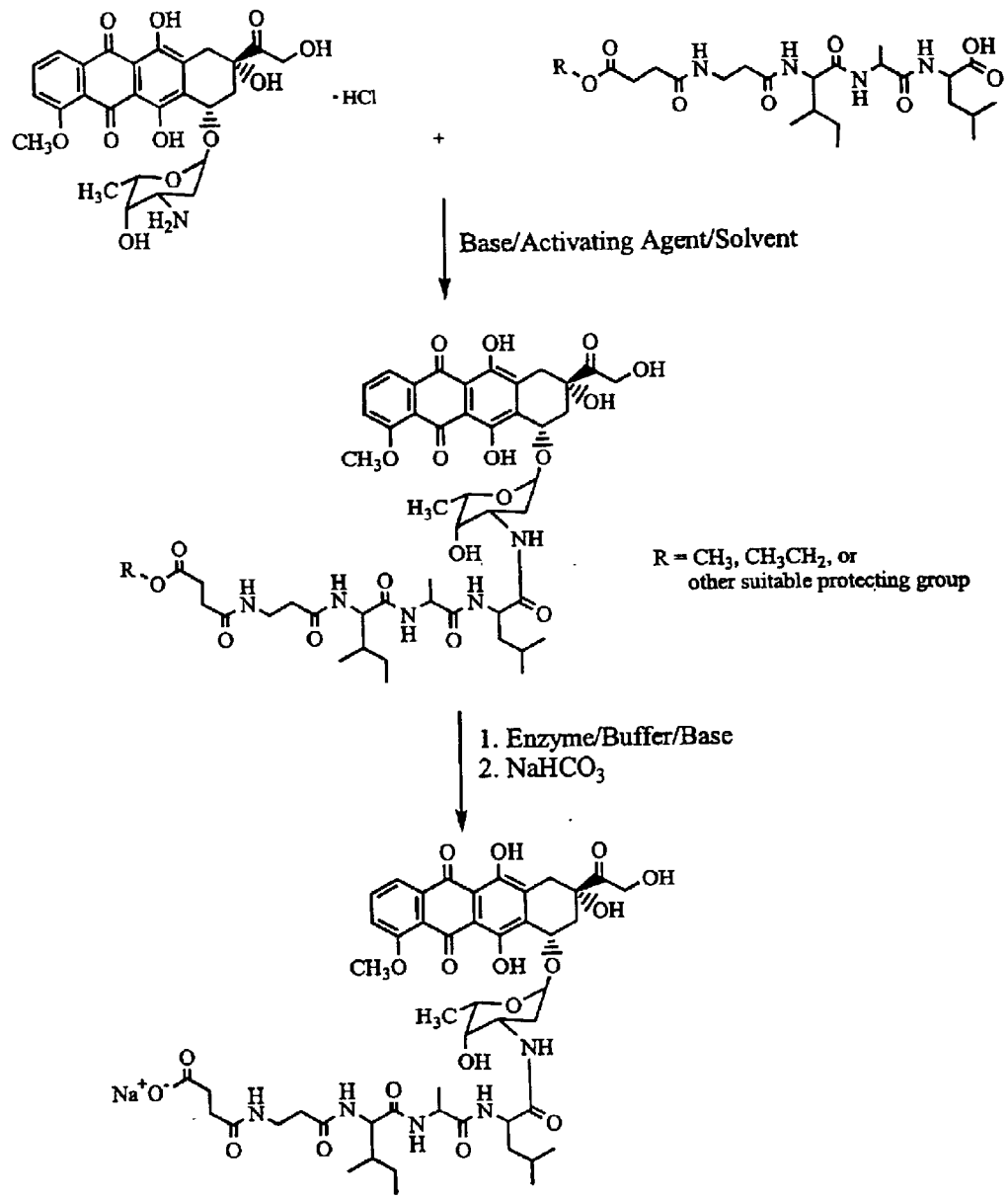
FIG. 6 illustrates an "Ester route" synthesis of a salt form of Suc-βAla-Ile-Ala-Leu-DOX (SEQ ID NO: 39), a typical compound of the invention.

Alternatively, the final prodrug can be similarly prepared from the protected N-cap form of the oligopeptide such as a methyl hemiester form of succinyl-N-cap oligopeptide and conjugated to a therapeutic agent. This method is illustrated in FIG. 6.

The protected N-Cap-oligopeptide-therapeutic agent is now deprotected by methods compatible with the stability of the therapeutic agent. For example, dicarboxyl-peptidyl-anthracyclines may be protected with a methyl group and deprotected with an esterase. For other therapeutic agents, benzyl protecting groups and catalytic hydrogenation may be chosen to deprotect.

The salt form of the negatively charged N-cap oligopeptide-therapeutic agent is carried out with a solvent selected from the following group: alcohol (including methanol, ethanol, or isopropanol), water, acetonitrile, tetrahydrofuran, diglyme or other polar solvents. The sodium source is one molar equivalent of $NaHCO_3$, NaOH, Na$_2$CO$_3$, NaOAc, NaOCH$_3$ (in general sodium alkoxide), or NaH. An ion exchange column charged with Na$^+$ (such as strong or weak ion exchangers) is also useful for this last step of making the salt form of the N-cap oligopeptide therapeutic agent when appropriate. Sodium is described as an example only.

Generally, the prodrug may be converted to a pharmaceutically acceptable salt form to improve solubility of the prodrug. The N-cap-oligopeptide therapeutic agent is neutralized with a pharmaceutically acceptable salt, e.g., NaHCO$_3$, Na$_2$CO$_3$, NaOH tris(hydroxymethyl) aminomethane, KHCO$_3$, K$_2$CO$_3$, CaCO$_3$, NH$_4$OH, CH$_3$NH$_2$, (CH$_3$)$_2$NH, (CH$_3$)$_3$N, acetyltriethylammonium. The preferred salt form of prodrug is sodium, and the preferred neutralizing salt is NaHCO$_3$.

It is well documented that anthracycline type molecules, including doxorubicin and daunorubicin form gels in organic solvents in very low concentrations (Matzanke, B. F., et al., *Eur. J. Biochem.*, 207:747–55 (1992); Chaires, J. B., et al., *Biochemistry*, 21:3927–32 (1982); Hayakawa, E., et al., *Chem. Pharm. Bull.*, 39:1282–6 (1991). This may be a considerable obstacle to getting high yields of clean product when making peptide anthracycline conjugates. The gel formation contributes to the formation of undesirable side reactions. One way to minimize this problem is to use very dilute solutions (1–2%) for the coupling reaction, however it is not practical in a process environment (large amounts of waste, complicated isolation). To overcome this problem urea or other chaotropic agents may be used to break up the strong hydrophobic and hydrogen bonding forces forming the gel. Thus if the coupling reaction is carried out in a urea-containing solvent, advantageously a 20% to saturated solution of urea in DMF or NMP, the side reactions can be kept below 2% even if the concentration of reactants exceeds 10%. This makes the conjugation step practical at high concentrations and produces good yields.

General Enzyme Method

Hydrolysis of protected N-cap-oligopeptide therapeutic agents to the full N-cap compound catalyzed by acids or bases leads to complex reaction mixtures due to the lability of many therapeutic agents even under moderately acidic or basic conditions. Enzymes can promote the hydrolysis without destroying the substrate or the product. Enzymes suitable for this reaction can be esterases or lipases and can be in their natural, water soluble forms or immobilized by cross coupling, or attachment to commercially available solid support materials. Of the soluble enzymes evaluated, *Candida Antarctica* "B" lipase (Altus Biologics) is especially useful. An example of an enzyme immobilized by cross coupling is ChiroCLEC-PC™ (Altus Biologics). *Candida Antarctica* "B" lipase (Altus Biologics) can be immobilized by reaction with NHS activated Sepharose™ 4 Fast Flow (American Pharmacia Biotech). The pH of the reaction mixture during the hydrolysis is carefully controlled and maintained by a pH-stat between 5.5 and 7.5, advantageously between 5.7 and 6.5, via controlled addition of NaHCO$_3$ solution. When the reaction is completed the product is isolated by lyophilization of the filtered reaction mixture. The immobilized enzymes remain on the filter cake and can be reused if desired.

General Allyl or Alkyl Ester Method

Figure 8:
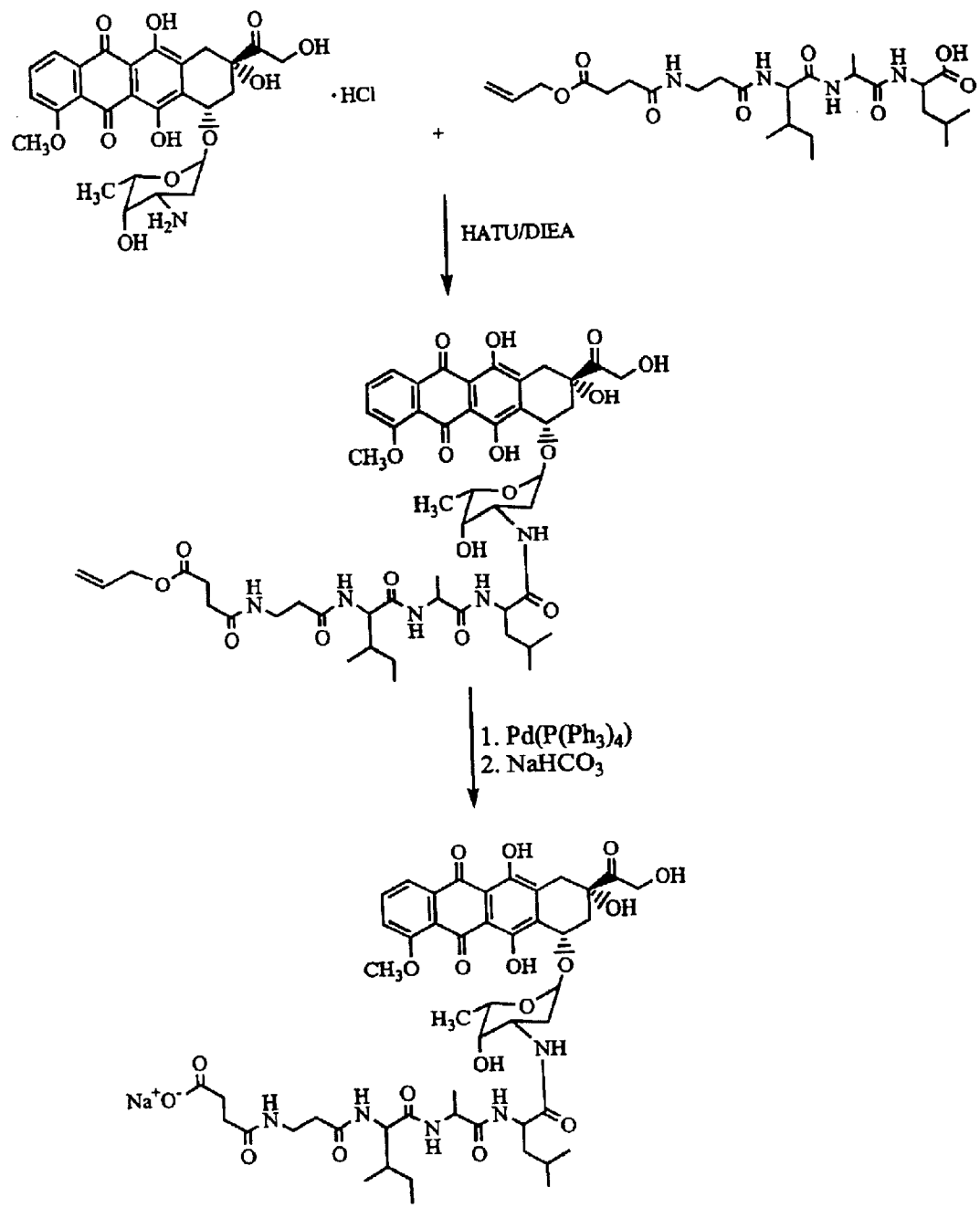
FIG. 8 illustrates an "Allyl ester route" synthesis of a salt form of Suc-βAla-Ile-Ala-Leu-DOX (SEQ ID NO: 39), a typical compound of the invention.

The prodrug can also be prepared via coupling an allyl-hemiester or alkyl hemiester form of the N-cap oligopeptide with a therapeutic agent and then liberating the free acid from the conjugate. FIG. 8 illustrates this process with Succinyl-βAla-Ile-Ala-Leu SEQ ID NO: 70 and doxorubicin.

The coupling of allyl-Succinyl-βAla-Ile-Ala-Leu SEQ ID NO: 71 with doxorubicin can be carried out via any one of the oligopeptide conjugation methods.

Allyl-Succinyl-βAla-Ile-Ala-Leu-doxorubicin SEQ ID NO: 72 can also be synthesized by reacting allyl hemisuccinate, which was prepared via known methods (Casimir, J. R., et al., *Tet. Lett.* 36/19 3409 (1995)), with βAla-Ile-Ala-Leu-doxorubicin SEQ ID NO: 40, Allyl-Succinyl-βAla-Ile-Ala-Leu-doxorubicin SEQ ID NO: 126 similarly as coupling of the protected tetrapeptide precursors to doxorubicin was described in the previous methods, shown in FIG. 5. Suitable inert solvents are THF, dichloromethane, ethyl acetate, toluene, preferably THF from which the acid form of the product precipitates as the reaction progresses. The isolated acid is converted to its sodium salt as described earlier. Reaction times vary between 10–180 minutes, advantageously 10–60 minutes, at temperatures between 0–60° C., preferably 15–30° C.

Removal of the allyl or alkyl group can be done with Pd (0), or Ni(0), advantageously Pd(0) promoted transfer of the allyl or alkyl group to acceptor molecules, as it is well known in the art and documented in the scientific literature (Genet, J-P, et al., *Tet. Lett.*, 50, 497, 1994; Bricout, H., et al. *Tet. Lett.*, 54:1073 (1998), Genet, J-P. et al. Synlett, 680 (1993); Waldmann, H., et al., *Bioorg. Med. Chem.*, 7:749 (1998); Shaphiro, G., Buechler, D., *Tet. Lett.*, 35:5421 (1994)). The amount of catalyst can be 0.5–25 mol % to the substrate.

General Trityl or Substituted Trityl Method

Figure 7:
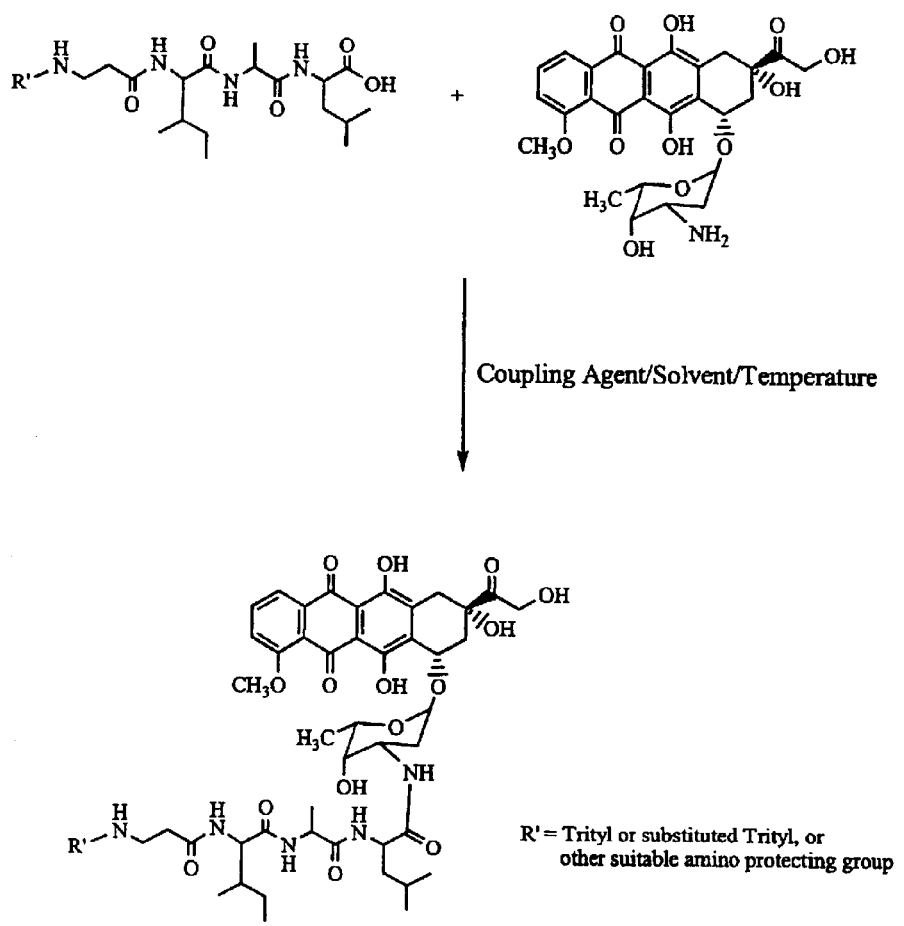
FIG. 7 illustrates a synthesis of an amino-protected βAla-Ile-Ala-Leu-DOX (SEQ ID NO: 40), a typical intermediate of the invention.

The prodrug may also be synthesized via the method shown in FIG. 7. This approach utilizes an R'-oligopeptide, where R' is trityl or substituted trityl. The coupling of R'-oligopeptide with a therapeutic agent can be carried out via any one of the methods described earlier for conjugation of a protected oligopeptide with a therapeutic agent at 30–120 minutes at 0–20° C.

Removal of trityl or substituted trityl group can be achieved under acidic conditions to give the positively charged prodrug. This positively charged prodrug is N-capped as illustrated in FIG. 4 and described earlier. The trityl deprotection can be accomplished with acetic acid, formic acid and dilute hydrochloric acid.

The prodrug can be converted into (succinyl or glutaryl)-oligopeptide-therapeutic agent by reacting with succinic anhydride or glutaric anhydride, then further converted into any pharmaceutically acceptable salt. The solvent for the coupling step may be DMF, DMSO, CH$_3$CN, NMP, or any other suitable solvent is known in the art.

General Inverse Direction Solid Phase Conjugation Method

The prodrug compound of the present invention can be synthesized by using solid phase chemistry via "step wise" inverse (from the N-terminal to the C-terminal) direction methods.

Figure 9:
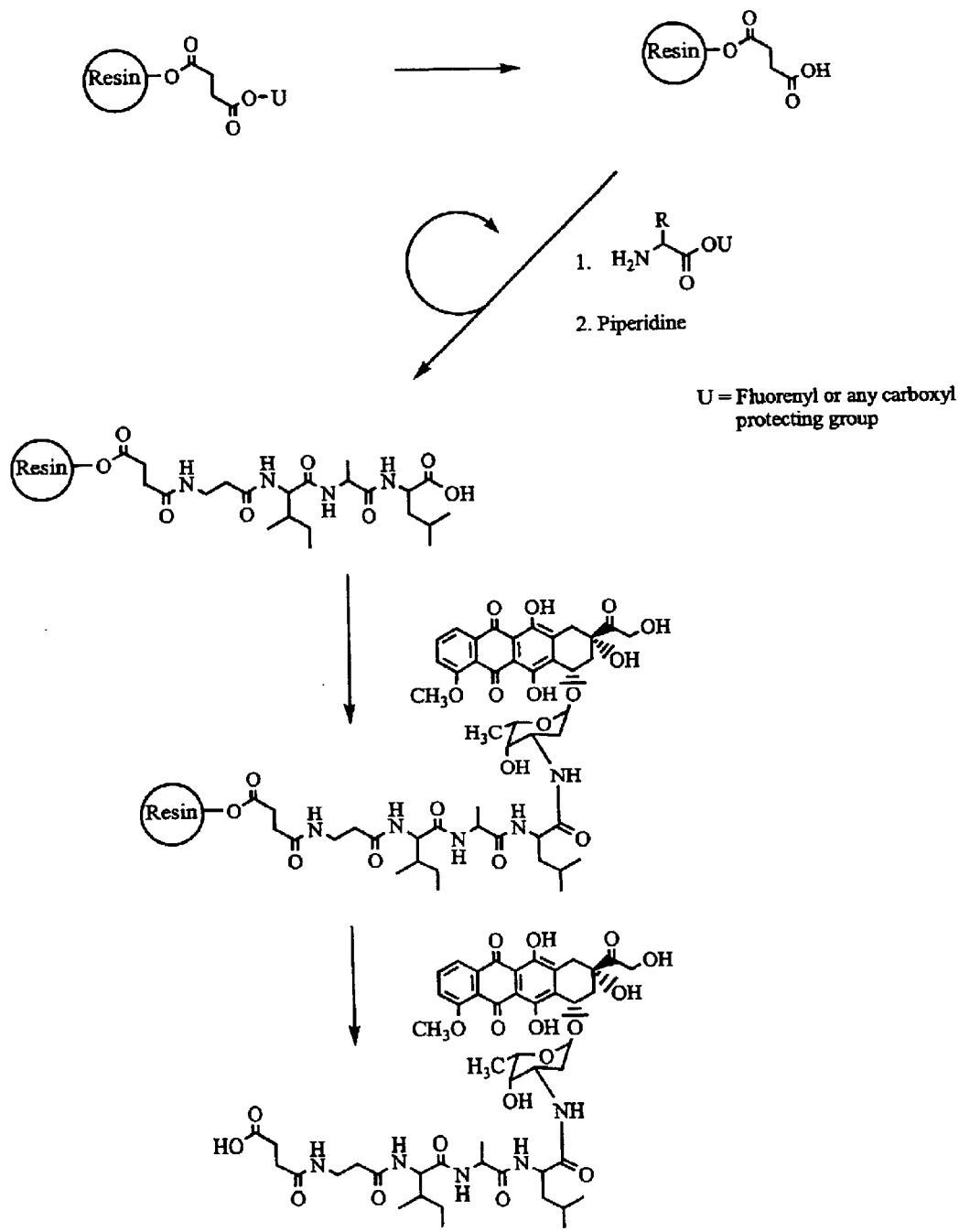
FIG. 9 illustrates a "Resin route" synthesis of Suc-βAla-Ile-Ala-Leu-DOX (SEQ ID NO: 39), a typical compound of the invention.

One way is to use resins to immobilize a succinyl hemiester, for example succinyl-mono-benzyl ester or -allyl ester. Examples of resins could be selected are "Wang Resins" (Wang, S. S., *J. Am. Chem. Soc.*, 95:1328 (1973); Zhang, C., Mjaili, A. M. M., *Tet. Lett.*, 37:5457(1996)), "Rink Resins" (Rink, H., *Tet. Lett.*, 28:3787 (1987)), "Trityl-, or substituted-trityl Resins" (Chen, C., et al.,*J. Am. Chem. Soc.*, 116:2661 (1994); Bartos, K. et al., *Peptides, Proc. 22$^{nd}$ European Peptide Symposium* (1992); Schneider, C. H.; Eberle, A. N. (Eds.), *ESCOM, Leiden*, pp. 281 (1993). The immobilized ester is then deprotected and reacted with, for example, a similarly C-terminal protected βalanine. These steps are then repeated with isoleucine, alanine, and finally leucine esters, followed by the coupling of doxorubicin to the immobilized succinyl-tetrapeptide. The molecule is then liberated from the resin by using mildly acidic conditions to form a free prodrug, such as Suc-βAla-Ile-Ala-Leu-Dox SEQ ID NO: 39. This methodology is represented by the scheme of FIG. 9. Another version of phase synthesis utilizes immobilized succinyl oligopeptide ester. This is then C-terminally deprotected, followed by the coupling step to doxorubicin or other therapeutic agent and finally liberated from the resin as represented by the scheme of FIG. 9. The acid form of the prodrug molecules may then be converted finally into its sodium salt as described above.

General Large Scale Compound Synthesis

The prodrug compound can be synthesized using a simple and efficient three-step process of the invention: (1) coupling an alkyl or allyl ester protected stabilizing group-oligopeptide and a therapeutic agent in the presence of an activating agent to make an alkyl or allyl ester protected stabilizing group-oligopeptide-therapeutic agent conjugate, (2) removing uncoupled therapeutic agent that remains after the coupling step, and (3) deprotecting the alkyl or allyl ester protected stabilizing group-oligopeptide-therapeutic agent conjugate to make the stabilizing group-oligopeptide-therapeutic agent prodrug compound.

Figure 27:
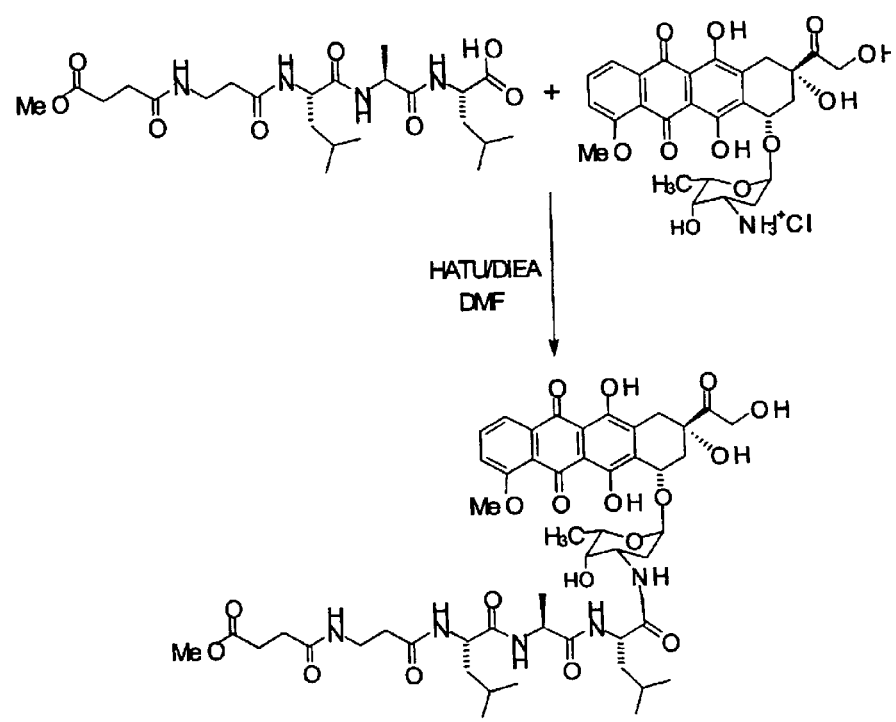
FIG. 27 illustrates a large scale synthesis of MeOSuc-βAla-Leu-Ala-Leu-Dox (SEQ ID NO: 47), a typical intermediate of the invention.

The first step involves the coupling of an alkyl-ester protected oligopeptide fragment to a therapeutic agent. A preferred embodiment of the first step involves the coupling of an alkyl or allyl ester protected stabilizing group oligopeptide, such as MeOSuc-βAla-Leu-Ala-Leu-OH SEQ ID NO: 49, with a therapeutic agent, such as doxorubicin (FIG. 27), using an activating agent, such as HATU, to give alkyl or allyl ester protected stabilizing group oligopeptide therapeutic agent conjugate, e.g., MeOSuc-βAla-Leu-Ala-Leu-Dox SEQ ID NO: 47. The focus of this step is on the purity and the yield of the methyl ester, since it was found that the hydrolysis step did not have an impact on purity. Preferably the molar ratio of the alkyl or allyl ester protected stabilizing group oligopeptide to the therapeutic agent will be between 2:1 and 1:1. More preferably the molar ratio is between 1.75:1 and 1.5:1. Most preferably the molar ratio is 1.66:1.

The coupling of the alkyl or allyl ester protected stabilizing group oligopeptide and a therapeutic agent is preferably performed by: (a) combining the alkyl or allyl ester protected stabilizing group oligopeptide and the therapeutic agent in DMF, (b) adding DIEA, (c) reacting the alkyl or allyl ester protected stabilizing group oligopeptide and the therapeutic agent in the presence of the activating agent to form the conjugate, and (d) precipitating the conjugate by adding a brine solution to form a precipitate. Preferably the molar ratio of the DIEA and the alkyl or allyl ester protected stabilizing group-oligopeptide is between 3:1 and 1.5:1. More preferably the molar ratio is between 2.5:1 and 2:1. Most preferably the molar ratio is 2.18:1. The reacting step is preferably performed at 0° C., for 30 minutes. Preferably the molar ratio of the activating agent and the alkyl or allyl ester protected stabilizing group-oligopeptide is between 1.5:1 and 1:1. More preferably, the molar ratio is 1.1:1. The brine solution is preferably between 20% (w/v) and 40% (w/v) of NaCl in water. More preferably the brine solution is between 25% (w/v) and 35% (w/v) of NaCl in water. Most preferably the brine solution is 30% (w/v) of NaCl in water. The conjugate is preferably precipitated in a brine solution, wherein the pH is between 5.0 and 7.0, inclusive. Most preferably, the conjugate is precipitated at a pH between 5.8 and 6.0.

Since many therapeutic agents are toxic substances, it is preferable to eliminate any free therapeutic agent from the coupled product. The removing step is preferably performed by: (a) dissolving the conjugate in DMF, (b) dissolving a scavenger resin in anhydrous DMF, (c) adding the alkyl or allyl ester protected stabilizing group oligopeptide therapeutic agent conjugate formed in the coupling step to the scavenger resin to form a conjugate-resin mixture, (d) maintaining the mixture at between 0° C. and 30° C. for 2 to 24 hours wherein the uncoupled therapeutic agent reacts with the resin, (e) removing the resin from the mixture, and (f) precipitating the remainder by adding a brine solution to form a precipitate of the alkyl or allyl ester protected stabilizing group oligopeptide therapeutic agent conjugate. Preferably the scavenger resin is polystyrene-isocyanate (PS-isocyanate), PS-methylisocyanate, PS-thioisocyanate, PS-methylthioisocyanate, PS-sulfonyl chloride, PS-methylsulfonyl chloride or PS-benzaldehyde. Most preferably, the scavenger resin is PS-isocyanate. The removing step is preferably performed to remove free therapeutic agent, which is an anthracycline.

The third step is deprotecting the alkyl or allyl ester protected stabilizing group-oligopeptide-therapeutic agent conjugate, preferably via hydrolysis by an enzyme, more preferably via hydrolysis by an esterase, which directly gives the prodrug compound in good yield with a final purity of at least 90%. For example, the third step may be the hydrolysis of the methyl ester group in MeOSuc-βAla-Leu-Ala-Leu-Dox SEQ ID NO: 47 by an enzyme, such as CLEC CAB (crosslinked Candida Antartica B Lipase), which directly gives the sodium salt of Suc-βAla-Leu-Ala-Leu-Dox SEQ ID NO: 41 in quantitative yields with high purity.

The enzyme is preferably either crosslinked or immobilized on a solid support. The esterase may be pig liver esterase, Candida antartica B Lipase, Candida rugosa lipase, Pseudomonas cepacia lipase, pig liver esterase immobilized on sepharose, Candida antartica B lipase immobilized on sepharose, CLEC-PC™ (Pseudomonas Cepacia lipase), CLEC-CAB (Candida antartica B lipase), or CLEC-CR (Candida rugosa lipase). Deprotecting via hydrolysis by an enzyme is preferably performed by: (a) washing the enzyme to remove free enzyme, (b) adding the washed enzyme to the alkyl or allyl ester protected stabilizing group-oligopeptide-therapeutic agent conjugate, (c) reacting the enzyme with the conjugate at between 15° C. and 40° C., inclusive, at a pH between 5.0 and 8.0, inclusive, for at least 18 hours, to create the stabilizing group-oligopeptide-therapeutic agent prodrug compound, and (d) separating the enzyme from the prodrug compound. Most preferably additional washed crosslinked or immobilized enzyme is added after the step of reacting the enzyme with the conjugate, prior to separating the enzyme from the prodrug compound.

Removal of Free Therapeutic Agent

Figure 11:
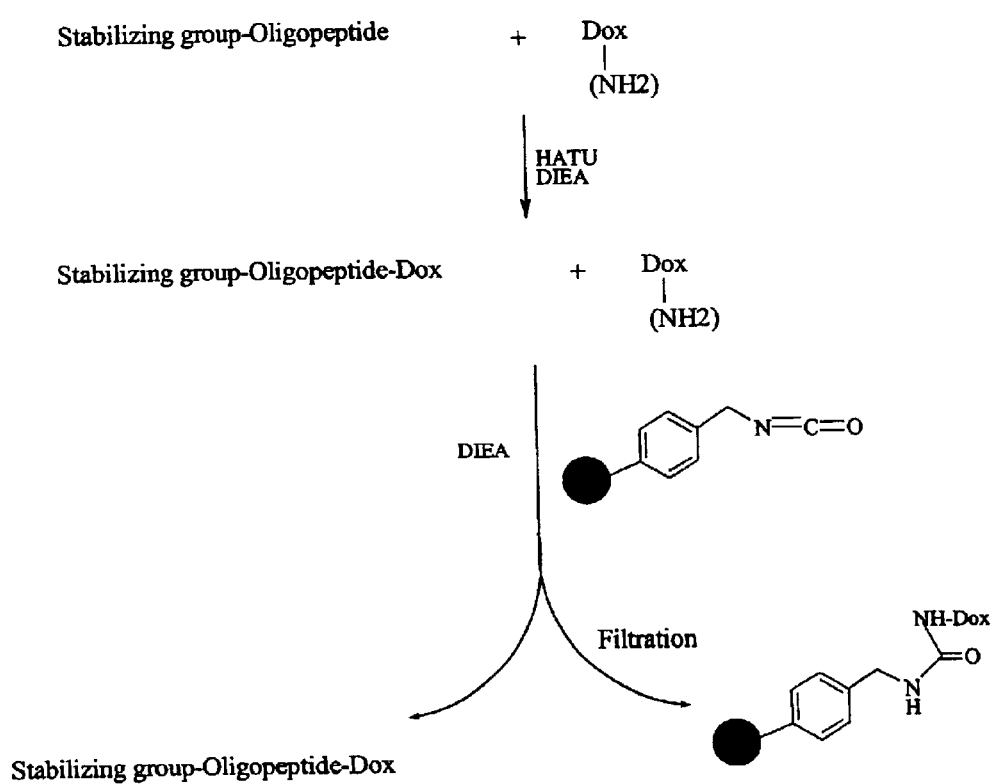
FIG. 11 illustrates the removal of free therapeutic agent through the use of scavenging resin or beads.

Unconjugated therapeutic agent may be present late in the process of making the prodrug. For example, during the coupling step of (stabilizing group)-(oligopeptide) conjugate with doxorubicin as the therapeutic agent, it was found, in some instances, that the reaction did not proceed completely. There was about 2–4% of residual doxorubicin remaining in the coupled product. Initial attempts to remove doxorubicin completely from the product by acidic washes did not result in complete removal. The complete removal of the free therapeutic agent was effected by the process outlined in Example 47 and FIG. 11 that utilizes scavenging resin or beads.

The crude product, which contains the intermediate and residual doxorubicin, was dissolved in DMF and polystyrene methylisocyanate or polystyrene sulfonyl chloride resin or beads were added. The reaction was stirred for 60 minutes. The free amino group of doxorubicin reacts with the isocyanate or sulfonyl chloride group on the beads to form a urea or sulfonamide derivative. The solid beads with doxorubicin attached to them were then separated from the desired product by filtration. The desired product remains in the DMF solution. This approach seems to be a very mild and effective method for removing residual therapeutic agent from the product.

Thus, the invention includes a method of making a compound comprising:
(1) selecting an Fmoc-protected oligopeptide of the formula

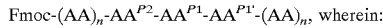
Fmoc-(AA)$_n$-AA$^{P2}$-AA$^{P1}$-AA$^{P1'}$-(AA)$_n$, wherein:

n and m are integers,
AA$^{P2}$ represents any amino acid,
AA$^{P1}$ represents any amino acid,
AA$^{P1'}$ represents any amino acid, and
each AA independently represents an amino acid,
(2) coupling the Fmoc-protected oligopeptide to a therapeutic agent by activating the Fmoc-protected oligopeptide with an activating agent in the presence of the therapeutic agent to form an Fmoc-protected oligopeptide-therapeutic agent conjugate,
(3) deprotecting the Fmoc-protected oligopeptide-therapeutic agent conjugate by contacting it with a base to form an oligopeptide-therapeutic agent conjugate, and
(4) coupling the oligopeptide-therapeutic agent conjugate to a stabilizing group to form the compound.
Preferably, n is 0 to 3, m is 0 to 3, and m+n is no more than 3.

Alternatively, a method of making a compound comprises the following steps:
(1) selecting an oligopeptide of the formula (AA)$_n$-AA$^{P2}$-AA$^{P1}$-AA$^{P1'}$-(AA)$_m$, wherein:
n and m are integers,
AA$^{P2}$ represents any amino acid,
AA$^{P1}$ represents any amino acid,
AA$^{P1'}$ represents any amino acid, and
each AA independently represents an amino acid
(2) coupling the oligopeptide to an alkyl ester-protected stabilizing group to form an alkyl ester-protected stabilizing group-oligopeptide conjugate,
(3) coupling the alkyl ester-protected-stabilizing group-oligopeptide conjugate to a therapeutic agent by activating the alkyl ester-protected stabilizing group-oligopeptide conjugate with an activating agent in the presence of a therapeutic agent to form an alkyl ester-protected stabilizing group-oligopeptide-therapeutic agent conjugate, and
(4) deprotecting the alkyl ester-protected stabilizing group-oligopeptide therapeutic agent conjugate to form the compound.
Preferably, n is 0 to 3, m is 0 to 3, and m+n is no more than 3.

A compound of the invention may also be made via the following steps:
(1) selecting an oligopeptide of the formula (AA)$_n$-AA$^{P2}$-AA$^{P1}$-AA$^{1'}$-(AA)$_m$, wherein:
n and m are integers,
AA$^{P2}$ represents any amino acid,
AA$^{P1}$ represents any amino acid,
AA$^{P1'}$ represents any amino acid, and
each AA independently represents an amino acid (2) coupling the oligopeptide to an allyl ester-protected stabilizing group to form an allyl ester-protected stabilizing group-oligopeptide conjugate,
(3) coupling the allyl ester-protected-stabilizing group-oligopeptide conjugate to a therapeutic agent by activating the allyl ester-protected stabilizing group-oligopeptide conjugate with an activating agent in the presence of a therapeutic agent to form an allyl ester-protected stabilizing group-oligopeptide-therapeutic agent conjugate, and
(4) deprotecting the allyl ester-protected stabilizing group-oligopeptide therapeutic agent conjugate to form the compound.
Preferably, n is 0 to 3, m is 0 to 3, and m+n is no more than 3.

Yet another method for making a compound of the invention comprises the following steps:
(1) selecting a trityl-protected oligopeptide of the formula

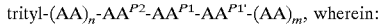
trityl-(AA)$_n$-AA$^{P2}$-AA$^{P1}$-AA$^{P1'}$-(AA)$_m$, wherein:

n and m are integers,
AA$^{P2}$ represents any amino acid,
AA$^{P1}$ represents any amino acid,
AA$^{P1'}$ represents any amino acid, and
each AA independently represents an amino acid,
(2) coupling the trityl-protected oligopeptide to a therapeutic agent by activating the trityl-protected oligopeptide with an activating agent in the presence of a therapeutic agent, thereby making a trityl-protected oligopeptide-therapeutic agent conjugate,
(3) deprotecting the trityl-protected oligopeptide-therapeutic agent conjugate under acidic conditions to form an oligopeptide-therapeutic agent conjugate, and
(4) coupling the oligopeptide-therapeutic agent conjugate with an stabilizing group to form the compound.
Preferably, n is 0 to 3, m is 0 to 3, and m+n is no more than 3.

Another possible step in connection with any of these methods is removing uncoupled therapeutic agent by use of scavenging resin or beads. Further, the compound may be neutralized with a pharmaceutically acceptable salt if desired.

Specific Compounds

The compound of the invention includes the following specific examples:
Suc-βAla-Leu-Ala-Leu-Dox SEQ ID NO: 41, Suc-Ile-Ala-Leu-Dox SEQ ID NO: 42, Suc-βAla-Ile-Ala-Leu-Dox SEQ ID NO: 39, Suc-Leu-Ala-Leu-Dox SEQ ID NO: 45, Suc-Met-Ala-Leu-Dox SEQ ID NO: 73, and Suc-Phe-Ala-Leu-Dox SEQ ID NO: 74.

Examples of compounds cleavable by CD10 but resistant to cleavage by TOP are as follows: Suc-βAla-Ile-Ala-Leu-Dox SEQ ID NO: 39 and Suc-Ile-Ala-Leu-Dox SEQ ID NO: 42.

EXAMPLES

Example 1

Protein Specific Activity of Cell Homogenates

Figure 12:
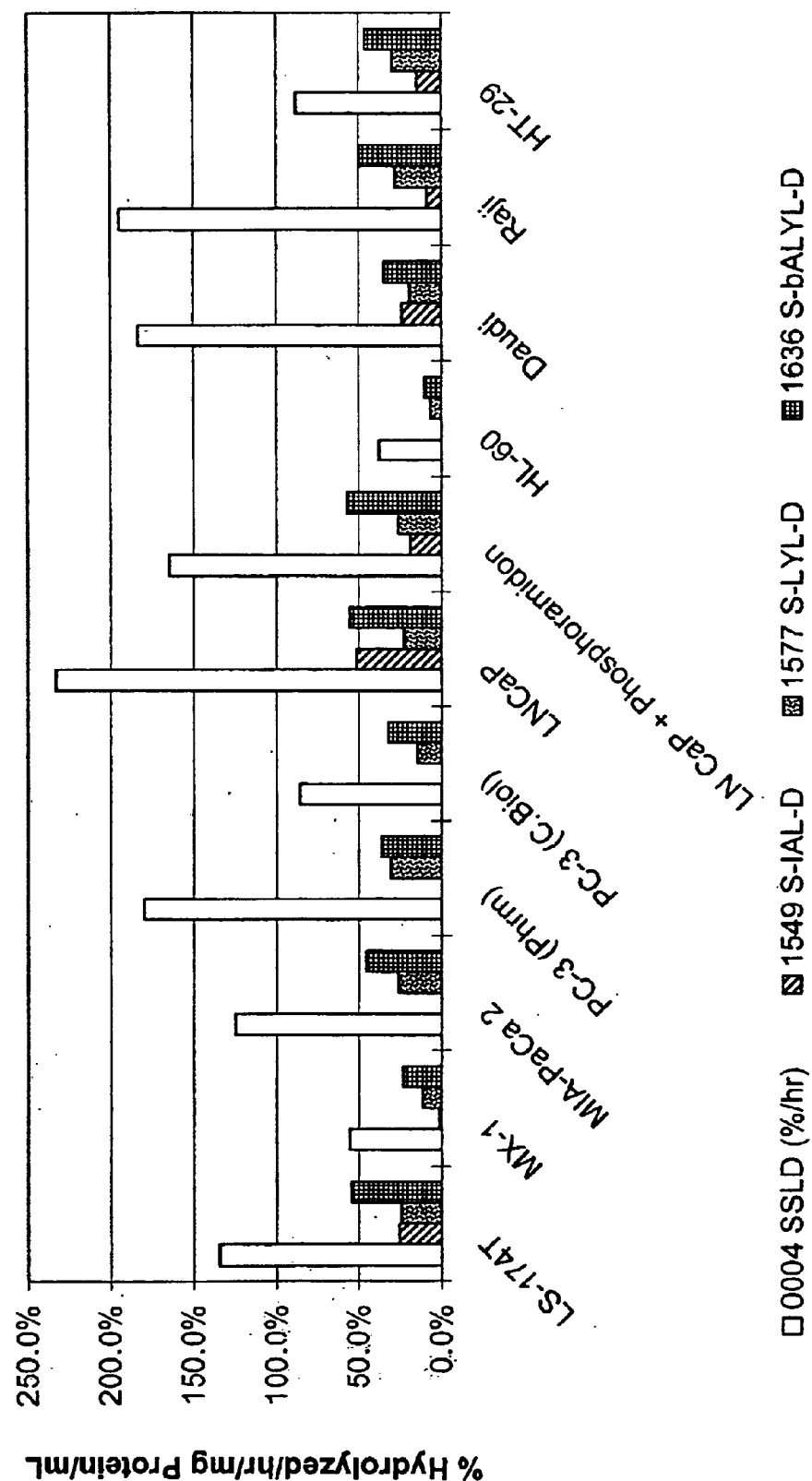
FIG. 12 is a table of specific hydrolysis rates of Suc-βAla-Leu-Ala-Leu-Dox (SEQ ID NO: 41), Suc-Ile-Ala-Leu-Dox (SEQ ID NO: 42), Suc-Leu-Tyr-Leu-Dox (SEQ ID NO: 43, and Suc-βAla-Leu-Tyr-Leu-Dox (SEQ ID NO: 44) by homogenates of various cultured human cell lines.

Various cultured human cell pellets were homogenized in a pH 7.2 100 mM HEPES buffer and the homogenate was incubated for up to 1 hr at 37° C. with 12.5 µg/mL of Suc-βAla-Leu-Ala-Leu-Dox SEQ ID NO: 41, Suc-Ile-Ala-Leu-Dox SEQ ID NO: 42, Suc-Leu-Tyr-Leu-Dox SEQ ID NO: 43, Suc-βAla-Leu-Tyr-Leu-Dox SEQ ID NO: 44. In addition, 1 μM phosphoramidon, a CD10 inhibitor was included in incubations with LNCaP cell homogenate. To estimate specific activity protein content was estimated in the soluble portion of the homogenates. Results expressed as protein specific activity (FIG. 12) indicate that LNCaP cells which are known to contain CD10 show the greatest Suc-Ile-Ala-Leu-Dox SEQ ID NO: 42 hydrolyzing activity. This activity is inhibited by phosphoramidon. PC-3 cells which do not express CD10 hydrolyze the other three substrates but not Suc-Ile-Ala-Leu-Dox SEQ ID NO: 42.

Figure 13:
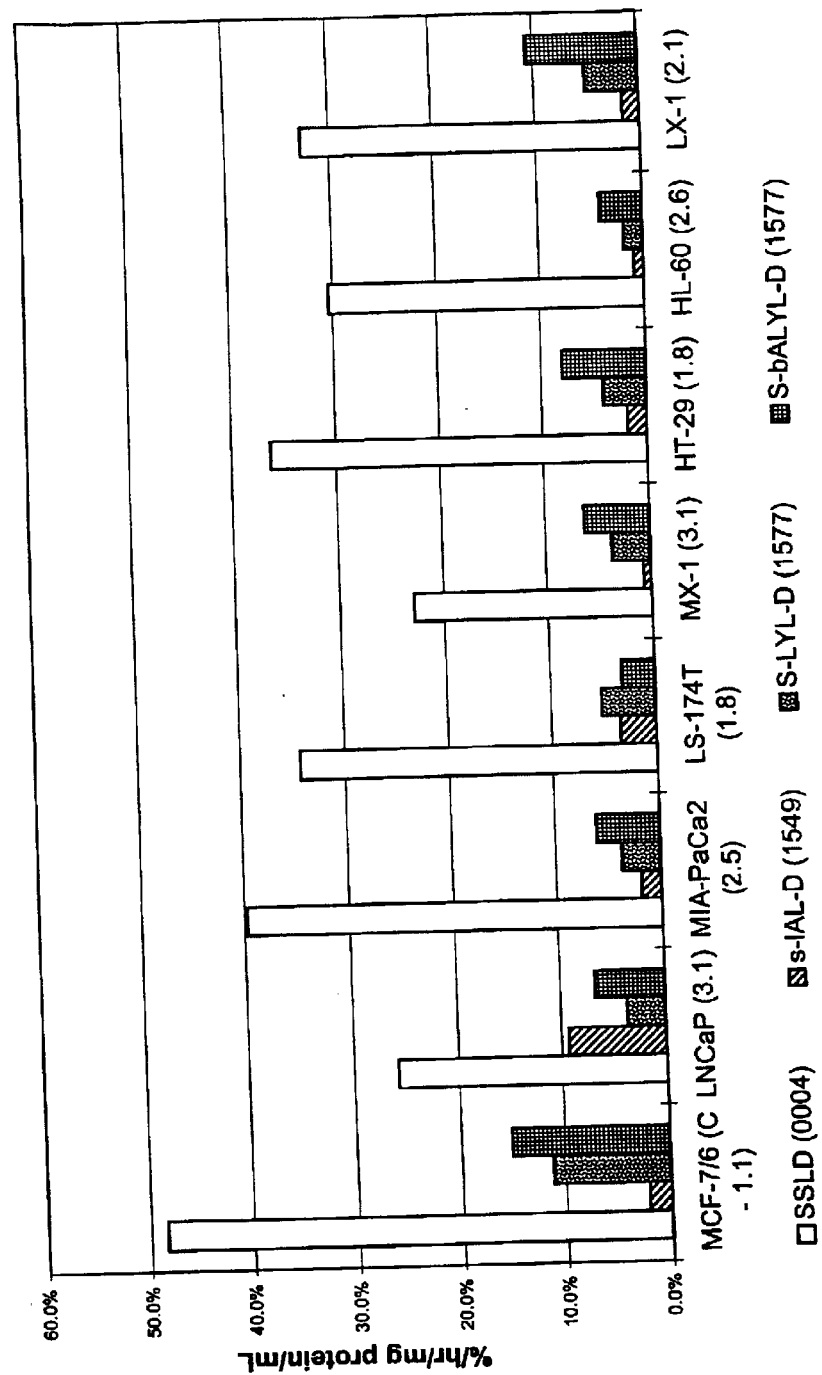
FIG. 13 is a table of specific hydrolysis rates Suc-βAla-Leu-Ala-Leu-Dox (SEQ ID NO: 41), Suc-Ile-Ala-Leu-Dox (SEQ ID NO: 42), Suc-Leu-Tyr-Leu-Dox (SEQ ID NO: 43), and Suc-βAla-Leu-Tyr-Leu-Dox (SEQ ID NO: 44) by homogenates of various xenograft tissues.

Mouse tumor xenografts from various sources were surgically removed, homogenized in a pH 7.2 100 mM HEPES buffer and incubated for up to 1 hr at 37° C. with 12.5 μg/mL Suc-βAla-Leu-Ala-Leu-Dox SEQ ID NO: 41, Suc-βAla-Ile-Ala-Leu-Dox SEQ ID NO: 39, Suc-Ile-Ala-Leu-Dox SEQ ID NO: 42 and Suc-Leu-Tyr-Leu-Dox SEQ ID NO: 43. Soluble protein was measured and results are reported as protein specific activity. The results, illustrated in FIG. 13, indicate the LNCaP cells contain the highest Suc-Ile-Ala-Leu-Dox SEQ ID NO: 42 hydrolyzing activity while HL-60 cells show no Suc-Ile-Ala-Leu-Dox SEQ ID NO: 42 hydrolyzing activity.

Example 2

Hydrolysis by Purified CD10

Equal amounts of purified Porcine Kidney CD10 (Elastin Products Company) were incubated with 12.5 μg/mL of various peptidyl doxorubicin compounds for up to 10 hr at 37° C. in pH 7.4 50 mM Tris HCl, 150 mM NaCl, 0.1% Triton X-100. Reaction products were analyzed by HPLC with fluorescence detection. Rates were essentially linear over the incubation period. The observed product was Leu-doxorubicin. Table 1 provides the percent of each test compound that was hydrolyzed over the ten hour period. Further these results are expressed relative to a standard test compound, Suc-βAla-Leu-Ala-Leu-Dox SEQ ID NO: 41.

TABLE 1

Hydrolysis by CD10

| Substrate | % hydrolysis/10 hr | Fraction hydrolyzed relative to standard |
|---|---|---|
| Suc-βAla-Leu-Ala-Leu-Dox SEQ ID NO: 41 | 10.9 | 1.0 |
| Suc-Ile-Ala-Leu-Dox SEQ ID NO: 42 | 12.5 | 1.1 |
| Suc-βAla-Ile-Ala-Leu-Dox SEQ ID NO: 39 | 22.1 | 2.0 |
| Suc-Leu-Tyr-Leu-Dox SEQ ID NO: 43 | 0 | 0 |
| Suc-βAla-Leu-Tyr-Leu-Dox SEQ ID NO: 44 | 0 | 0 |
| Suc-Leu-Ala-Leu-Dox SEQ ID NO: 45 | 8.3 | 0.75 |
| Suc-Met-Ala-Leu-Dox SEQ ID NO: 73 | 37.7 | 3.5 |
| Suc-Leu-Ala-Gly-Dox SEQ ID NO: 46 | 0 | 0 |

Example 3

The Effect of the Agent Attached to the Peptide on Cleavage by CD10

To test the CD10-catalyzed rate effect of the structure at the "toxin" position of the prodrug, the hydrolytic rate of Suc-βAla-Leu-Ala-Leu-Dox SEQ ID NO: 41 was compared to that of the analog where para nitroanilide (pNA) is substituted for doxorubicin, i.e., Suc-βAla-Leu-Ala-Leu-pNA SEQ ID NO: 75. Porcine kidney CD10 (Elastin Products Company) was incubated with the two substrates under identical conditions (37° C., pH 7.4, 50 mM Tris HCl, 150 mM NaCl, 0.01% Triton X-100) and the rate of release of Leu-Dox was compared to the rate of release of Leu-pNA. The results indicated that Suc-βAla-Leu-Ala-Leu-pNA SEQ ID NO: 75 is 590 times more rapidly cleaved than Suc-βAla-Leu-Ala-Leu-Dox SEQ ID NO: 41. This indicates that the structure (or attachment site) of the toxin in these tumor-activated prodrug compounds may influence the rate of cleavage.

Example 4

Screening of Potential Prodrugs

Prodrug compounds which are not cleaved by trouase or Thimet oligopeptidase but are cleaved by CD10 are preferred manifestations of this invention. Thus, screening of compounds for the lack of cleavability by trouase is preferred. Three different preparations of carcinoma cell trouase were used to screen various test compounds. These three preparations were as follows:

(a) MCF 7/6 (breast carcinoma) cell homogenate (b) MCF 7/6 (breast carcinoma) conditioned media, and (c) HeLa (cervical carcinoma) cell extract anion exchange fraction pool.

a. Preparation of MCF 7/6 Cell Homogenate

MCF 7/6 cells were grown to confluence in a serum free medium containing DMEM:F12 (1:1), 50 mg/L bovine serum albumin, ITS-X (10 mg/L insulin, 5.5 mg/L transferrin, 6.7 μg/L Na selenite, 2 mg/L ethanolamine), and Lipid Concentrate (Gibco #21900–030) 100 mL of cells were harvested by centrifugation at 4° C. 10,000×g, for 20 min and decanting the supernatant. The pellet was resuspended in 2 mL phosphate buffered saline (Gibco) and centrifuged at 18,000×g for 10 min. After decanting the supernatant, the cells (approximately 300 μL wet) were homogenized by grinding in 1.7 mL 10 mM pH 7.2 HEPES buffer (sodium salt). The homogenate was centrifuged at 18,000×g at 4° C. for 5 min and the supernatant was aliquoted and stored at ≦−20° C. for subsequent use in the compound screen.

b. Preparation of MCF 7/6 Conditioned Media

MCF 7/6 cells were grown to confluence in DMEM/F12 (1:1) medium containing 10% fetal bovine serum, 0.05% (w/v) L-glutamine, 250 IU/mL penicillin, and 100 μg/mL streptomycin. Cells were then washed twice with phosphate buffered saline and incubated 24 hr at 5% $CO_2$, 37° C., in DMEM/F12 (1:1), 0.02% BSA, ITS-X (10 mg/L insulin, 5.5 mg/L transferrin, 6.7 μg/L Na selenite, 2 mg/L ethanolamine). The conditioned media was then decanted and, using a stirred cell apparatus with a YM10 (10,000 MW cutoff) ultrafiltration membrane (Millipore), exchanged once with 10 mM HEPES buffer, pH 7.2 and concentrated twenty-fold. This solution was stored in aliquots at −20° C. for use in the compound screen.

c. Preparation of HeLa Cell Anion Exchange Fraction Pool

Thirty billion commercially produced HeLa Cells (human cervical carcinoma, Computer Cell Culture Center, Seneffe, Belgium) were homogenized with a sonicator and with a Dounce homogenizer in 108 mL of aqueous lysis solution. The lysis solution contained 0.02% w/v Triton X-100, 0.04% w/v sodium azide, and a cocktail of protease inhibitors (2 tablets/50 mL Complete™, EDTA-free tablets, Roche Molecular Biochemicals). The cell homogenate was centrifuged 30 minutes at 4° C. at 5000×g and the pellet was homogenized in a second 108 mL of lysis solution using a Dounce homogenizer and centrifuged as before. The supernatants were combined and centrifuiged for 90 min at 145,000×g at 4° C.

A portion of the ultracentrifugation supernatant was diluted 2-fold with a 20 mM triethanolamine-HCl pH 7.2 buffer containing 0.01% (w/v) Triton X-100 and 0.02% (w/v) sodium azide (equilibration buffer). Thirty mL of the resulting solution, corresponding to approximately 180 mg of protein, was loaded at 4° C. on a 2.6×9.4 cm Source™15Q (Amersham Pharmacia Biotech) low pressure anion exchange chromatography column (1 ml/minute). The column was then washed with 250 ml of the equilibration buffer at a flow rate of 1 mL/minute. Proteins were eluted in a NaCl linear concentration gradient (0–0.5 M in the equilibration buffer, total volume of the gradient was 1000 ml) at a flow rate of 3 ml/minute. Two-minute fractions were collected and used for enzyme activity determination using βAla-Leu-Ala-Leu-Dox SEQ ID NO: 76 as the substrate. Its transformation into Ala-Leu-Dox was quantified by reverse phase high performance liquid chromatography utilizing fluorescence detection of the anthracycline moiety. The fractions containing the highest activity levels were pooled (fractions #43–46; ~0.13 M NaCl), supplemented with protease inhibitors (Complete™, EDTA-free tablets, Roche Molecular Biochemicals), and stored as aliquots at −80° C.

d. Cleavage Assay

Test compounds were incubated for 2 hr at 37° C. at a concentration of 12.5 μg/mL with each of the three different preparations of carcinoma cell enzyme. Following incubation, three volumes of acetonitrile were added to stop the reaction and remove protein from the mixture. The sample was centrifuged at 18,000 g for 5 minutes and 100 μL of supernatant was mixed with 300 μL of water prior to analysis by HPLC. For HPLC analysis, 50 μL of sample was injected on a 4.6×50 mm 2μ TSK Super-ODS chromatography column at 40° C. and eluted with a 3 minute linear gradient from 26% to 68% acetonitrile in aqueous 20 mM ammonium acetate pH 4.5 buffer at 2 mL/min. Detection was by fluorescence using an excitation wavelength of 235 nm and an emission wavelength of 560 nm.

Test compounds that were not cleaved (<5% cleavage −2 Hr) by the enzyme preparations under the given conditions are shown in Table 2 below. With few exceptions, results for carcinoma cell enzyme cleavage were identical for a partially purified fraction from HeLa cells, MFC 7/6 cell homogenate, and MCF 7/6 conditioned media.

TABLE 2

| No: | Stabilizing Group | (AA) | (AA) | (AA) | (AA) | Therapeutic Compound |
|---|---|---|---|---|---|---|
| 1 | Suc | βAla | Ile | Ala | Phe | Dnr SEQ ID NO: 77 |
| 2 | Suc | βAla | Ile | Ala | Ile | Dnr SEQ ID NO: 78 |
| 3 | Suc | Tic | Ile | Ala | Leu | Dnr SEQ ID NO: 79 |
| 4 | Suc | Thi | Ile | Ala | Leu | Dnr SEQ ID NO: 80 |
| 5 | Suc | Nal | Ile | Ala | Leu | Dnr SEQ ID NO: 81 |
| 6 | Suc | βAla | Ile | Ala | Leu | Dnr SEQ ID NO: 82 |
| 7 | Suc | Amb | Ile | Ala | Leu | Dnr SEQ ID NO: 83 |
| 8 | Suc | Aib | Ile | Ala | Leu | Dnr SEQ ID NO: 84 |
| 9 | Suc | βAla | Ile | Ala | Leu | Dox SEQ ID NO: 85 |
| 10 | Suc | Thi | Ile | Aib | Leu | Dnr SEQ IQ NO: 86 |
| 11 | Suc | Nal | Ile | Aib | Leu | Dnr SEQ ID NO: 87 |
| 12 | Suc | βAla | Ile | Aib | Leu | Dnr SEQ ID NO: 88 |
| 13 | Suc | Amb | Ile | Aib | Leu | Dox SEQ ID NO: 89 |
| 14 | Suc | Aib | Ile | Aib | Leu | Dnr SEQ ID NO: 90 |
| 15 | Suc | βAla | Ile | Gly | Phe | Dnr SEQ ID NO: 91 |
| 16 | Suc | βAla | Ile | Gly | Ile | Dnr SEQ IQ NO: 92 |
| 17 | Suc | Tic | Ile | Gly | Leu | Dnr SEQ ID NO: 93 |
| 18 | Suc | Thi | Ile | Gly | Leu | Dnr SEQ ID NO: 94 |
| 19 | Suc | Nal | Ile | Gly | Leu | Dnr SEQ ID NO: 95 |
| 20 | Suc | βAla | Ile | Gly | Leu | Dnr SEQ ID NO: 96 |
| 21 | Suc | Amb | Ile | Gly | Leu | Dnr SEQ ID NO: 97 |
| 22 | Suc | Aib | Ile | Gly | Leu | Dnr SEQ ID NO: 98 |
| 23 | Suc | βAla | Ile | Thr | Ile | Dnr SEQ ID NO: 99 |
| 24 | Suc | βAla | Ile | Tyr | Ile | Dnr SEQ ID NO: 100 |
| 25 | Suc | βAla | Ile | Tyr | Leu | Dnr SEQ ID NO: 101 |
| 26 | Suc | βAla | Ile | Tyr | Gly | Dox SEQ ID NO: 102 |
| 27 | Suc | Ø | Ile | Ala | Leu | Dox SEQ ID NO: 103 |
| 28 | Suc | Ø | Ile | N(Me)Ala | Leu | Dox SEQ ID NO: 104 |

Ø = not present

Example 5

CD10 Expression on Cell Lines

CD10 (CD10) is widely expressed in a number of tumor types (Chu and Arber, Am. J. Clin. Pathol. 113:374–382 (2000)) including a high proportion (61%) of prostate tumors. CD10 has also been shown to be expressed on some human prostate tumor-derived cell lines cultured in vitro. It was therefore of interest to determine whether peptide prodrugs of the invention were cytotoxic to tumor lines derived from prostate, as well as from other tumor types, which express CD10 on their surface. The prostate tumor line, LNCaP expresses high levels of CD10 (Krongrad, et al., Urol. Res. 25:113–116 (1997); Liu, Cancer Res. 60:3429–3434 (2000)). Several prostate tumor lines in culture also express another well-characterized cell-surface associated endo-protease, Prostate Specific Antigen (PSA). The prostate cell lines described in Table 3 were obtained from the American Type Culture Collection (ATCC) and screened for CD10 expression by flow cytometry using CD10-specific monoclonal antibody (Caltag Clone 5–1 B4).

TABLE 3

| Cell Line | ATCC# | PSA | CD10 |
|---|---|---|---|
| LNCaP | CRL-1740 | + | + |
| PC-3 | CRL-1435 | − | − |
| 22Rv1 | CRL-2505 | + | − |

Figure 14:
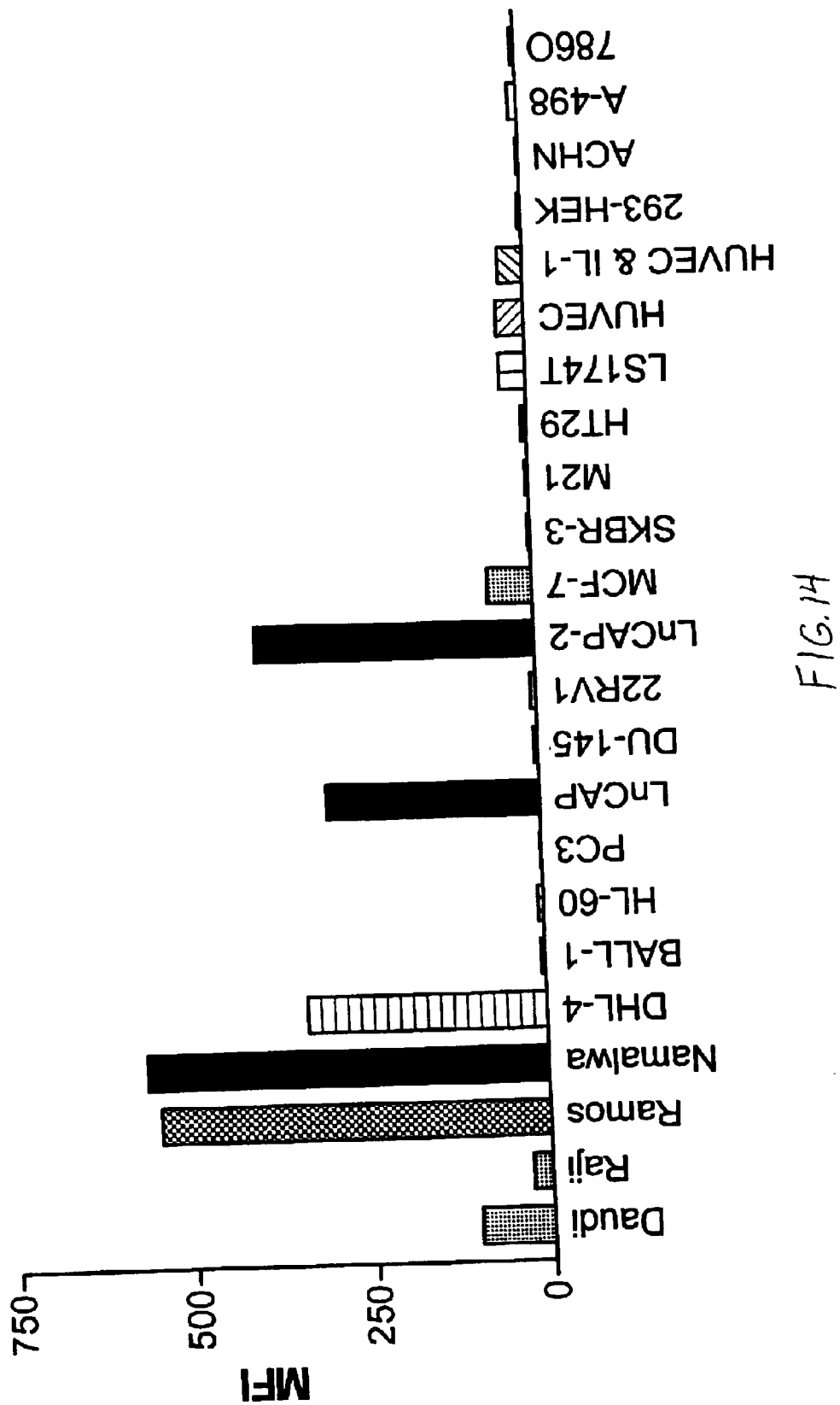
FIG. 14 shows the expression of CD10 as determined by flow cytometric analysis for a panel of cell lines.

Flow cytometric analysis was done with a panel of cell lines to determine the expression of CD10. FIG. 14 shows that CD10 is also expressed at high levels on some B-cell lymphoma lines, which do not express PSA. Such B-cell lines include Ramos and Namalwa cells. LNCaP prostate carcinoma cells, were also shown to express high levels of CD10 while HT29, PC-3 and BALL-1 cells did not express detectable levels of this antigen and served as a negative control for subsequent studies. Low expression of CD10 was found on colon carcinoma LS 174T and breast carcinoma, MCF-7.

Example 6

Tumor-Activated Prodrug Activity on LNCaP, HT-29 and PC-3 Cells

Adherent cells, LNCaP (prostate carcinoma), HT-29 (colon carcinoma) and PC-3 (prostate carcinoma), were cultured in DMEM media containing 10% heat inactivated fetal calf serum (FCS). On the day of the study the cells were detached from the plate with a trypsin solution. The collected cells were washed and resuspended at a concentration of $0.25 \times 10^6$ cells/ml in DMEM containing 10% FCS. 100 μl of cell suspension were added to 96 well plates and the plates were incubated for 3 hours to allow the cells to adhere. Following this incubation, serial dilutions (3-fold increments) of doxorubicin or test compounds were made and 100 μl of compounds were added per well. The plates were then incubated for 24 hours, pulsed with 10 μl of a 100 μCi/ml $^3$H-thymidine and incubated for an additional 24 hours (total incubation time 48 hours). The plates were harvested using a 96 well Harvester (Packard Instruments) and counted on a Packard Top Count Counter. Four parameter logistic curves were fitted to the $^3$H-thymidine incorporation as a function of drug molarity using Prism software to determine $IC_{50}$ values.

The $IC_{50}$ of the positive control, Doxorubicin, was 0.02–0.08 μM in the cell lines used. The compounds, which showed the highest degree of selectivity for LNCaP cells, were Suc-βAla-Ile-Ala-Leu-Dox SEQ ID NO: 39, Suc-Ile-NMeAla-Leu-Dox SEQ ID NO: 105 and Suc-Ile-Ala-Leu-Dox SEQ ID NO: 42 (Table 4). The common features of these three prodrugs are that they contain an isoleucine in amino acid position 3. Compounds such as Suc-βAla-Leu-Ala-Leu-Dox SEQ ID NO: 41, Suc-Leu-Ala-Leu-Dox SEQ ID NO: 45 and Suc-Leu-NMe-Ala-Leu-Dox SEQ ID NO: 106, which contain a leucine in amino acid position 3, also show selectivity though the extent of selectivity is less than that of the isoleucine analogs.

TABLE 4

Activity on LNCaP, HT-29 and PC-3 cells

| Compound | IC50 (μM) | | | Ratio |
| --- | --- | --- | --- | --- |
| | LNCAP | HT29 | PC-3 | PC-3:LNCaP |
| DOX | 0.016 | 0.052 | 0.075 | 5 |
| Suc-βAla-Ile-Ala-Leu-Dox SEQ ID NO: 39 | 0.19 | 38 | 57 | 300 |
| Suc-Ile-NMeAla-Leu-Dox SEQ ID NO: 105 | 0.51 | 36 | 66 | 129 |
| Suc-βAla-Leu-Ala-Leu-Dox SEQ ID NO: 41 | 0.87 | 19 | 28 | 32 |
| Suc-Leu-Ala-Leu-Dox SEQ ID NO: 45 | 1.0 | 36 | 50 | 50 |
| Suc-Ile-Ala-Leu-Dox SEQ ID NO: 42 | 1.1 | 47 | 88 | 83 |
| Suc-Leu-NMeAla-Leu-Dox SEQ ID NO: 106 | 1.2 | 24 | 45 | 37 |
| Suc-Ile-Pro-Leu-Dox SEQ ID NO: 107 | 2.0 | 44 | 106 | 53 |
| Suc-Leu-Tyr-Leu-Dox SEQ ID NO: 43 | 9.4 | 42 | 51 | 5 |
| Suc-βAla-Leu-Tyr-Leu-Dox SEQ ID NO: 44 | 14 | 23 | 46 | 3 |
| Suc-Leu-Ala-Gly-Dox SEQ ID NO: 46 | 15 | 32 | 39 | 3 |
| Suc-Leu-Tyr-Gly-Dox SEQ ID NO: 108 | 15 | 25 | 64 | 4 |

Example 7

Tumor-Activated Prodrug Activity on Ball-1, Ramos and Namalwa Cells

In addition to LNCaP, a number of B-cell lines, such as Ramos and Namalwa cells express CD10 ($CD10^{pos}$ cells). However, another B-cell line, BALL-1 cells, do not express CD10 and serve as a CD10 negative B-cell line ($CD10^{neg}$ cells).

Suspension cells, BALL-1, Ramos and Namalwa cells were cultured in RPMI media containing 10% heat inactivated fetal calf serum (FC S). On the day of the study, the cells were collected, washed and resuspended at a concentration of $0.5 \times 10^6$ cells/ml in RPMI containing 10% FCS. 100 μl of cell suspension was added to 96 well plates. Serial dilutions (3-fold increments) of doxorubicin or test compounds were made and 100 μl of compounds were added per well. Finally 10 μl of a 100 μCi/ml $^3$H-thymidine was added per well and the plates were incubated for 24 hours. The plates were harvested using a 96 well Harvester (Packard Instruments) and counted on a Packard Top Count counter. Four parameter logistic curves were fitted to the $^3$H-thymidine incorporation as a function of drug molarity using Prism software to determine $IC_{50}$ values.

The largest selectivity was seen with Suc-βAla-Ile-Ala-Leu-Dox SEQ ID NO: 39, which showed 120–172 fold selectivity for Ramos and Namalwa cells, respectively as compared to $CD10^{neg}$ BALL-1 cells (Table 5). The second most selective analog was Suc-Leu-Ala-Leu-Dox SEQ ID NO: 45 with an ~30–35 fold difference between $CD10^{pos}$ and $CD10^{neg}$ cells.

TABLE 5

Activity on BALL ($CD10^{neg}$)-1, Ramos ($CD10^{pos}$) & Namalwa ($CD10^{pos}$) cells

| Compound | IC50 (μM) | | | Ratio | |
| --- | --- | --- | --- | --- | --- |
| | Ball-1 | Ramos | Namalwa | Ball-1: Ramos | Ball-1: Namalwa |
| DOX | 0.02 | 0.01 | 0.01 | 1 | 2 |
| Suc-βAla-Ile-Ala-Leu-Dox SEQ ID NO: 39 | 50.00 | 0.42 | 0.29 | 120 | 172 |
| Suc-Leu-Ala-Leu-Dox SEQ ID NO: 45 | 78.67 | 2.63 | 2.27 | 30 | 35 |
| Suc-Ile-Ala-Leu-Dox SEQ ID NO: 42 | 26.00 | 6.43 | 6.47 | 4 | 4 |
| Suc-βAla-Leu-Ala-Leu-Dox SEQ ID NO: 41 | 17.00 | 6.93 | 5.77 | 2 | 3 |
| Suc-Leu-Tyr-Leu-Dox SEQ ID NO: 43 | 17.00 | 20.00 | 14.00 | 1 | 1 |
| Suc-Leu-Ala-Gly-Dox SEQ ID NO: 46 | 23.33 | 22.67 | 17.33 | 1 | 1 |

Example 8

Adherent cells, LNCaP (prostate carcinoma), PC-3 (prostate carcinoma) and 22 RV1 (prostate carcinoma), were cultured in DMEM media containing 10% heat inactivated fetal calf serum (FCS). On the day of the study the cells were detached from the plate with a trypsin solution. The collected cells were washed and resuspended at a concentration of $0.25 \times 10^6$ cells/ml in DMEM containing 10% FCS. 100 μl of cell suspension were added to 96 well plates and the plates were incubated for 3 hours to allow the cells to adhere. Following this incubation, serial dilutions (3-fold increments) of doxorubicin or test compounds were made and 100 μl of compounds were added per well. The plates were then incubated for 24 hours, pulsed with 10 μl of a 100 μCi/ml $^3$H-thymidine and incubated for an additional 24 hours (total incubation time 48 hours). The plates were harvested using a 96 well Harvester (Packard Instruments)

and counted on a Packard Top Count Counter. Four parameter logistic curves were fitted to the $^3$H-thymidine incorporation as a function of drug molarity using Prism software to determine IC$_{50}$ values.

TABLE 6

|  | LnCAP<br>CD10$^+$PSA$^+$ | PC-3<br>CD10$^-$PSA$^-$ | 22RV1<br>CD10$^-$PSA$^+$ |
|---|---|---|---|
|  | IC$_{50}$ (mM) | | |
| Dox | 0.02 | 0.04 | 0.03 |
| Suc-βAla-Ile-Ala-Leu-Dox<br>SEQ ID NO: 39 | 0.15 | 190.00 | 10.80 |
| Suc-Ile-Ala-Leu-Dox<br>SEQ ID NO: 42 | 0.17 | 48.00 | 14.00 |
| Suc-Leu-Ala-Gly-Dox<br>SEQ ID NO: 46 | 28.50 | 57.00 | 34.50 |

Table 6 exemplifies that cells which are PSA positive and CD10 negative such as 22RV1 do not readily cleave Suc-βAla-Ile-Ala-Leu-Dox SEQ ID NO: 39 or Suc-Ile-Ala-Leu-Dox SEQ ID NO: 42. The data suggest that CD10 is responsible for cleavage of these compounds and not PSA.

Example 9

Figure 15:
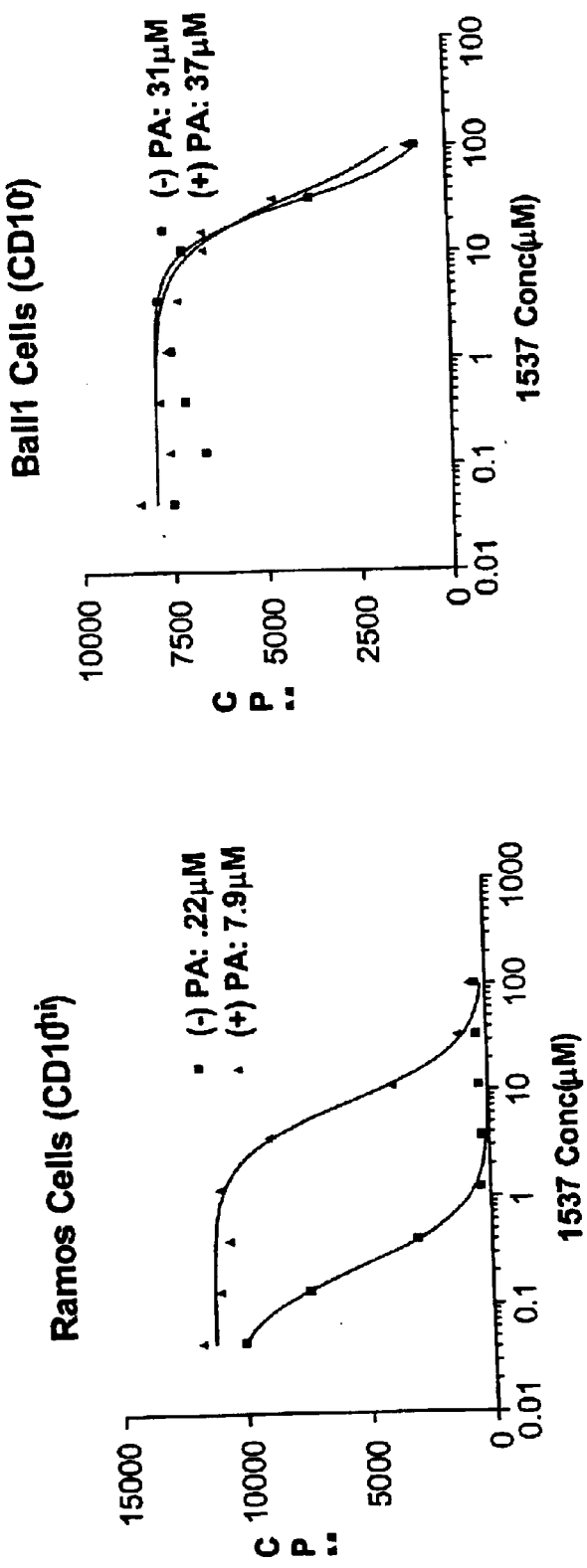
FIG. 15 is a graph of some titration curves of the cleavage of Suc-βAla-Ile-Ala-Leu-Dox (SEQ ID NO: 39) by CD10 in the absence or presence of 300 nM phosphoramidon.

Inhibition of CD10 Decreases the Potency of Suc-βAla-Ile-Ala-Leu-Dox (SEQ ID NO: 39) for Ramos and LNCaP cells, but not Ball-1 Cells The effect of two known inhibitors of CD10 on prodrug activity in Ramos, LNCaP and Ball-1 cells was evaluated. The IC$_{50}$ of Suc-βAla-Ile-Ala-Leu-Dox SEQ ID NO: 39 was determined in the presence of increasing concentration of the CD10 inhibitors, phosphoramidon and thiorphan. Increasing the concentration of phosphoramidon resulted in a loss of potency of Suc-βAla-Ile-Ala-Leu-Dox SEQ ID NO: 39 with Ramos and LNCaP cells whereas BALL-1 cells were not affected (Table 7). Likewise the IC$_{50}$ of Suc-βAla-Leu-Ala-Leu-Dox SEQ ID NO: 41 was shifted 7-fold on LNCaP cells treated with 100 nM of phosphoramidon (data not shown). FIG. 15 shows an example of some titration curves with Suc-βAla-Ile-Ala-Leu-Dox SEQ ID NO: 39 in the absence or presence of 300 nM phosphoramidon.

TABLE 7

Inhibition by phosphoramidon in Ball-1, Ramos and LNCaP cells

|  | IC50 (μM) | | |
|---|---|---|---|
| Phosphoramidon (nM) | CD10$^{neg}$<br>Ball-1 | CD10$^{pos}$<br>Ramos | CD10$^{pos}$<br>LNCaP |
| 0 | 22 | 0.51 | 0.24 |
| 30 | 20 | 2.1 | 1.3 |
| 100 | 21 | 5.3 | 3.3 |
| 300 | 24 | 8.1 | 7.7 |
| 1000 | 25 | 9.7 | 11.3 |
| 3000 | 26 | 10.5 | 15.4 |

Thiorphan, the second CD10 inhibitor, also shifts the IC$_{50}$ of Suc-βAla-Ile-Ala-Leu-Dox SEQ ID NO: 39 on CD10+ cells (Table 8). However, thiorphan showed more inhibitory activity with LNCaP as compared to Ramos cells.

TABLE 8

Inhibition by thiorphan in Ramos (CD10$^{pos}$) and LNCaP (CD10$^{pos}$) cells

|  | IC50 (μM) | |
|---|---|---|
| DL-Thiorphan | CD10$^{pos}$<br>Ramos | CD10$^{pos}$<br>LNCaP |
| 0 | 0.25 | 0.51 |
| 30 | 0.27 | 2.1 |
| 100 | 0.31 | 5.3 |
| 300 | 0.28 | 8.1 |
| 1000 | 0.44 | 9.7 |
| 3000 | 1.1 | 10.5 |

Example 10

Detecting CD10 Associated with a Target Cell

Immunohistochemical analysis was performed on samples of LNCaP and PC3 tissue, taken from xenografts grown in nude mice then fixed in formalin. Tissue sections were prepared and immunostained with either an antibody specific for CD10 or an isotype-matched negative control, then counterstained with hemotoxylin. The LNCap samples showed intense cell surface membrane-associated pattern of staining by the CD10-specific antibody, which was relatively evenly distributed around the periphery of all cells in the tumor tissue sample of all LNCaP cells. In contrast, no immunoreactivity was observed on PC3 tissue. Compounds cleavable by CD10, but not TOP, such as Suc-βAla-Ile-Ala-Leu-Dox SEQ ID NO: 39, were effective in inhibiting the growth of LNCaP tumors in mice, whereas they were not active against PC3 cells (see Example 6). Thus CD10 immunohistochemistry is useful in selecting tumors responsive to CD10 cleavable prodrugs.

Example 11

Suc-Ile-Ala-Leu-Dox (SEQ ID NO:42) is Well-Tolerated in Healthy Mice

Suc-Ile-Ala-Leu-Dox SEQ ID NO: 42, an exemplary tripeptide prodrug of the invention, is well tolerated in mice. In a single dose Maximum Tolerated Dose (MTD) study, groups of five normal mice were administered intravenous bolus doses of Suc-Ile-Ala-Leu-Dox SEQ ID NO: 42. The mice were observed daily for 28 days and body weights measured twice weekly. Dose levels tested were 0, 23, 47, 70, 93 and 117 mg/kg, equivalent to 0, 14, 28, 42, 56, and 70 mg of doxorubicin/kg respectively. There was no acute toxicity, and the only sign of toxicity observed was a decrease in group mean body weight for the highest dose group, which was lower than the vehicle control group throughout the study. However, there were no mortalities, and no animals exhibited morbidity. The 28-day single-dose Maximum Tolerated Dose (MTD) of Suc-Ile-Ala-Leu-Dox SEQ ID NO: 42 was not attained in this experiment, and is therefore greater than the highest dose tested, 117 mg/kg. This MTD (equivalent to 66 mg of doxorubicin/kg) is at least 16-fold higher than that of doxorubicin alone, which results in mortality following doses greater than 4 mg/kg.

Example 12

Suc-βAla-Ile-Ala-Leu-Dox (SEQ ID NO:39) is Well Tolerated in Healthy Mice

Suc-βAla-Ile-Ala-Leu-Dox SEQ ID NO: 39, an exemplary tetrapeptide prodrug of the invention, is well tolerated in mice. In a single dose Maximum Tolerated Dose (MTD) study, groups of five normal mice were administered intravenous bolus doses of Suc-βAla-Ile-Ala-Leu-Dox SEQ ID NO: 39. The mice were observed daily for 28 days and body weights measured twice weekly. Dose levels tested were 0, 25, 50, 75, 100 and 125 mg/kg, equivalent to 0, 14, 28, 42, 56, and 70 mg of doxorubicin/kg respectively. No acute toxicity was observed following administration. Toxicity, including paralysis and significant body weight loss (>20% of their initial weight), was observed in the two highest dose groups. On Day 14, four animals in the 125 mg/kg dose group were euthanized due to treatment-related toxicity. On Day 21, two animals in the next highest dose group, i.e., 100 mg/kg were similarly euthanized. There was no morbidity observed in the next dose-group (75 mg/kg) and the group-mean-body-weight increased during the study.

Based on survival at Day 28, the single-dose MTD value for Suc-βAla-Ile-Ala-Leu-Dox SEQ ID NO: 39 was estimated to be 75 mg/kg (equivalent to a dose of 40 mg doxorubicin/kg). Thus, the MTD was approximately 10-fold higher than the MTD of doxorubicin alone, estimated to be 4 mg/kg based on the standard safe efficacious dose (4–8 mg/kg).

Example 13

Suc-βAla-Leu-Ala-Leu-Dox (SEQ ID NO:41) is Better Tolerated in vivo than Doxorubicin Suc-βAla-Leu-Ala-Leu-Dox SEQ ID NO: 41, an exemplary tetrapeptide prodrug of the invention, is well tolerated in mice. In a second single dose Maximum Tolerated Dose (SD-MTD) study, groups of five normal ICR mice were administered intravenous bolus doses of Suc-βAla-Leu-Ala-Leu-Dox SEQ ID NO: 41. The mice were observed daily for 49 days and body weights measured twice weekly. Dose levels tested were 0, 50, 75 or 100 mg/kg, equivalent to 0, 28, 42 or 56 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight) was observed in the 75 and 100 mg/kg dose groups. By Day 35 mortality was observed in 40% of the 75 mg/kg dose group. Based on survival and lack of signs of toxicity at Day 49, the SD-MTD for Suc-βAla-Leu-Ala-Leu-Dox SEQ ID NO: 41 was determined to be 50 mg/kg (equivalent to 28 mg/kg of doxorubicin). This dose was very well tolerated and no adverse effects were observed. Therefore, the SD-MTD was approximately 1.8-fold higher on a molar basis than the SD-MTD for doxorubicin alone (16 mg/kg). See Table 9. This is an approximate SD-MTD determination based on a range of doses at 14 mg/kg doxorubicin equivalents increments over the range tested.

TABLE 9

| Compound Name | SD-MTD (mg/kg) | SD-MTD (mg/kg Dox =) | SD-MTD Molar Ratio (Dox =) |
| --- | --- | --- | --- |
| Doxorubicin | 16 | 16 | 1 |
| Suc-βAla-Leu-Ala-Leu-Dox SEQ ID NO: 41 | 50 | 28 | 1.8 |

Example 14

Suc-Leu-Ala-Leu-Dox (SEQ ID NO:45) is Better Tolerated in vivo than Doxorubicin

Suc-Leu-Ala-Leu-Dox SEQ ID NO: 45, an exemplary tripeptide prodrug of the invention, is well tolerated in mice. In a second single dose Maximum Tolerated Dose (SD-MTD) study, groups of five normal ICR mice were administered intravenous bolus doses of Suc-Leu-Ala-Leu-Dox SEQ ID NO: 45. The mice were observed daily for 49 days and body weights measured twice weekly. Dose levels tested were 0, 47, 59, 71, 94, 117, 140 or 164 mg/kg, equivalent to 0, 28, 35, 42, 56, 70, 84 or 98 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight), was observed in the 94 mg/kg and higher dose groups. Based on survival and lack of signs of toxicity at Day 49, the SD-MTD for Suc-Leu-Ala-Leu-Dox SEQ ID NO: 45 was determined to be 71 mg/kg (equivalent to 42 mg/kg of doxorubicin). Therefore, the SD-MTD was approximately 2.6-fold higher on a molar basis than the SD-MTD for doxorubicin alone (16 mg/kg). See Table 10. This is an approximate SD-MTD determination based on a range of doses at 7 or 14 mg/kg doxorubicin equivalents increments over the range tested.

TABLE 10

| Compound Name | SD-MTD (mg/kg) | SD-MTD (mg/kg Dox =) | SD-MTD Molar Ratio (Dox =) |
| --- | --- | --- | --- |
| Doxorubicin | 16 | 16 | 1 |
| Sue-Leu-Ala-Leu-Dox SEQ ID NO: 45 | 71 | 42 | 2.6 |

Example 15

Suc-Ile-Ala-Leu-Dox (SEQ ID NO:42) is Better Tolerated in vivo than Doxorubicin

Suc-Ile-Ala-Leu-Dox SEQ ID NO: 42, an exemplary tripeptide prodrug of the invention, is well tolerated in mice. In a second single dose Maximum Tolerated Dose (SD-MTD) study, groups of five normal ICR mice were administered intravenously bolus doses of Suc-Ile-Ala-Leu-Dox SEQ ID NO: 42. The mice were observed daily for 49 days and body weights measured twice weekly. Dose levels tested were 0, 94, 117, 140 or 164 mg/kg, equivalent to 0, 56, 70, 84 or 98 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight), was observed in the highest dose groups. Signs of toxicity were partial hind end paralysis at 164 mg/kg by Day 14, weight loss at 140 mg/kg by Day 14 in one animal and at 117 mg/kg by Day 21 also in one animal. Based on survival and lack of signs of toxicity at Day 49, the SD-MTD for Suc-Ile-Ala-Leu-Dox SEQ ID NO: 42 was determined to be 94 mg/kg (equivalent to 56 mg/kg of doxorubicin), which is 3.5-fold higher on a molar basis than the SD-MTD for doxorubicin alone (16 mg/kg). See Table 11. This is an approximate SD-MTD determination based on a range of doses at 14 mg/kg doxorubicin equivalents increments over the range tested.

TABLE 11

| Compound Name | SD-MTD (mg/kg) | SD-MTD (mg/kg Dox =) | SD-MTD Molar Ratio (Dox =) |
|---|---|---|---|
| Doxorubicin | 16 | 16 | 1 |
| Suc-Ile-Ala-Leu-Dox SEQ ID NO: 42 | 94 | 58 | 3.5 |

Example 16

Suc-βAla-Ile-Ala-Leu-Dox (SEQ ID NO:39) is Better Tolerated in vivo than Doxorubicin Suc-βAla-Ile-Ala-Leu-Dox SEQ ID NO: 39, an exemplary tetrapeptide prodrug of the invention, is well tolerated in mice. In a second single dose Maximum Tolerated Dose (SD-MTD) study, groups of five normal ICR mice were administered intravenous bolus doses of Suc-βAla-Ile-Ala-Leu-Dox SEQ ID NO: 39. The mice were observed daily for 49 days and body weights measured twice weekly. Dose levels tested were 0, 50, 75 or 100 mg/kg, equivalent to 0, 28, 42 or 56 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight), was observed in the highest dose group. By Day 21, three animals in the 100 mg/kg dose were euthanized due to weight loss or paralysis. There was no morbidity or mortality observed in the 75 mg/kg dose group. Based on survival and lack of signs of toxicity at Day 49, the SD-MTD for Suc-βAla-Ile-Ala-Leu-Dox SEQ ID NO: 39 was determined to be 75 mg/kg (equivalent to 42 mg/kg of doxorubicin), which is 2.6-fold higher on a molar basis than the SD-MTD for doxorubicin alone (16 mg/kg). See Table 12. This is an approximate SD-MTD determination based on a range of doses at 14 mg/kg doxorubicin equivalents increments over the range tested.

TABLE 12

| Compound Name | SD-MTD (mg/kg) | SD-MTD (mg/kg Dox =) | SD-MTD Molar Ratio (Dox =) |
|---|---|---|---|
| Doxorubicin | 16 | 16 | 1 |
| Suc-βAla-Ile-Ala-Leu-Dox SEQ ID NO: 39 | 75 | 42 | 2.6 |

Example 17

Metabolism of Suc-Ile-Ala-Leu-Dox (SEQ ID NO:42)

The metabolism and clearance of Suc-Ile-Ala-Leu-Dox SEQ ID NO: 42 was studied in normal mice. The mice were administered Suc-Ile-Ala-Leu-Dox SEQ ID NO: 42 at a single intravenous bolus dose of 117 mg/kg. Plasma samples were obtained at 1 and 4 hours. Plasma samples of 100 µl were transferred to microcentrifuge tubes (1.5 mL) and an internal standard of daunorubicin (20 µL at 0.5 mg/ml) was added together with acetonitrile (400 µl). The tubes were capped and briefly vortexed followed by centrifugation at 14,000 rpm. 420 µl from each tube was removed and dried in vacuo. Each sample was reconstituted in 65 µl 20 mM aqueous ammonium formate pH 4.5 buffer (AF) containing acetonitrile (20%) prior to analysis by reverse phase liquid chromatography in combination with tandem mass spectrometry (LC MS/MS).

Urine was collected at 2 and 24 hours post administration from pairs of mice in metabolic cages. Urine samples were diluted with AF containing acetonitrile (20%) to give a target analyte concentration within the practical range of the LC MS/MS assay. 30 µl of each diluted sample was placed in an Eppendorf tube (1.5 ml) and an internal standard of daunorubicin (20 µL at 0.5 mg/ml) was added together with 50 µl of AF containing acetonitrile (20%). Each sample was then analyzed by LC MS/MS.

An Agilent HP1100 HPLC with DAD detector and Chemstation software was coupled to a PE Sciex API 365 mass spectrometer with an electrospray ion source. HPLC was performed on a TSK-Gel Super ODS, 2 mm, 4.6×50 mm (TosoHaas) reversed phase column equipped with a HAI-GUARD C18 guard disc (Higgins Analytical) and stainless steel frit (Upchurch Scientific). Chromatography was performed at room temperature. The flow rate was 0.5 ml/min. Injection volume was 50 µl. Gradient elution was performed using a mobile phase of 20 mM aqueous AF pH 4.5 buffer with increasing amounts of acetonitrile. The API 365 was operated at 365° C. in a multiple reaction monitoring mode, set to monitor specific analyte parent-daughter ion pairs. Integration of chromatograms was performed by MacQuant software (PE Sciex) and quantitation of each analyte obtained by comparison to previously obtained calibration curves. Daunorubicin was used as an internal standard in all cases.

Figure 16:
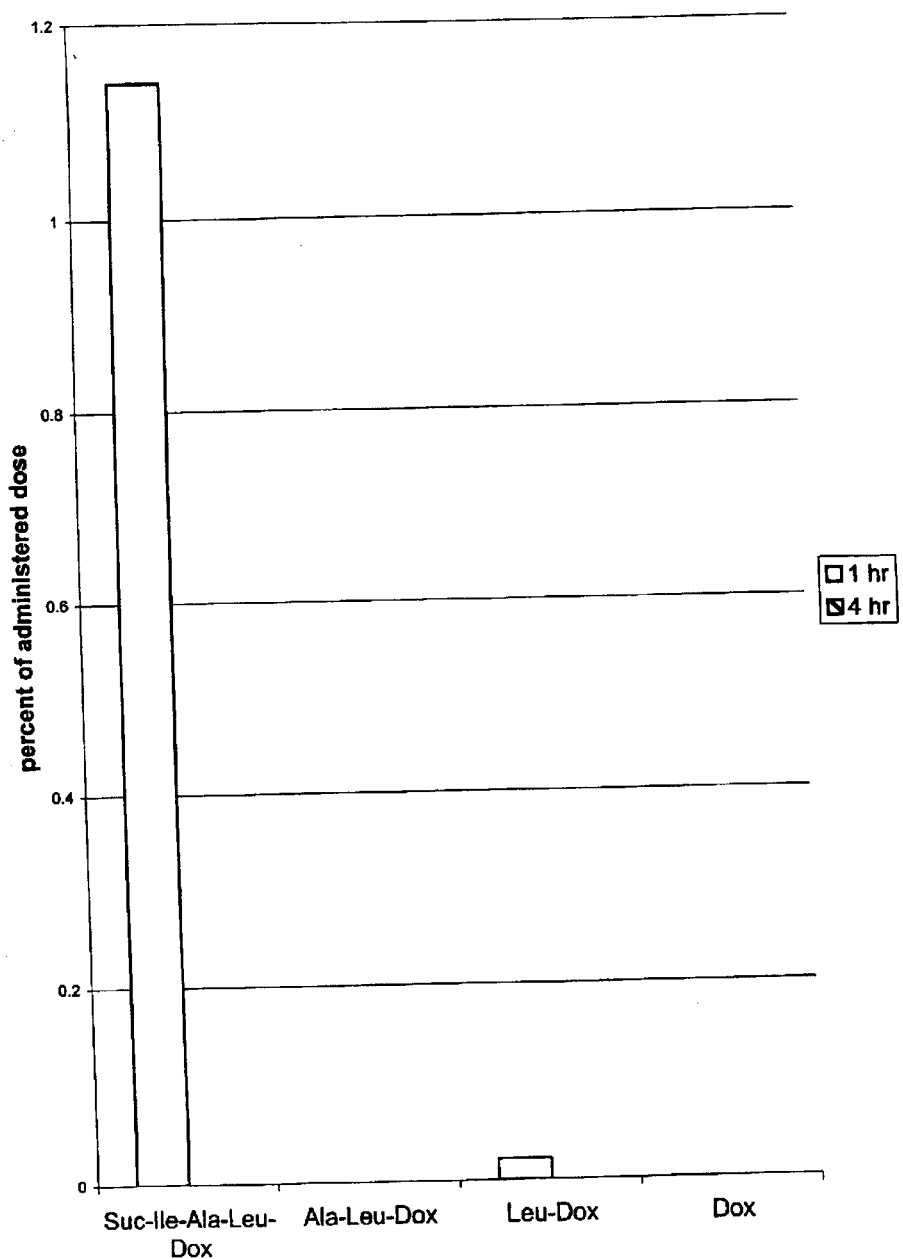
FIG. 16 is a graph of the plasma levels of Suc-Ile-Ala-Leu-Dox (SEQ ID NO: 42) and its metabolites at 1 and 4
Figure 17:
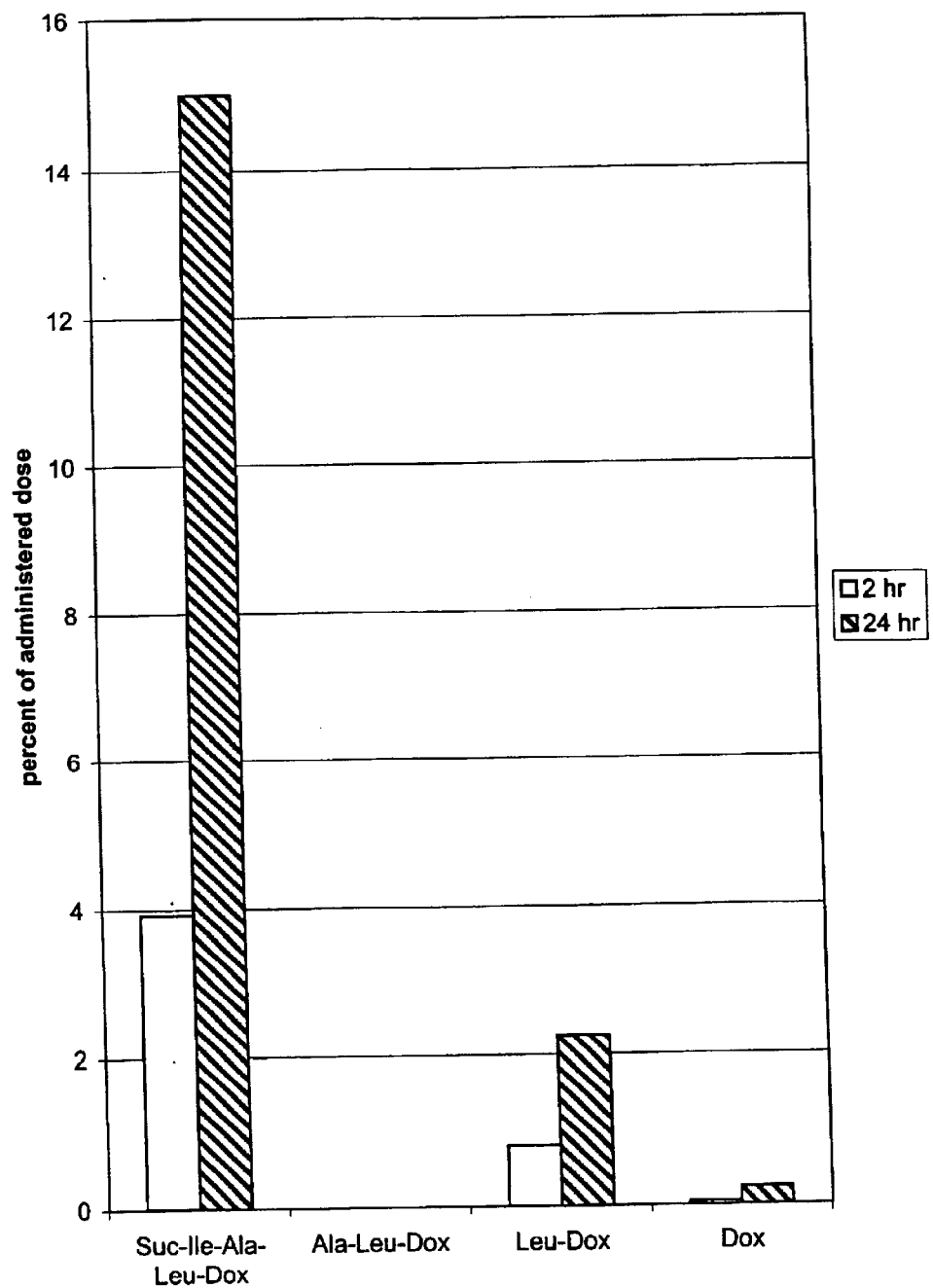
FIG. 17 is a graph of the amount of Suc-Ile-Ala-Leu-Dox (SEQ ID NO: 42) and its metabolites present in the urine collected 0–2 and 2–24 hours after the administration of a single intravenous bolus of the prodrug.

As seen in Table 13 and FIG. 16, Suc-Ile-Ala-Leu-Dox SEQ ID NO: 42 was cleared from the circulation very rapidly, with approximately 1.1% of the administered dose detected at 1 hour, while by 4 hours it was virtually undetectable. For the calculation of percent of administered dose, plasma volume was estimated to be 40% of blood volume, which was calculated as 7% of animal's body weight. At 2 and 24 hours the parent compound was detected in urine at 3.9% and 15.0% of the administered dose, showing that the kidney is a major organ of excretion for the prodrug (FIG. 17).

TABLE 13

| | Plasma (% adm. dose) | | Urine (% adm. dose) | |
|---|---|---|---|---|
| | 1 hr | 4 hr | 2 hr | 24 hr |
| Suc-Ile-Ala-Leu-Dox SEQ ID NO: 42 | 1.14 | 0.00 | 3.92 | 15.0 |
| Ala-Leu-Dox | 0.00 | 0.00 | 0.00 | 0.00 |
| Leu-Dox | 0.02 | 0.00 | 1.17 | 2.25 |
| Dox | 0.00 | 0.00 | 0.06 | 0.36 |

Ala-Leu-Dox was not detected in plasma or urine. The major peptide metabolite was Leu-Dox. Doxorubicin was virtually undetectable in plasma but was found in urine at low levels at 2 and 24 hours. The levels of both parent and metabolites were higher in urine at 24 hours than at 2 hours. This most likely resulted from later urination of the mice, relative to the initial urine collection time (2 hours). The urine values represent an accumulation from 0–2 hours and from 2–24 hours, thus later urination (after 2 hours) would be accumulated in the 2–24 hour sample.

A low level of cleavage and activation of the Suc-Ile-Ala-Leu-Dox SEQ ID NO: 42 prodrug occurred in the blood of normal mice. The minimal toxicity observed with Suc-Ile-Ala-Leu-Dox SEQ ID NO: 42 at the high dose-level tested (Example 11), confirms that there is almost no systemic production of the active metabolite doxorubicin which, when present systemically, is toxic to normal tissues.

Example 18

Metabolism of Suc-βAla-Ile-Ala-Leu-Dox (SEQ ID NO:39)

The metabolism and clearance of Suc-βAla-Ile-Ala-Leu-Dox SEQ ID NO: 39 was studied in normal mice administered a single intravenous bolus dose at 117 mg/kg Suc-βAla-Ile-Ala-Leu-Dox SEQ ID NO: 39. Plasma samples were obtained at 1 and 4 hours from separate mice. Urine was collected at 2 and 24 hours post administration from pairs of mice in metabolic cages. The plasma and urine samples were prepared and analyzed as described in Example 17.

Figure 18:
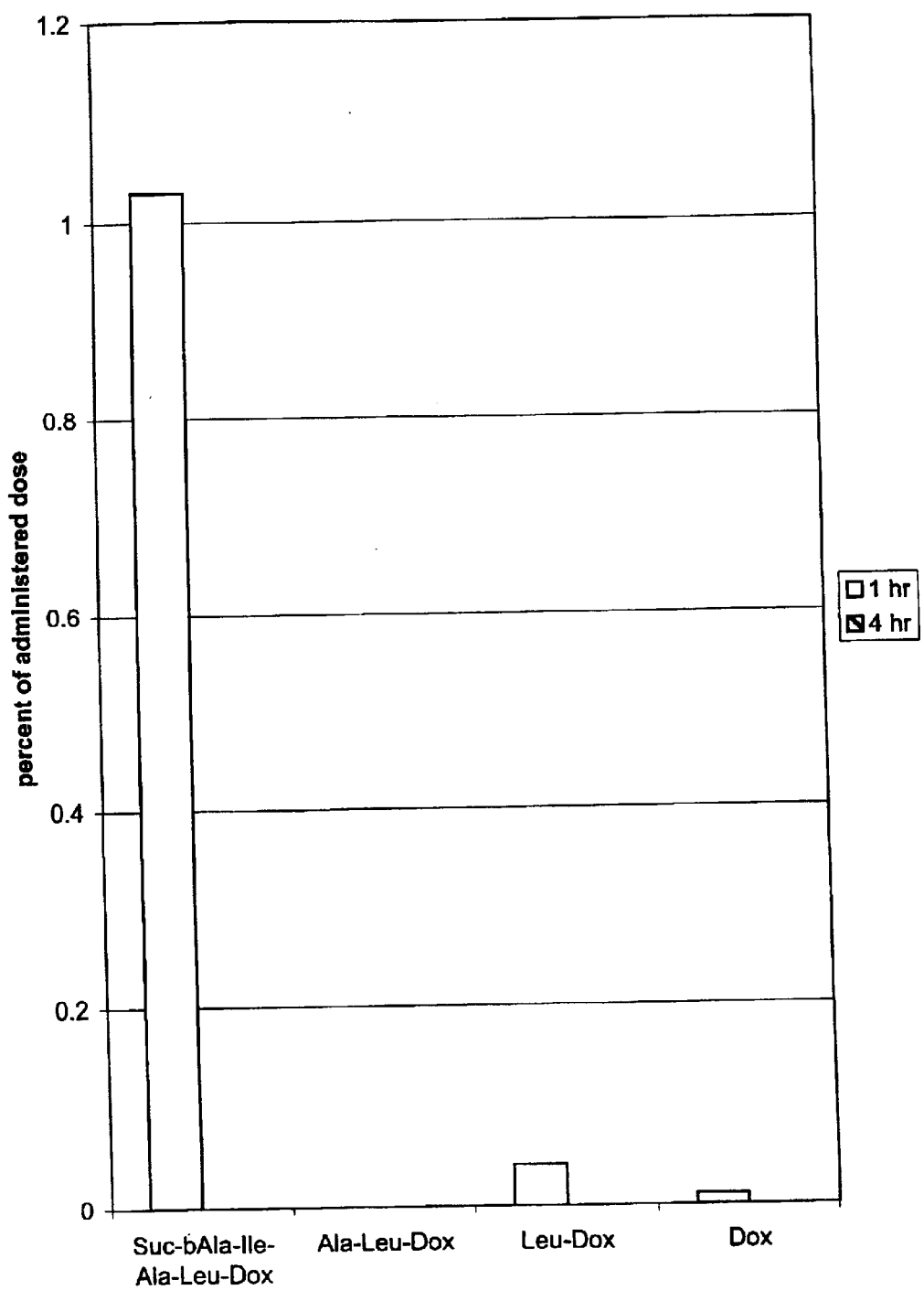
FIG. 18 is a graph of the plasma levels of Suc-βAla-Ile-Ala-Leu-Dox (SEQ ID NO: 39) and its metabolites at 1 and 4 hours after administration of a single intravenous bolus dose of the prodrug.
Figure 19:
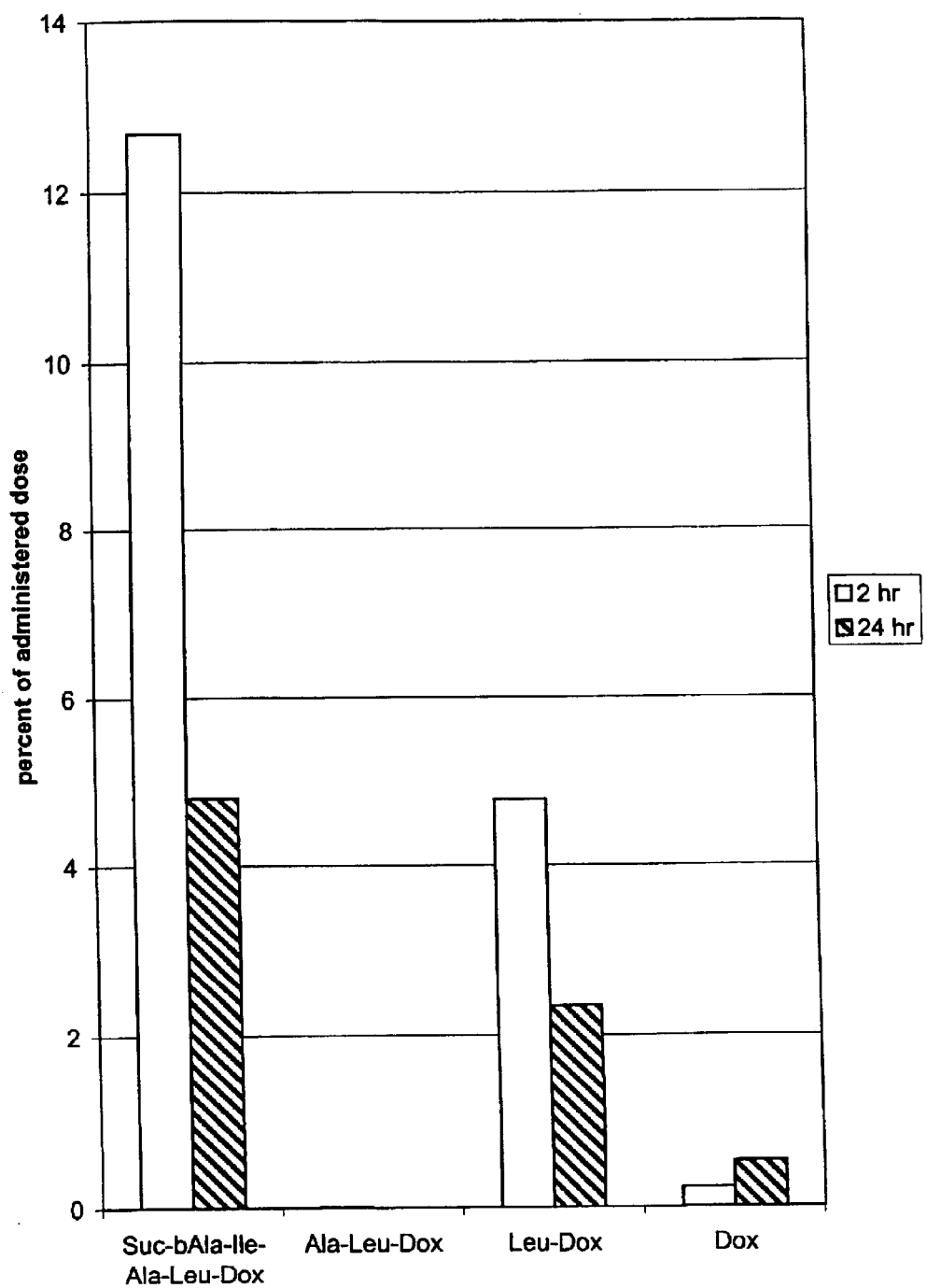
FIG. 19 is a graph of the amount of Suc-βAla-Ile-Ala-Leu-Dox (SEQ ID NO: 39) and its metabolites present in the urine collected 0–2 and 2–24 hours after the administration of a single intravenous bolus of the prodrug.

Suc-βAla-Ile-Ala-Leu-Dox SEQ ID NO: 39 was cleared from the circulation very rapidly: approximately 1.0% of the administered dose could be detected in plasma at 1 hour, while it was virtually undetectable at 4 hours (Table 14 and FIG. 18). At 2 and 24 hours the urine contained 12.7% and 4.81% of the administered dose, indicating that the kidney is a major organ of excretion for the prodrug (FIG. 19).

TABLE 14

|  | Plasma (% adm. dose) | | Urine (% adm. dose) | |
| --- | --- | --- | --- | --- |
|  | 1 hr | 4 hr | 2 hr | 24 hr |
| Suc-βAla-Ile-Ala-Leu-Dox SEQ ID NO: 39 | 1.03 | 0.00 | 12.7 | 4.81 |
| Ala-Leu-Dox | 0.00 | 0.00 | 0.01 | 0.00 |
| Leu-Dox | 0.04 | 0.00 | 4.69 | 2.29 |
| Dox | 0.01 | 0.00 | 0.21 | 0.51 |

The metabolite Ala-Leu-Dox was virtually undetectable in plasma, and was found at very low levels in urine at 2 hours. The major peptide metabolite was Leu-Dox, which could be detected at low levels in plasma at 1 hour, as well as in urine at 2 hours and 24 hours. Little free doxorubicin was present in plasma however comparatively high levels were detected in urine, showing that some complete metabolism is occurring.

In these samples, the levels of both the parent and metabolites were higher in urine at 2 hours than at 24 hours. The sum of the amount of Suc-βAla-Ile-Ala-Leu-Dox SEQ ID NO: 39 and metabolites collected at 0–2 hours and 2–24 hours is similar to that of Suc-Ile-Ala-Leu-Dox SEQ ID NO: 42 (see Example 17). Thus, there is no physiologically significant difference between the clearance of Suc-βAla-Ile-Ala-Leu-Dox SEQ ID NO: 39 and Suc-Ile-Ala-Leu-Dox SEQ ID NO: 42.

Example 19

Advantages of Prodrugs over the Unconjugated Therapeutic Agent

The prodrugs of the invention provide treatment advantages over the therapeutic agent in its unconjugated form.

In the single dose Maximum Tolerated Dose (MTD) studies, groups of normal mice were administered intravenous bolus doses of the prodrug. The mice were observed daily for 28 days and body weights measured twice weekly. The MTD was estimated to be equal to the highest dose that produced no death in mice after 28 days. As shown in Table 15, the single-dose SD-MTD of the isoleucine containing prodrugs range from 1.6-fold to 2.5-fold higher than that of doxorubicin alone.

In repeat-dose studies in tumor bearing mice, groups of ten mice were dosed with various amounts of prodrug for a total of five doses at either five day or 1 week intervals. After frequent observation over 60 days, the dose that proved to be within acceptable toxicity limits was identified as the maximum tolerated repeat dose. As seen in Table 15, RD-MTD of the prodrugs are approximately 6.5-fold higher than that of doxorubicin alone. Repeat dosing of the prodrugs at or lower than their RD-MTD significantly prolong survival of LS174t tumor bearing mice, whereas that of doxorubicin is completely ineffective. Thus, the conclusion remains the same in that the prodrugs permit a much greater amount of therapeutic agent to be delivered to the body as a whole and to the vicinity of the target cell.

TABLE 15

| Compound | SD MTD (mg/kg)* | Repeat Dose MTD (mg/kg)* | Repeat Dose Frequency | Major Plasma Metabolite |
| --- | --- | --- | --- | --- |
| Suc-βAla-Ile-Ala-Leu-Dox SEQ ID NO: 39 | 75 (42) | 53 (30) | Q 5D × 5 | Leu-Dox |
| Suc-Ile-Ala-Leu-Dox SEQ ID NO: 42 | 94 (56) | n.d. | n.d. | Leu-Dox |
| Suc-βAla-Leu-Ala-Leu-Dox SEQ ID NO: 41 | 50 (28) | 57 (32) | Q 7D × 5 | Ala-Leu-Dox |
| Suc-Leu-Ala-Leu-Dox SEQ ID NO: 45 | 59 (35) | 52 (31) | Q 5D × 5 | Leu-Dox |
| Doxorubicin | 16 (16) | 4 (4) | Q 7D × 5 | n.a. | n.d. = not determine;
n.a. = not applicable
*values in parentheses are the doxorubicin equivalent dose Example 20

Suc-βAla-Ile-Ala-Leu-Dox (SEQ ID NO:39) is Well Tolerated in Tumor Bearing Mice

Figure 20:
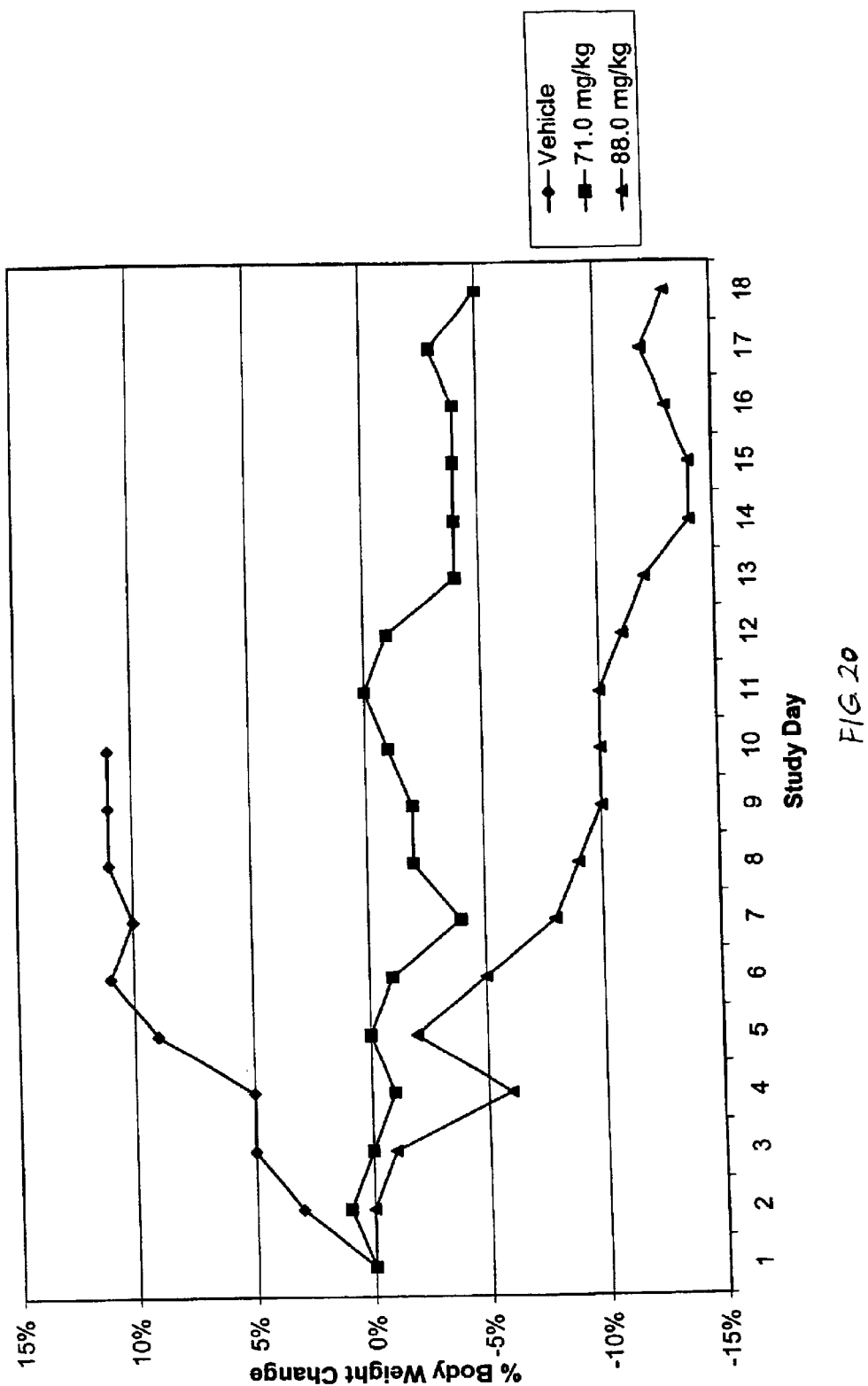
FIG. 20 is a graph of the Percent Body Weight Change of mice treated with Suc-βAla-Ile-Ala-Leu-Dox (SEQ ID NO: 39) or receiving the vehicle control.

The prodrug Suc-βAla-Ile-Ala-Leu-Dox SEQ ID NO: 39 therapeutic agent is significantly better tolerated than doxorubicin under repeat-dose conditions. As would be expected, when a dose similar to the single-dose MTD (75 mg/kg) (See Example 16) was administered as a repeat-dose it was less well tolerated. In repeat-dose studies in tumor bearing mice, three groups of ten mice were dosed with 0, 53 or 68 mg/kg Suc-βAla-Ile-Ala-Leu-Dox SEQ ID NO: 39 (equivalent to 0, 30 and 38 mg doxorubicin/kg), for a total five identical doses (Q5DX5) and observed frequently for 60 days. All treated animals lost weight progressively throughout the study, while the vehicle control group gained up to 12% of the mean initial body weight. (FIG. 20). Two treated animals in the high dose group were terminated due to signs of toxicity, with body weight loss of greater that 20% of their initial weight. The signs of toxicity were similar to those observed following a single, high dose (See Example 16) and were consistent with the known toxicity profile of doxorubicin in rodents. Thus cumulative toxicity resulted from repeat-dosing at these relatively high dose-levels. However the maximal overall exposures to doxorubicin of the animals in the two dose groups after 5 doses were 150 and 190 mg/kg, respectively, which is significantly higher (8 to 10 times) than the tolerated repeat dose level of doxorubicin (4 mg/kg, or 20 mg/kg total exposure after 5 doses).

However, the RD-MTD of Suc-βAla-Ile-Ala-Leu-Dox SEQ ID NO: 39 was approximately 150 mg/kg doxorubicin equivalent which was at least 6–5-fold higher than the tolerated request dose level of doxorubicin (standard safe RD efficacious dose of 20 mg/kg total exposure after 5 doses of 4 mg/kg).

Example 21

Suc-βAla-Leu-Ala-Leu-Dox (SEQ ID NO:41) is Better Tolerated in vivo than Doxorubicin Suc-βAla-Leu-Ala-Leu-Dox SEQ ID NO: 41, an exemplary tetrapeptide prodrug of the invention, is well tolerated in mice. In a second single dose Maximum Tolerated Dose (SD-MTD) study, groups of five normal ICR mice were administered intravenous bolus doses of Suc-βAla-Leu-Ala-Leu-Dox SEQ ID NO: 41. The mice were observed daily for 49 days and body weights measured twice weekly. Dose levels tested were 0, 50, 75 or 100 mg/kg, equivalent to 0, 28, 42 or 56 mg/kg of doxorubicin, respectively. There was no acute toxicity, within 24 hours, at any dose level. Dose and time dependent signs of toxicity were observed during the study. Toxicity, including partial hind-end paralysis and significant body weight loss (>20% of their initial weight) was observed in the 75 and 100 mg/kg dose groups. By Day 35 mortality was observed in 40% of the 75 mg/kg dose group. Based on survival and lack of signs of toxicity at Day 49, the SD-MTD for Suc-βAla-Leu-Ala-Leu-Dox SEQ ID NO: 41 was determined to be 50 mg/kg (equivalent to 28 mg/kg of doxorubicin). This dose was very well tolerated and no adverse effects were observed. Therefore, the SD-MTD was approximately 1.8-fold higher on a molar basis than the SD-MTD for doxorubicin alone (16 mg/kg). See Table 16. This is an approximate SD-MTD determination based on a range of doses at 14 mg/kg doxorubicin equivalents increments over the range tested.

TABLE 16

| Compound | SD-MTD (mg/kg) | SD-MTD (mg/kg Dox equiv.) | SD-MTD Molar Ratio (Dox equiv.) |
|---|---|---|---|
| Doxorubicin | 16 | 16 | 1 |
| Suc-βAla-Leu-Ala-Leu-Dox SEQ ID NO: 41 | 50 | 28 | 1.8 |

Example 22

Suc-βAla-Ile-Ala-Leu-Dox (SEQ ID NO:39) is Effective in Tumor Bearing Mice

Figure 21:
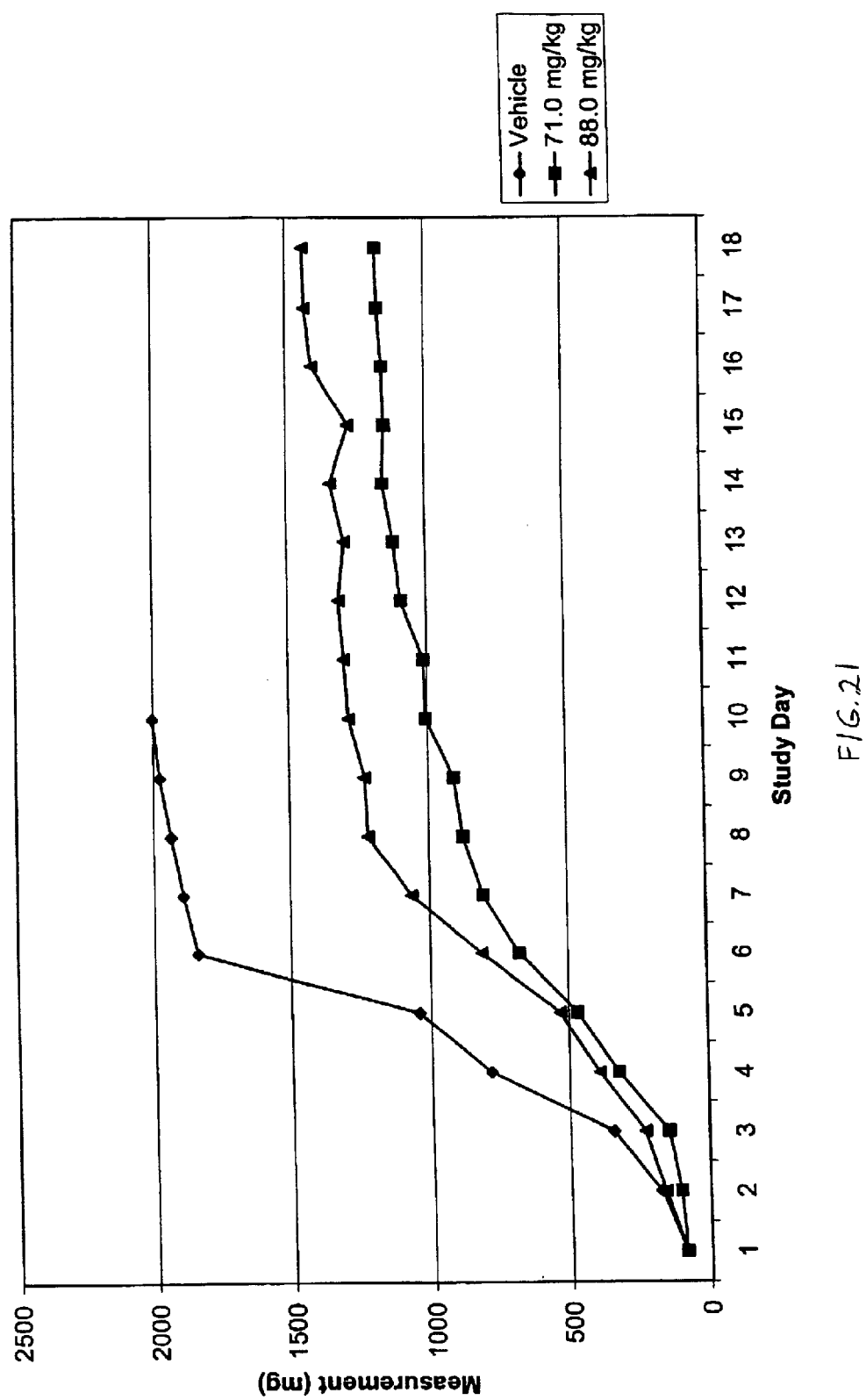
FIG. 21 is a graph of the rate of tumor growth in LS174T xenografted mice either treated with Suc-βAla-Ile-Ala-Leu-Dox (SEQ ID NO: 39) or given the vehicle control.

The Suc-βAla-Ile-Ala-Leu-Dox SEQ ID NO: 39 therapeutic agent has proven to be efficacious in extending the survival of mice and inhibiting the growth of human tumors in a mouse xenograft model utilizing the doxorubicin-resistant colorectal carcinoma LS 174t. For example, groups of ten nude mice, subcutaneously implanted with chunks of LS174t which were allowed to grow to approximately 50 mg, were treated intravenously with at 0, 53 or 68 mg/kg of Suc-βAla-Ile-Ala-Leu-Dox SEQ ID NO: 39 (equivalent to 0, 30 or 38 mg/kg doxorubicin) at five day intervals for a total of five identical doses (Q5DX5). Tumors and body weights were measured twice weekly for up to 60 days. As seen in FIG. 21, both doses were efficacious in reducing the growth of tumors compared with vehicle control animals. There were 4 and 2 long-term survivors in the low and high dose groups, respectively, compared with 0 in the vehicle control group. The Mean Day of Survival (MDS) in animals whose tumors reached 1.5 g prior to Day 60 was significantly better in the low (29.7 days) and high (23.4 day) dose groups than in the vehicle control group (18.2 days). Thus, Suc-βAla-Ile-Ala-Leu-Dox SEQ ID NO: 39 was efficacious in this aggressive human tumor model, in which doxorubicin alone at its tolerated dose (3 mg/kg), under this dosing regimen, is historically ineffective.

Example 23

Efficacy of Suc-βAla-Leu-Ala-Leu-Dox (SEQ ID NO:41) Against LNCaP Tumors in Nude Mice The Suc-βAla-Leu-Ala-Leu-Dox SEQ ID NO: 41 therapeutic agent has proven to be efficacious in inhibiting the growth of human tumors in a mouse xenograft model utilizing the prostate carcinoma LNCaP. Groups of six or seven nude mice, subcutaneously injected with 4 million LNCaP cells, were treated intravenously with at saline, 5 mg/kg of doxorubicin or 59 mg/kg of Suc-βAla-Leu-Ala-Leu-Dox SEQ ID NO: 41 (equivalent to 33 mg/kg doxorubicin) at seven day intervals for a total of five identical doses (Q7DX5). The mice were weighed and tumors were measured (by caliper) at least once a week prior to start of dosing (Day 0), then twice a week during the study. Immediately before the start of dosing (Study Day -2 to Day 0), mice were randomized to various groups based on the weight of the tumors. The mean tumor weight was approximately 250 mg at Day 0. Mice were euthanized after the tumors reached a cutoff weight of 1.5 g (cancer endpoint), or when mice suffered over 25% weight loss (toxic endpoint). Studies were terminated at Day 60. One mouse dosed with doxorubicin was excluded from evaluation because the tumor ulcerated.

In nude mice, the vehicle control group tumors grew relatively slowly (FIG. 22) and the tumor exhibited heterogeneous growth characteristics, with termination at the tumor weight endpoint ranging from Day 29 to Day 60 (data not shown). Progressive loss of body weight occurred in the control mice, which lost 15% mean weight over the study (FIG. 23). Such cachectic weight loss is possibly due to LNCaP xenografts and has been reported by other groups (DeFeo-Jones et al., "A peptide-doxorubicin 'prodrug' activated by prostate-specific antigen selectively kills prostate tumor cells positive for prostate-specific antigen in vivo," Nature Medicine 6(11):1248–1252 (2000)). Non-tumor-bearing mice from the same shipments maintained weight and sentinel mice were normal by colony health surveillance. Mice receiving Suc-βAla-Leu-Ala-Leu-Dox SEQ ID NO: 41 and doxorubicin had over 20% mean weight loss (FIG. 23). The combined effects of the baseline weight loss in tumor-bearing mice due to the tumors, and weight loss due to the test compounds, resulted in both Suc-βAla-Leu-Ala-Leu-Dox SEQ ID NO: 41 and doxorubicin exceeding the allowed weight loss, and being unacceptably toxic at the relatively high dosing regimens tested, with 7 of 7 and 4 of 5 mice respectively terminated for excessive weight loss in these treatment groups (Table 17).

TABLE 17

Efficacy Against LNCaP Tumors in Nude Mice

| Compound | Tumor Weight | % Tumor Growth Inhibition | Survivor (day 60) | Cancer Endpt. | Toxic Endpt. |
|---|---|---|---|---|---|
| Saline | D14: 840 ± 112 D21: 941 ± 137 | – | 2 | 4 | 0 |
| Doxorubicin^ | D14: 567 ± 77 | D14: 32 ± 16 D21: N/A | 1 | 0 | 4 |
| Suc-βAla-Leu-Ala-Leu-Dox SEQ ID NO: 41 | D14: 391 ± 70 D21: 318 ± 67 | D14: 53 ± 15* D21: 66 ± 15* | 0 | 0 | 7 |

*Statistically different from the control at the p level of 0.01 (two-tailed unpaired t test)

Figure 22:
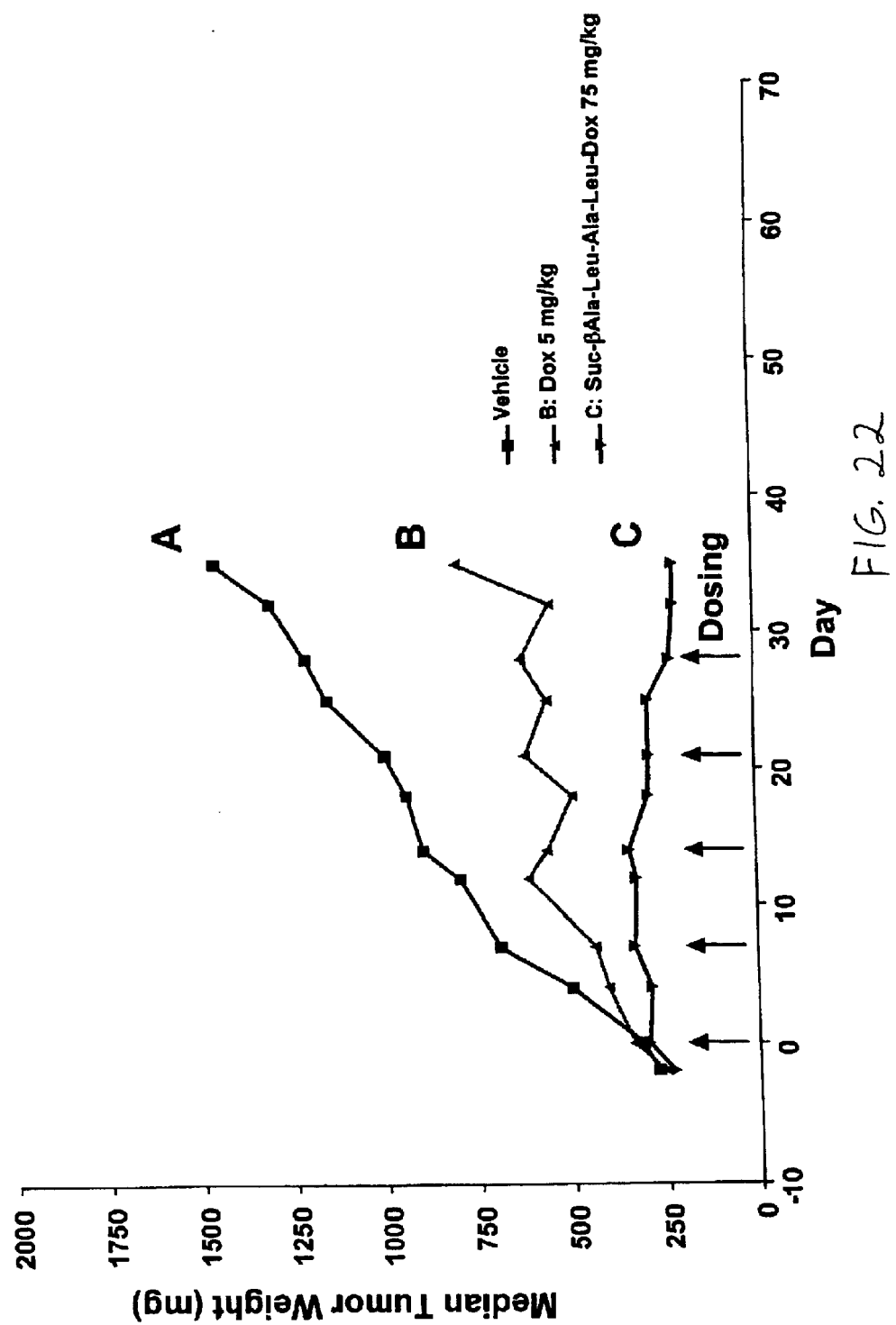
FIG. 22 is a graph of growth of LNCaP in nude mice treated with vehicle, doxorubicin, or Suc-βAla-Leu-Ala-Leu-Dox (SEQ ID NO. 41).
Figure 23:
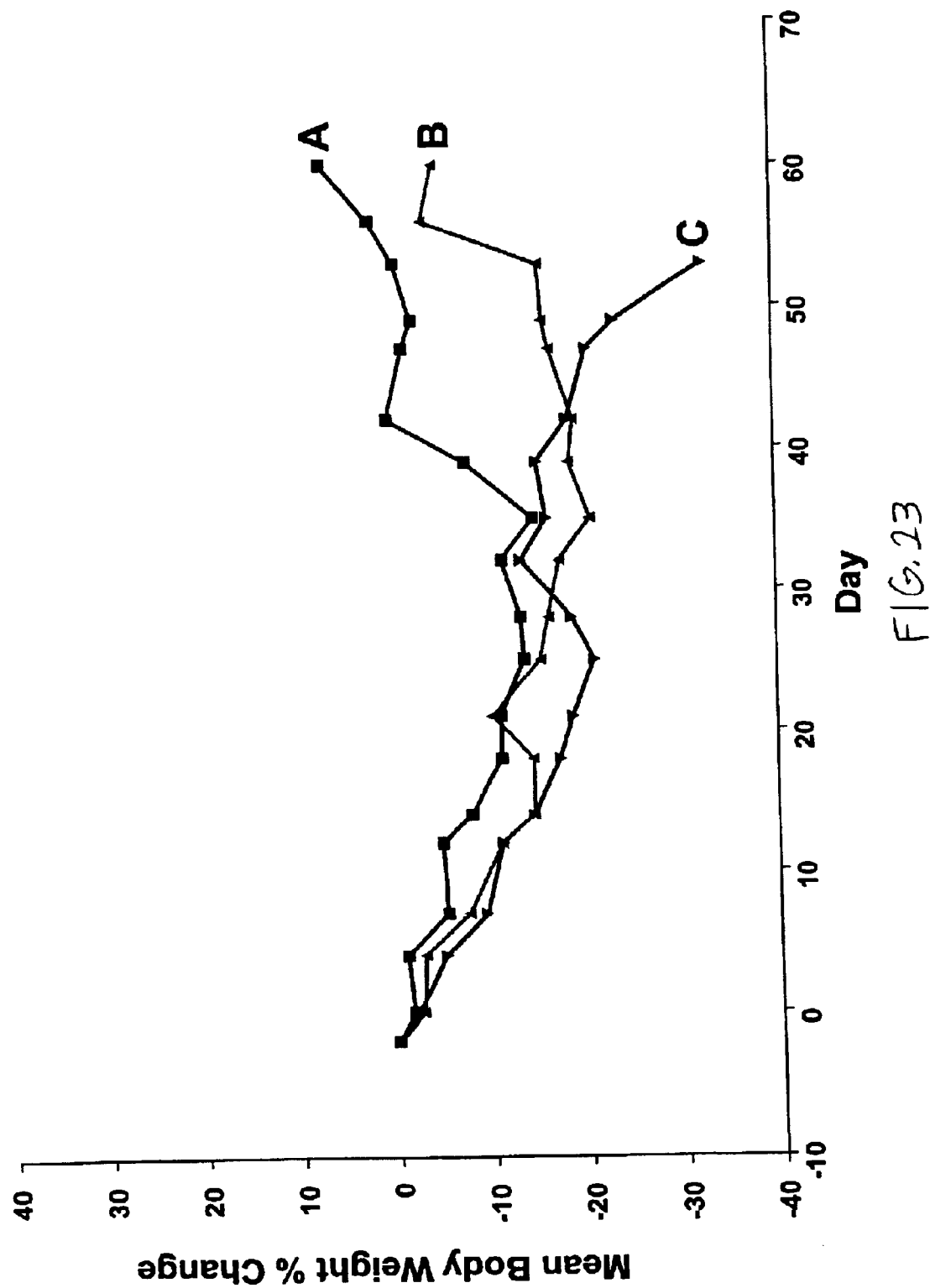
FIG. 23 is a graph of the body weight of nude mice containing xenografted LNCaP tumors.

Suc-βAla-Leu-Ala-Leu-Dox SEQ ID NO: 41 completely inhibited the growth of LNCaP tumors (FIG. 22; Table 17). No Survival endpoint was determined in this study due to the slow growth characteristics of the tumors, with animals in the control group continuing to the designated study end-date (Day 60). The mean tumor weight of all mice when terminated in the Suc-βAla-Leu-Ala-Leu-Dox SEQ ID NO: 41 group was significantly less than the doxorubicin only group (232 mg, and 967 mg, respectively; calculated, not shown). Overall, Suc-βAla-Leu-Ala-Leu-Dox SEQ ID NO: 41 was superior to doxorubicin in inhibiting tumor growth.

Example 24

Efficacy Against LNCaP Tumors in SCID Mice

The LNCaP xenograft study was then repeated with modification as follows: SCID mice were used, with additional lower doses of both doxorubicin and Suc-βAla-Leu-Ala-Leu-Dox SEQ ID NO: 41 tested to obtain a well-tolerated dose-response, and limiting the dosing to 2 doses, six days apart, to minimize the additive effects of the compound on the baseline tumor-related weight loss. Accordingly, groups of ten CB17.5CID mice, subcutaneously injected with 2.5 million LNCaP cells, were treated intravenously with saline, 3 or 4 mg/kg of doxorubicin or 40, 50 or 62 mg/kg of Suc-βAla-Leu-Ala-Leu-Dox SEQ ID NO: 41 (equivalent to 22, 28 and 35 mg/kg doxorubicin, respectively) at six day intervals for a total of two identical doses (Q6DX2). The mice were weighed and tumors were measured (by caliper) at least once a week prior to start of dosing (Day 0), then twice a week during the study. Immediately before the start of dosing (Study Day −2 to Day 0), mice were randomized to various groups based on the weight of the tumors. The mean tumor weight was approximately 200 mg at Day 0. Mice were euthanized after the tumors reached a cutoff weight of 1.5 g (cancer endpoint), or when mice suffered over 25% weight loss (toxic endpoint). Studies were terminated at Day 60.

Figure 24:
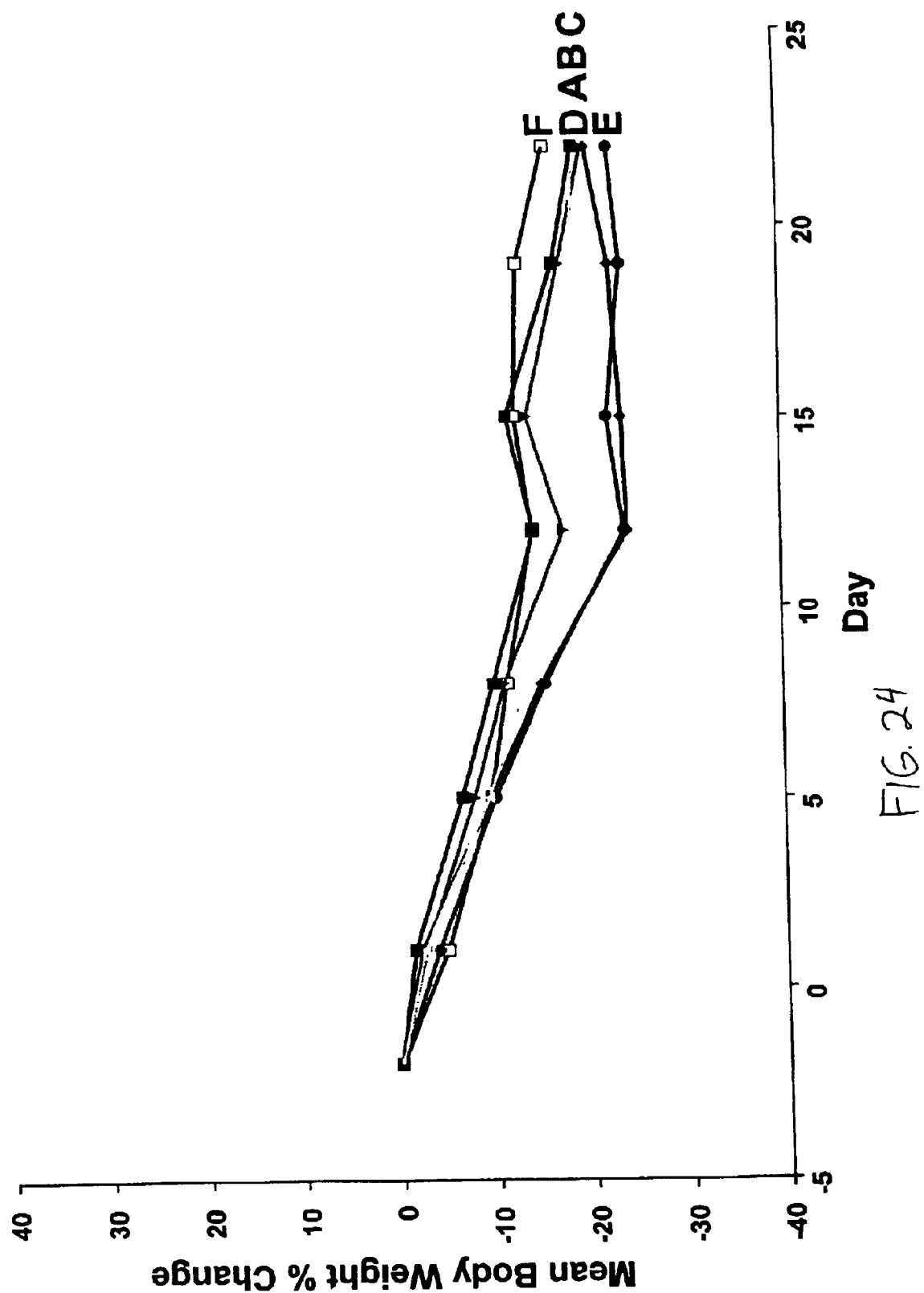
FIG. 24 is a graph of the body weight of nude mice containing xenografted LNCaP tumors.

The vehicle control group mice implanted with the LNCaP tumor again gradually declined in weight from the time of implantation and by Day 22 had a mean weight loss of about 19% (FIG. 24). A plateau in body weight loss in all mice in the study at about Day 12 coincided with a change of diet from standard rodent chow to a high-fat rodent diet, done to control the observed tumor-related cachexia.

Figure 25:
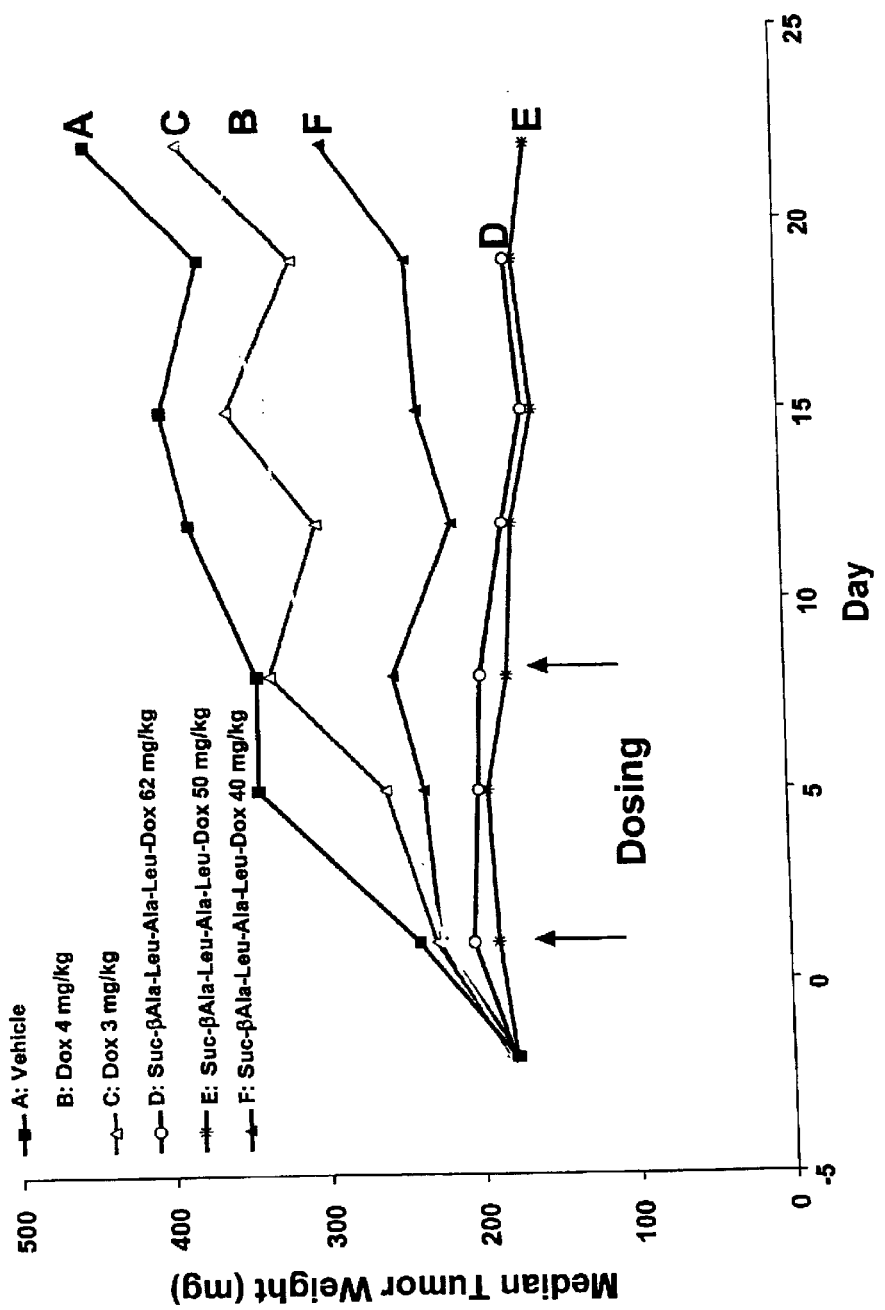
FIG. 25 is a graph of growth of LNCaP tumors in nude mice treated with vehicle, doxorubicin or Suc-βAla-Leu-Ala-Leu-Dox (SEQ ID NO: 41).

Suc-βAla-Leu-Ala-Leu-Dox SEQ ID NO: 41 at all three dose levels significantly inhibited tumor growth at Day 12, the last day of measurement on which all mice were alive. A trend of dose-related increase in efficacy was observed, although the efficacy was maximal at 50 mg/kg. Suc-βAla-Leu-Ala-Leu-Dox SEQ ID NO: 41 (40 mg/kg) inhibited tumor growth to a greater extent than doxorubicin at 3 or 4 mg/kg, both of which failed to achieve statistical significance (FIG. 25 and Table 18).

Mice receiving 40 mg/kg Suc-βAla-Leu-Ala-Leu-Dox SEQ ID NO: 41 had about the same percentage mean weight loss from the start of dosing as the control and less than both doxorubicin groups (FIG. 24). Several mice receiving 50 and 62 mg/kg Suc-βAla-Leu-Ala-Leu-Dox SEQ ID NO: 41 had an unacceptable level of weight loss of over 20% by Day 22 (FIG. 24 and Table 18).

TABLE 18

Efficacy Against LNCaP Tumors in SCID Mice

| Compound | Dose (mg/kg) | Tumor Weight | % Tumor Growth Inhibition | Survivor (day 22) | Toxic Endpt. |
|---|---|---|---|---|---|
| Saline | – | 416 ± 36 | – | 9 | 1 |
| Doxorubicin | 4 | 310 ± 25 | 26 ± 6 | 8 | 2 |
| Doxorubicin | 3 | 328 ± 35 | 21 ± 8 | 9 | 1 |
| Suc-βAla-Leu-Ala-Leu-Dox SEQ ID NO: 41 | 62 | 196 ± 22 | 53 ± 5* | 4 | 6 |
| Suc-βAla-Leu-Ala-Leu-Dox SEQ ID NO: 41 | 50 | 168 ± 29 | 60 ± 7* | 5 | 5 |
| Suc-βAla-Leu-Ala-Leu-Dox SEQ ID NO: 41 | 40 | 244 ± 25 | 41 ± 6* | 10 | 0 |

Overall Suc-βAla-Leu-Ala-Leu-Dox SEQ ID NO: 41 was effective and superior to doxorubicin in inhibiting LNCaP tumor growth after 2 weekly treatments.

Example 25

Efficacy of Suc-Leu-Ala-Gly-Dox and Suc-βAla-Leu-Ala-Leu-Dox on LNCaP Xenografts LNCaP human prostate carcinoma cells express high levels of CD10 on the surface. Suc-βAla-Leu-Ala-Leu-Dox SEQ ID NO: 41 and Suc-Leu-Ala-Gly-Dox SEQ ID NO: 46 were tested at a single dose level Q7Dx5. Groups of eight male NCr nude mice, subcutaneously injected with 4 million LNCaP cells, were treated intravenously with saline, 5 mg/kg of doxorubicin, 59 mg/kg of Suc-βAla-Leu-Ala-Leu-Dox SEQ ID NO: 41 (equivalent to 33 mg/kg doxorubicin) or 73 mg/kg of Suc-Leu-Ala-Gly-Dox SEQ ID NO: 46 (equivalent to 47 mg/kg doxorubicin; or 81 mg/kg Suc-βAla-Leu-Ala-Leu-Dox SEQ ID NO: 41) at seven day intervals for a total of five identical doses (Q7DX5) (Table 19). The mice were weighed and tumors were measured (by caliper) at least once a week prior to start of dosing (Day 0), then twice a week during the study. Immediately before the start of dosing (Study Day −2 to Day 0), mice were randomized to various groups based on the weight of the tumors. The mean tumor weight was approximately 250 mg at Day 0. Mice were euthanized after the tumors reached a cutoff weight of 1.5 g (cancer endpoint), or when mice suffered over 25% weight loss (toxic endpoint). Studies were terminated at Day 60. One mouse dosed with doxorubicin was excluded from evaluation because the tumor ulcerated.

Example 26

Efficacy of Suc-Leu-Ala-Gly-Dox Against HT-29, a CD10$^{neg}$ Cell Line

A mouse xenograft study demonstrated the efficacy of Suc-Leu-Ala-Gly-Dox SEQ ID NO: 46 on the growth of human colon carcinoma (HT-29), and the outcome in terms of long-term survival. Healthy young male nude mice were subcutaneously injected with 5 million of HT-29 cells. When the tumors reached approximately 100 mg in weight, treatment every 7 days for 5 doses, of group of 8, 10, or 12 mice with vehicle, 4 mg/kg doxorubicin, 40 or 67 mg/kg Suc-Leu-Ala-Gly-Dox SEQ ID NO: 46 was initiated. Tumor size and body weights were measured twice weekly for up to 60 days.

A dose-dependent increase in survival of the mice was observed. Suc-Leu-Ala-Gly-Dox SEQ ID NO: 46, given at

TABLE 19

| Compound | Dose (mg/kg) | Tumor Weight (mg) | Tumor Growth Inhibition (% over control) | Toxicity (Weight Loss > 25%) |
|---|---|---|---|---|
| Saline | — | D12: 806 ± 135 (n = 6) | 0 | 0/6 |
| | | D14: 840 ± 112 (n = 6) | | |
| | | D21: 941 ± 137 (n = 6) | | |
| Suc-βAla-Leu-Ala-Leu-Dox SEQ ID NO: 41 | 75 | D14: 391 ± 70 (n = 7) | D14: 53.4** | 7/7 |
| | | D21: 318 ± 67 (n = 7) | D21: 66.2** | |
| Doxorubicin | 5 | D14: 567 ± 77 (n = 6) | 32.5 | 4/6 |
| Suc-Leu-Ala-Gly-Dox SEQ ID NO: 46 | 110 | D12: 795 ± 177 (n = 7) | 1.4 | 1/7 |

**Statistically different from the control (p < 0.01, two-tailed)

Suc-βAla-Leu-Ala-Leu-Dox SEQ ID NO: 41 completely shut down LNCaP tumor growth, induced tumor regression of all treated mice and was more effective than doxorubicin (Table 19). Interestingly, Suc-Leu-Ala-Gly-Dox SEQ ID NO: 46 dosed at 37% higher molar concentration than Suc-βAla-Leu-Ala-Leu-Dox SEQ ID NO: 41, was not effective at all. In this study, Suc-βAla-Leu-Ala-Leu-Dox SEQ ID NO: 41 was dosed at approximately its RD-MTD in other tumor models (LS174T and MX-1). However, this dose proved to be too high in LNCaP tumor bearing mice as even the vehicle control mice with LNCaP tumors experienced about 15% average body weight loss. Such cachectic (general physical wasting and malnutrition usually associated with chronic disease) weight loss is possibly due to LNCaP xenografts and has been reported by other groups (DeFeo-Jones et al., Nature Medicine 6(11):1248–1252 (2000)). Surprisingly, Suc-Leu-Ala-Gly-Dox SEQ ID NO: 46 dosed 10% higher than the efficacious dose tested in HT-29 model (Example 26) was not efficacious but still tolerated in the LNCaP model. Nonetheless, the relative lack of efficacy and toxicity at relatively high doses of Suc-Leu-Ala-Gly SEQ ID NO: 46 is consistent with the concept that CD10 plays an important role for in vivo cleavage of tumor activated prodrugs.

40 mg/kg and 67 mg/kg (42 mg/kg and 70 mg/kg doxorubicin equivalent concentration) was very well tolerated and greatly prolonged survival of tumor bearing mice. The doxorubicin treated mice had a MDS of 30 days. The Mean Day of Survival was increased to 39 and 41 days in the treated groups with Suc-Leu-Ala-Gly-Dox SEQ ID NO: 46, compared with 26 days in the vehicle control group. (Table 20). The high does of Suc-Leu-Ala-Gly-Dox SEQ ID NO: 46 decreased the rate of tumor growth significantly over the vehicle control group (Table 20). The compound was very well tolerated, suggesting that the administered doses were both below the repeat-dose MTD.

Therefore, we established a dose response and identified a big therapeutic window for Suc-Leu-Ala-Gly-Dox SEQ ID NO: 46 in the HT-29 model. HT-29 cells do not express CD10 in vitro and other enzymes, such as thimet oligopeptidase, might be responsible for Suc-Leu-Ala-Gly-Dox SEQ ID NO: 46 cleavage in HT-29 xenografts.

TABLE 20

| Compound | Dose (mg/kg) | Mean Tumor Weight at Day 14 (mg) | % TGI (Day 14, mean) | Median Tumor Weight at Day 25 (mg) | % TGI (Day 25, median) | Calculated Mean Day of Survival (day) | Extension of Mean Day of Survival over controls | Number of Long Term Survivors | Toxicity (Weight Loss >20%) |
|---|---|---|---|---|---|---|---|---|---|
| Saline | — | 733 ± 72 (n = 12) | 0% | 1515 | 0% | 25.7 ± 2.6 (n = 11) | 0% | 0/11 | 0/11 |

TABLE 20-continued

| Compound | Dose (mg/kg) | Mean Tumor Weight at Day 14 (mg) | % TGI (Day 14, mean) | Median Tumor Weight at Day 25 (mg) | % TGI (Day 25, median) | Calculated Mean Day of Survival (day) | Extension of Mean Day of Survival over controls | Number of Long Term Survivors | Toxicity (Weight Loss >20%) |
|---|---|---|---|---|---|---|---|---|---|
| Doxorubicin | 4.0 | 665 ± 103 (n = 10) | 9.3% | 1046 | 30.9% | 30.0 ± 3.7 (n = 9) | 16.7% | 0/10 | 1/10 |
| Suc-Leu-Ala-Gly-Dox SEQ ID NO: 46 | 40 | 704 ± 92 (n = 8) | 4.0% | 952 | 37.2% | 38.8 ± 6.6 (n = 7) | 51.0% | 1/7 | 0/7 |
| Suc-Leu-Ala-Gly-Dox SEQ ID NO: 46 | 67 | 490 ± 124 (n = 7) | 33.2%* | 857 | 43.5% | 41.3 ± 7.2 (n = 7) | 60.7%* | 3/7 | 0/7 |

*Statistically different from the control at the p level of 0.10 (two-tailed)
Some mice were excluded from tumor growth/survival analyses due to ulcerations of tumors.
TGI: Tumor Growth Inhibition over control Example 27

Susceptibility to Cleavage by Thimet Oligopeptidase and CD10 Compared to Efficacy To further evaluate the in vivo role of CD10 in tumor activated prodrug compound cleavage, doxorubicin containing prodrug compounds with distinct cleavage profiles for thimet oligopeptidase and CD10 were tested in LNCaP xenografts grown in C.B-17.5CID mice. Suc-βAla-Leu-Ala-Leu-Dox SEQ ID NO: 41, Suc-βAla-Ile-Ala-Leu-Dox SEQ ID NO: 39, Suc-Leu-Ala-Leu-Dox SEQ ID NO: 45, Suc-Ile-Ala-Leu-Dox SEQ ID NO: 42 and Suc-Leu-Ala-Gly-Dox SEQ ID NO: 46 were evaluated. All compounds except Suc-βAla-Leu-Ala-Leu-Dox SEQ ID NO: 41 (three levels) were dosed at two levels with the goal to get a dose response for all compounds. The cleavage profiles for each of the test compounds is shown in Table 21.

TABLE 21

| Compound | Cleaved by CD10 | Cleavage by thimet oligopeptidase |
|---|---|---|
| Suc-βAla-Leu-Ala-Leu-Dox SEQ ID NO: 41 | + | + |
| Suc-βAla-Ile-Ala-Leu-Dox SEQ ID NO: 39 | + | − |
| Suc-Leu-Ala-Leu-Dox SEQ ID NO: 45 | + | + |
| Suc-Ile-Ala-Leu-Dox SEQ ID NO: 42 | + | − |
| Suc-Leu-Ala-Gly-Dox SEQ ID NO: 46 | − | + |

TABLE 22

| | Dose Levels | |
|---|---|---|
| Compound | Dose (mg/Kg) | Equivalent Doxorubicin Dose (mg/kg) |
| Vehicle | — | — |
| Doxorubicin | 4 | 4 |
| Doxorubicin | 3 | 3 |
| Suc-βAla-Leu-Ala-Leu-Dox SEQ ID NO: 41 | 62 | 35 |
| Suc-βAla-Leu-Ala-Leu-Dox SEQ ID NO: 41 | 50 | 28 |
| Suc-βAla-Leu-Ala-Leu-Dox SEQ ID NO: 41 | 40 | 22 |
| Suc-βAla-Ile-Ala-Leu-Dox SEQ ID NO: 39 | 62 | 35 |
| Suc-βAla-Ile-Ala-Leu-Dox SEQ ID NO: 39 | 50 | 28 |
| Suc-Leu-Ala-Leu-Dox SEQ ID NO: 45 | 71 | 43 |
| Suc-Leu-Ala-Leu-Dox SEQ ID NO: 45 | 58 | 35 |
| Suc-Ile-Ala-Leu-Dox SEQ ID NO: 42 | 94 | 57 |
| Suc-Ile-Ala-Leu-Dox SEQ ID NO: 42 | 75 | 45 |
| Suc-Leu-Ala-Gly-Dox SEQ ID NO: 46 | 132 | 84 |
| Suc-Leu-Ala-Gly-Dox SEQ ID NO: 46 | 110 | 70 |

Knowing that the LNCaP tumor bearing nude mice have weight loss, we chose very conservative dose levels for each compound estimated to be well-tolerated equitoxic doses based on earlier studies and SD-MTD results. The high dose level for repeat dosing is usually 80% of their SD-MTD, and the low dose level is 80% of the high dose level. Accordingly, groups of ten male CD17.5CID mice, subcutaneously injected with 2.5 million LNCaP cells, were treated intravenously with the compounds at the levels described in Table 22 at six day intervals for a total of two identical doses (Q6DX2).

LNCaP tumors grew well in SCID mice, but the SCID mice with LNCaP tumor xenografts experienced severe weight loss, as 80% of control mice had more than 25% of weight loss by the end of the study. Nevertheless, the efficacy of different treatments at approximately equitoxic levels were compared based on the time it took for 50% of mice to reach toxic weight loss and the total numbers of mice with toxic weight loss at the end of study. The results of this comparison is shown in Table 23.

TABLE 23

| Compound | Dose (mg/kg) | Time: 50% Weight Loss (Day) | Time: 100% Weight Loss (Day) | % Weight Loss at the end of study | Growth Inhibition |
|---|---|---|---|---|---|
| Control | | 47 | | 80% | |
| Doxorubicin | 4 | 33 | | 80% | 29% |
| Doxorubicin | 3 | 36 | | 60% | 29% |
| Suc-βAla-Leu-Ala-Leu-Dox SEQ ID NO: 41 | 62 | 15 | 33 | | 65% |
| Suc-βAla-Leu-Ala-Leu-Dox SEQ ID NO: 41 | 50 | 19 | 40 | | 67% |
| Suc-βAla-Leu-Ala-Leu-Dox SEQ ID NO: 41 | 40 | 33 | 54 | | 47% |
| Suc-βAla-Ile-Ala-Leu-Dox SEQ ID NO: 39 | 62 | 12 | 33 | | 80% |
| Suc-βAla-Ile-Ala-Leu-Dox SEQ ID NO: 39 | 50 | 33 | | 80% | 60% |
| Suc-Leu-Ala-Leu-Dox SEQ ID NO: 45 | 70.5 | 26 | 47 | | 53% |
| Suc-Leu-Ala-Leu-Dox SEQ ID NO: 45 | 58.3 | 33 | 61 | | 56% |
| Suc-Ile-Ala-Leu-Dox SEQ ID NO: 42 | 94 | 19 | 36 | | 80% |
| Suc-Ile-Ala-Leu-Dox SEQ ID NO: 42 | 75 | 26 | 43 | | 73% |
| Suc-Leu-Ala-Gly-Dox SEQ ID NO: 46 | 132 | 29 | | 80% | 40% |
| Suc-Leu-Ala-Gly-Dox SEQ ID NO: 46 | 110 | 33 | | 80% | 40% |

The ranking of these compounds, from most effective to least effective, is: Suc-Ile-Ala-Leu-Dox SEQ ID NO: 42, Suc-βAla-Ile-Ala-Leu-Dox SEQ ID NO: 39, Suc-Leu-Ala-Leu-Dox SEQ ID NO: 45 and Suc-βAla-Leu-Ala-Leu-Dox SEQ ID NO: 41. Suc-Leu-Ala-Gly-Dox SEQ ID NO: 46 is more effective than doxorubicin and less effective than Suc-βAla-Ile-Ala-Leu-Dox SEQ ID NO: 39. As expected in view of CD10's inability to cleave Suc-Leu-Ala-Gly-Dox SEQ ID NO: 46 (see Example 2) and the lack of efficacy in vivo (see Example 25), Suc-Leu-Ala-Gly-Dox SEQ ID NO: 46 was not very active on LNCaP tumors.

Example 28

Pharmacokinetic/Metabolism Study

Six groups of ICR normal female mice were administered a single IV bolus dose with approximately 100 μmol/Kg of Suc-βAla-Leu-Ala-Leu-Dox SEQ ID NO: 41, Suc-βAla-Ile-Ala-Leu-Dox SEQ ID NO: 39, Suc-Leu-Ala-Leu-Dox SEQ ID NO: 45, Suc-Ile-Ala-Leu-Dox SEQ ID NO: 42, Suc-Leu-Ala-Gly-Dox SEQ ID NO: 46 or 10 μmol/Kg of doxorubicin (Dox). Plasma was obtained from three individual animals in each group at 5 minutes, 1, 2, 4, or 6 hr. Parent, dipeptidyl-doxorubicin (Ala-Leu-Dox, Ala-Gly-Dox), α-aminoacyl-doxorubicin (Leu-Dox or Gly-Dox) and doxorubicin concentrations were analyzed in extracts of the plasma samples using a reverse phase gradient HPLC method with fluorescence detection ($\lambda_{ex}$=480 nm, $\lambda_{em}$=560). The peak retention time of Ala-Gly-Dox was not confirmed because a standard was not available. Quantities were determined using a linear standard curve fit to measurements of 10 to 2000 ng/mL doxorubicin solutions in mouse plasma.

Figure 26:
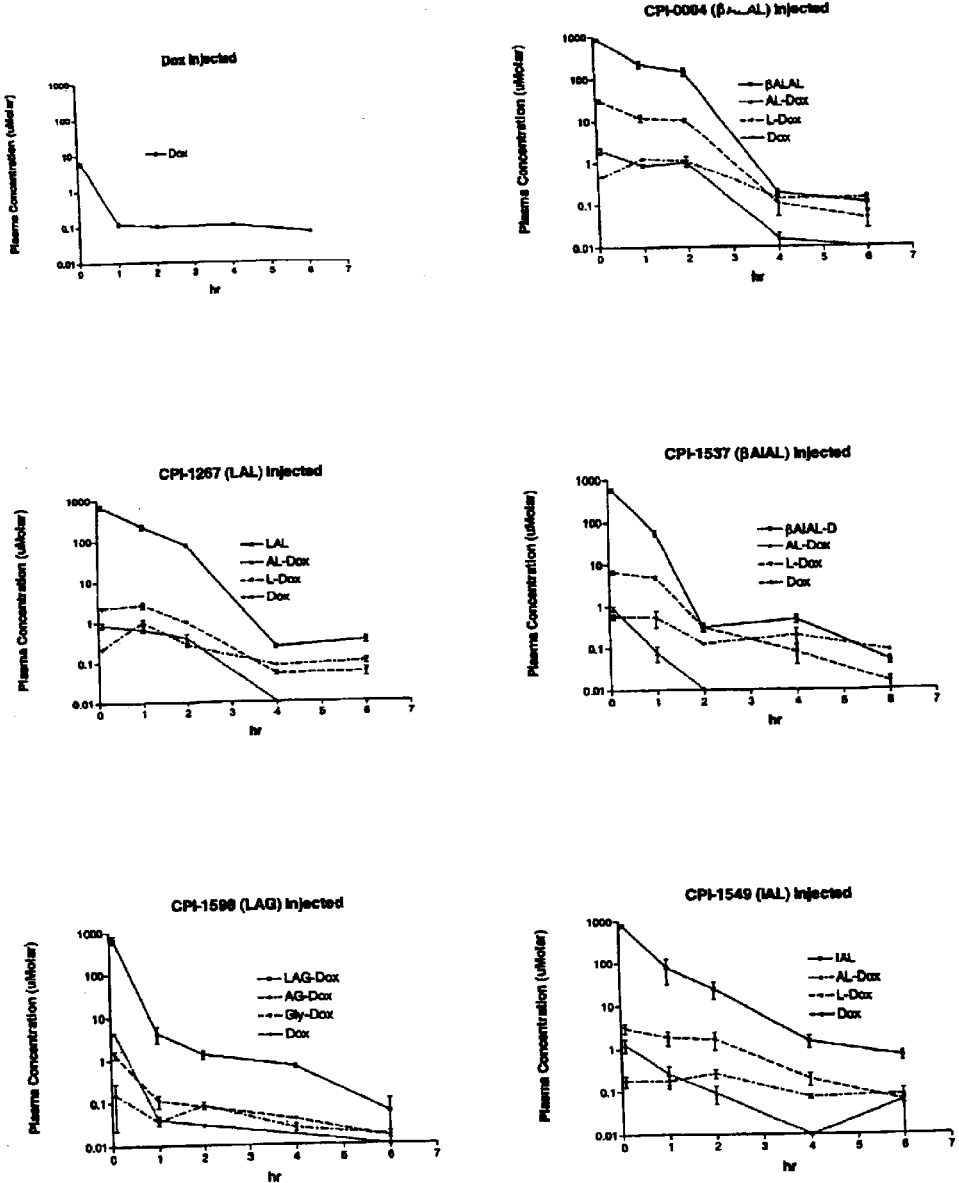
FIG. 26 is a graph of concentration of metabolites of Suc-βAla-Leu-Ala-Leu-Dox (SEQ ID NO: 41), Suc-βAla-Ile-Ala-Leu-Dox (SEQ ID NO: 39), Suc-Leu-Ala-Leu-Dox (SEQ ID NO: 45), Suc-Ile-Ala-Leu-Dox (SEQ ID NO: 42), Suc-Leu-Ala-Gly-Dox (SEQ ID NO: 46), and doxorubicin in plasma over time.

Concentration time courses (FIG. 26) indicate that metabolic patterns were similar for all compounds with the exception of Suc-Leu-Ala-Gly-Dox SEQ ID NO: 46, which is not cleaved by CD10. In particular, except for Suc-Leu-Ala-Gly-Dox SEQ ID NO: 46 Leu-Dox was the major metabolite over the first two hours, while the dipeptidyl-conjugate Ala-Leu-Dox was a more minor product that formed at about the same time as Leu-Dox. This is consistent with the cleavage pattern for CD 10. Doxorubicin appeared later with the plasma concentration decreasing more slowly over time than the other metabolites as expected from the current and previously measured doxorubicin pharmacokinetic (Van der Vijgh, "Comparative metabolism and pharmacokinetics of doxorubicin and 4'-epidoxorubicin in plasma, heart and tumor of tumorbearing mice," Cancer Chemother Pharmacol 26(1) 9–12 (1990); and Tabrizi-Fard, et al., "Evaluation of the Pharmacokinetic Properties of a Doxorubicin Prodrug in Female ICR(CD1®) Mice Following Intravenous Administration," Proc. Amer. Assoc. Cancer Res. 42:324 (2001)) and by the doxorubicin control group. Areas under the plasma concentration time curves (Table 24) indicate dosing with Suc-Leu-Ala-Gly-Dox SEQ ID NO: 46, the only peptidyl-conjugate not predicted to be cleaved by CD10, resulted in considerably less Dox exposure than the four CD10 cleavable peptidyl-doxorubicin compounds. Among the CD10 cleavable compounds, those which can also be cleaved by thimet oligopeptidase (Suc-βAla-Leu-Ala-Leu-Dox SEQ ID NO: 41 and Suc-Leu-Ala-Leu-Dox SEQ ID NO: 45) produced about two-fold greater doxorubicin exposure (AUC) than the corresponding non-compound with isoleucine substituted for leucine at the P1 position (Suc-βAla-Ile-Ala-Leu-Dox SEQ ID NO: 39 and Suc-Ile-Ala-Leu-Dox SEQ ID NO: 42 respectively). These isoleucine-substituted compounds are poorly or not cleaved by TOP. The two-fold decrease in AUC exposure to Dox is also observed with tripeptides compared to their corresponding tetrapeptide counterpart (Suc-βAla-Leu-Ala-Leu-Dox SEQ ID NO: 39 vs. Suc-Leu-Ala-Leu-Dox SEQ ID NO: 45 and Suc-βAla-Ile-Ala-Leu-Dox SEQ ID NO: 39 vs. Suc-Ile-Ala-Leu-Dox SEQ ID NO: 42). It should be noted that relative doxorubicin exposure after dosing these compounds resembles relative safety expressed as maximum tolerated dose in a mouse safety study. Thus a better profile of exposure to doxorubicin is achieved.

TABLE 24

Plasma exposure expressed as $AUC_{0-6hr}$ of parent and peptolytic metabolites

| Dosed Compound | Parent | AL-Dox or AG-Dox* | L-Dox or G-Dox* | Dox |
|---|---|---|---|---|
| | | ($\mu M \cdot hr$) | | |
| Suc-βAla-Leu-Ala-Leu-Dox SEQ ID NO: 41 | 806 | 3.2 | 40 | 3.4 |
| Suc-βAla-Ile-Ala-Leu-Dox SEQ ID NO: 39 | 326 | 0.5 | 8.5 | 1.5 |
| Suc-Leu-Ala-Leu-Dox SEQ ID NO: 45 | 634 | 1.6 | 5.1 | 1.6 |
| Suc-Ile-Ala-Leu-Dox SEQ ID NO: 42 | 452 | 1.0 | 6.2 | 0.9 |
| Suc-Leu-Ala-Gly-Dox SEQ ID NO: 46* | 310 | 2.1 | 0.9 | 0.3 |
| Doxorubicin (Dox) | N/A | N/A | N/A | 3.3 |

*metabolic products for Suc-Leu-Ala-Gly-Dox SEQ ID NO: 46 are Ala-Gly- Dox (identity not confirmed by standard), Gly-Dox and Dox.

These results are consistent with the hypothesis that normally occurring TOP in the body is a non-tumor activation mechanism for particular compounds which are also CD10 substrates. For compounds which are to be activated by tumor-related CD10 it may be preferable to design the oligopeptide to limit digestion by TOP since the data indicate about two times less Dox exposure when the compound is not a TOP substrate. Examples of such compounds are Suc-βAla-Ile-Ala-Leu-Dox SEQ ID NO: 39 and Suc-Ile-Ala-Leu-Dox SEQ ID NO: 42.

Example 29

Analysis of CD10 Transfected Chinese Hamster Ovary (CHO) Cell Lines

To provide direct evidence that CD10 can cleave peptide pre-drugs, CD10 transfectant cell lines were analyzed.

CD10 cDNA was cloned from a human fetal cDNA library by PCR using three sets of over-lapping primers:

```
                                      SEQ ID NO: 109
a5HindCD10  AAGCTTGCCGCCACCATGGGCAAGTCAGAAAGTCAGATG SEQ ID NO: 110
a3XbaCD10   TCTAGAAGGGAGGCCAAGTCGAGGTTGGTC SEQ ID NO: 111
b5XbaCD10   TCTAGAGATTACTATGAATGCACTGGAATC
```

```
                                      SEQ ID NO: 112
b3XhoCD10   CTCGAGGTACTCATTATTCAGTTTGTTATC

SEQ ID NO: 113
c5XhoCD10   CTCGAGTTGAACTACAAAGAAGATGAATAC

SEQ ID NO: 114
c3PacCD10   TTAATTAATCACCAAACCCGGCACTTCTTTTC
```

Figure 29:
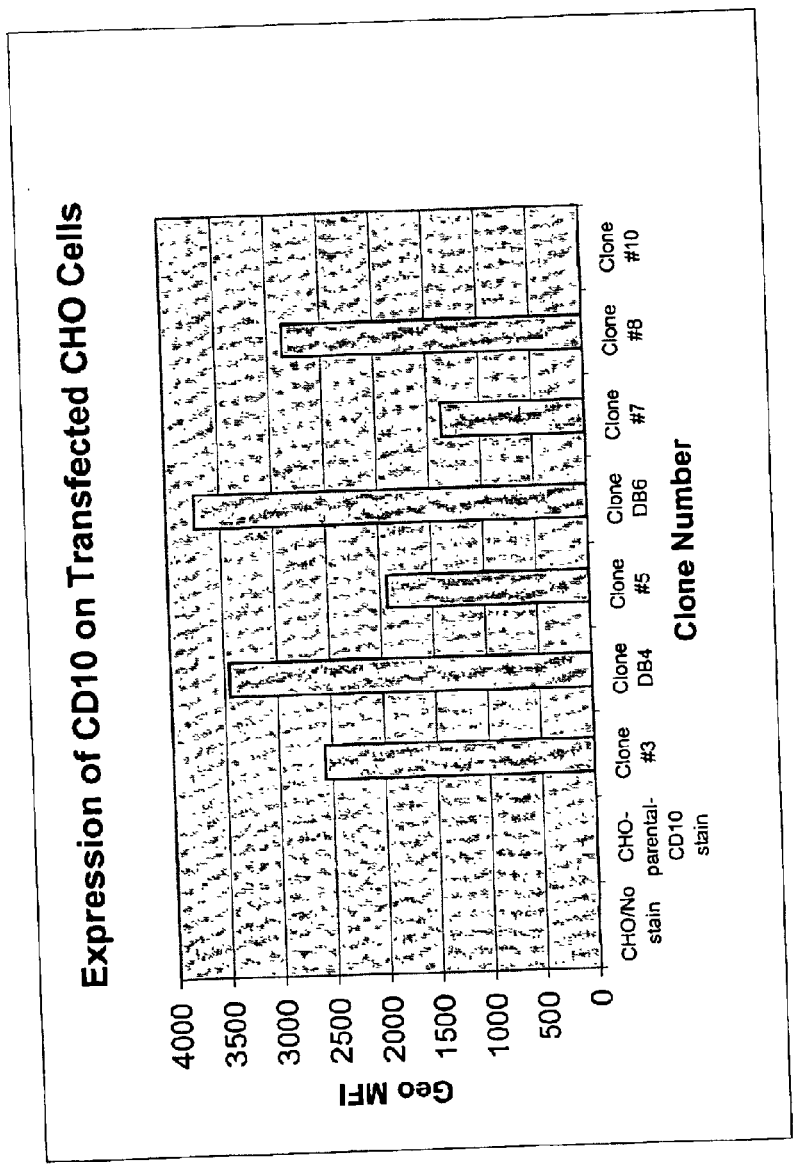
FIG. 29 illustrates the expression of CD10 on transfected CHO cells.

The fully assembled coding region was sub-cloned into a mammalian expression vector, downstream of the hCMV-MIE promoter. DNA sequence analysis confirmed sequence identity with the coding sequence of human CD10 (Genbank accession number Y00811). The expression plasmid was linearized and stably transfected into CHO—S cells. CD10 expressing transfectant clones were selected under 500 ug/mL of hygromycin and screened by flow cytometry for cell-surface CD10 expression using a commercially available anti-CD10-FITC antibody. FIG. 29 shows the geometric mean fluorescent intensity (Geo MFI) of transfectant CHO cell clones.

The clones were subsequently tested in a $^3H$ thymidine proliferation assay in the presence of doxorubicin (Dox), Suc-βAla-Ile-Ala-Leu-Dox SEQ ID NO: 39 or Suc-βAla-Leu-Ala-Leu-Dox SEQ ID NO: 41. CHO cells seem to be less sensitive to Doxorubicin as the average $IC_{50}$ value for Dox was 570 nM compared to 130 and 10 nM for LnCAP and Ramos cells, respectively (Table 25). Table 26 compares the activity of Suc-βAla-Ile-Ala-Leu-Dox SEQ ID NO: 39 to Dox. While the $IC_{50}$ for Dox and Suc-βAla-Ile-Ala-Leu-Dox SEQ ID NO: 39 on LnCAP (CD10 positive) differ by a factor of 3, a difference of 49 was observed with parental CHO cells. This number was reduced to ~16 fold with CD10 transfected CHO cells.

TABLE 25

3H Thymidine Proliferation assay with CD10 transfected CHO, parental CHO LnCAP and Ramos

| | $IC_{50}$ (mM) | | |
|---|---|---|---|
| | Doxorubicin | Suc-β-Ala-Leu-Ala-Leu SEQ ID NO: 41 | Suc-βAla-Ile-Ala-Leu SEQ ID NO: 39 |
| LnCap | 0.13 | 0.51 | 0.39 |
| Ramos | 0.01 | 0.84 | 0.44 |
| Parental CHO | 0.51 | 17.00 | 49.00 |
| DB4 | 0.31 | 5.40 | 4.20 |
| Clone #3 | 0.55 | 19.00 | 19.00 |
| Clone #5 | 0.81 | 24.00 | 19.00 |
| Clone #7 | 0.64 | 13.00 | 11.00 |
| Clone #8 | 0.57 | 10.00 | 8.40 |

TABLE 26

3H Thymidine proliferation assay with LnCAP, parental CHO and CD10 transfected CHO cells: Comparison of SucbAIAL and Dox IC50

| | $IC_{50}$ (mM) | | Ratio |
|---|---|---|---|
| | Doxorubicin | Suc-β-Ala-Ile-Ala-Leu SEQ ID NO: 41 | Suc-β-Ala-Ile-Ala-Leu/Dox SEQ ID NO: 39 |
| LnCap | 0.13 | 0.39 | 3 |
| Parental CHO | 0.51 | 49.00 | 96 |

TABLE 26-continued

3H Thymidine proliferation assay with LnCAP, parental CHO and CD10 transfected CHO cells: Comparison of SucbAIAL and Dox IC50

| | IC$_{50}$ (mM) | | Ratio |
|---|---|---|---|
| | Doxorubicin | Suc-β-Ala-Ile-Ala-Leu SEQ ID NO: 41 | Suc-β-Ala-Ile-Ala-Leu/Dox SEQ ID NO: 39 |
| Clone #7 | 0.64 | 11.00 | 17 |
| DB4 | 0.31 | 4.20 | 14 |
| Clone #8 | 0.57 | 8.40 | 15 |

To directly ask the question of whether the CD10 expressing cells were capable of cleaving the prodrug, supernatants from CD10 transfected or parental CHO cells treated with the compounds were collected. Parental CHO and CD10 transfected (clone 8) were incubated at 37° C. with 10 μM Suc-βAla-Leu-Ala-Leu-Dox SEQ ID NO: 41 (a substrate for CD10) or Suc-Leu-Ala-Gly-Dox SEQ ID NO: 46, which is not a substrate for CD10. After incubation for 1, 4, and 24 hours, an aliquot of each supernatant was transferred to a 96-well plate and frozen at −20° C. Samples were subsequently thawed and analyzed by reversed phase HPLC (4.6×50 mm 2μ TSK Super-ODS column) with fluorescence detection after dilution with 3 volumes of acetonitrile, removal of precipitate by centrifugation, and further dilution into 3 volumes of water. When incubated with Suc-βAla-Leu-Ala-Leu-Dox SEQ ID NO: 41, there was no detectable metabolism to Leu-Dox observed with the parental cell line while clone 8 (CD10 transfected) generated significant levels of Leu-Dox from Suc-βAla-Leu-Ala-Leu-Dox SEQ ID NO: 41 (Table 27). CD10 transfected CHO cells did not provide significantly enhanced rates of cleavage of Suc-Leu-Ala-Gly-Dox SEQ ID NO: 46 compared with non-transfected CHO cells, consistent with the suggestion that this peptide pro-drug is a poor substrate for CD10.

TABLE 27

Conversion rates to Leu-Dox or Gly-Dox

| | Suc-βAla-Leu-Ala-Leu Dox SEQ ID NO: 41 | | Suc-Leu-Ala-Gly-Dox SEQ ID NO: 46 | |
|---|---|---|---|---|
| Substrate | Parental | Clone 8 | Parental | Clone 8 |
| Percent Conversion/Hour | 0 | 3.00 | 0.57 | 0.61 |
| mM/hour | 0 | 0.30 | 0.06 | 0.06 |

To confirm that the CD10 expressing CHO cells were capable of cleaving suc-βAla-Ile-Ala-Leu-Dox SEQ ID NO: 39, supernatants were collected 24 hours after exposure to each of the following compounds: Dox, Suc-βAla-Ile-Ala-Leu-Dox SEQ ID NO: 39 and Suc-Leu-Ala-Gly-Dox SEQ ID NO: 46. The supernatants were transferred to Dox sensitive HL60 cells (CD10 negative) and cell proliferation was measured 24 hours later. ³H Thymidine proliferation data shows that while supernatants from parental CHO or CD10 negative CHO cells did not inhibit proliferation in the presence of Suc-βAla-Ile-Ala-Leu-Dox SEQ ID NO: 39, two representative CD10 positive CHO cells did (Table 28). As an additional control, fresh Dox, Suc-βAla-Ile-Ala-Leu-Dox SEQ ID NO: 39 and Suc-Leu-Ala-Gly-Dox SEQ ID NO: 46 were added to HL60 and IC$_{50}$ measurements were made 24 hours later. When compounds are added fresh to HL60 cells (CD10 negative), cleavage of Suc-βAla-Ile-Ala-Leu-Dox SEQ ID NO: 39 does not occur again indicating that CD10 is required for cleavage. Confirmation of the data is shown when Suc-βAla-Leu-Ala-Leu-Dox SEQ ID NO: 41 was compared to Suc-Leu-Ala-Gly-Dox SEQ ID NO: 46 and the results are consistent with the fact that Suc-βAla-Leu-Ala-Leu SEQ ID NO: 41 is cleaved by CD10 transfected cells and not by the parental cell lines.

TABLE 28

Proliferation of HL60 cells in the presence of supernatant collected from parental CHO and CD10 positive CHO cells treated with compounds

| | IC$_{50}$ (μM) | | |
|---|---|---|---|
| | Dox | Suc-βAla-Ile-Ala-Leu SEQ ID NO: 39 | Leu-Ala-Gly-Dox SEQ ID NO: 46 |
| Parental CHO | 0.279 | >25 | >25 |
| Clone 10 (CD10 Neg.) | 0.417 | >25 | >25 |
| Clone DB4 (CD10 Pos.) | 0.491 | 5.4 | >25 |
| Clone 8 (CD10 Pos.) | 0.488 | 2.7 | >25 |
| HL60 fresh compound | 0.164 | >50 | >50 |

In summary, the data show that CD10 can cleave the prodrug Suc-βAla-Leu-Ala-Leu-Dox SEQ ID NO: 41 or Suc-βAla-Ile-Ala-Leu-Dox SEQ ID NO: 39 to release Leu-Dox.

Example 30

Comparison of Tumor Growth Inhibition by Suc-βAla-Leu-Ala-Leu-Dox and Doxorubicin in the Doxorubicin-Sensitive LNCaP Prostate Carcinoma Model A comparison of the relative efficacy of tumor inhibition of Suc-βAla-Leu-Ala-Leu-Dox SEQ ID NO: 41 versus doxorubicin in a CD10-positive tumor cell line (LNCaP) was performed to establish a comparable dose response and therapeutic index.

In this model, 7.5 million LNCaP cells resuspended in 0.1 ml of phosphate buffered saline and 0.1 ml of Matrigel (Becton Dickinson) were injected into the side of male nude mice fed on high fat diet. Dosing was initiated when the mean tumor weight reached approximately 200 mg and the dose regimens are summarized in Table 29.

Efficacy

Figure 30:
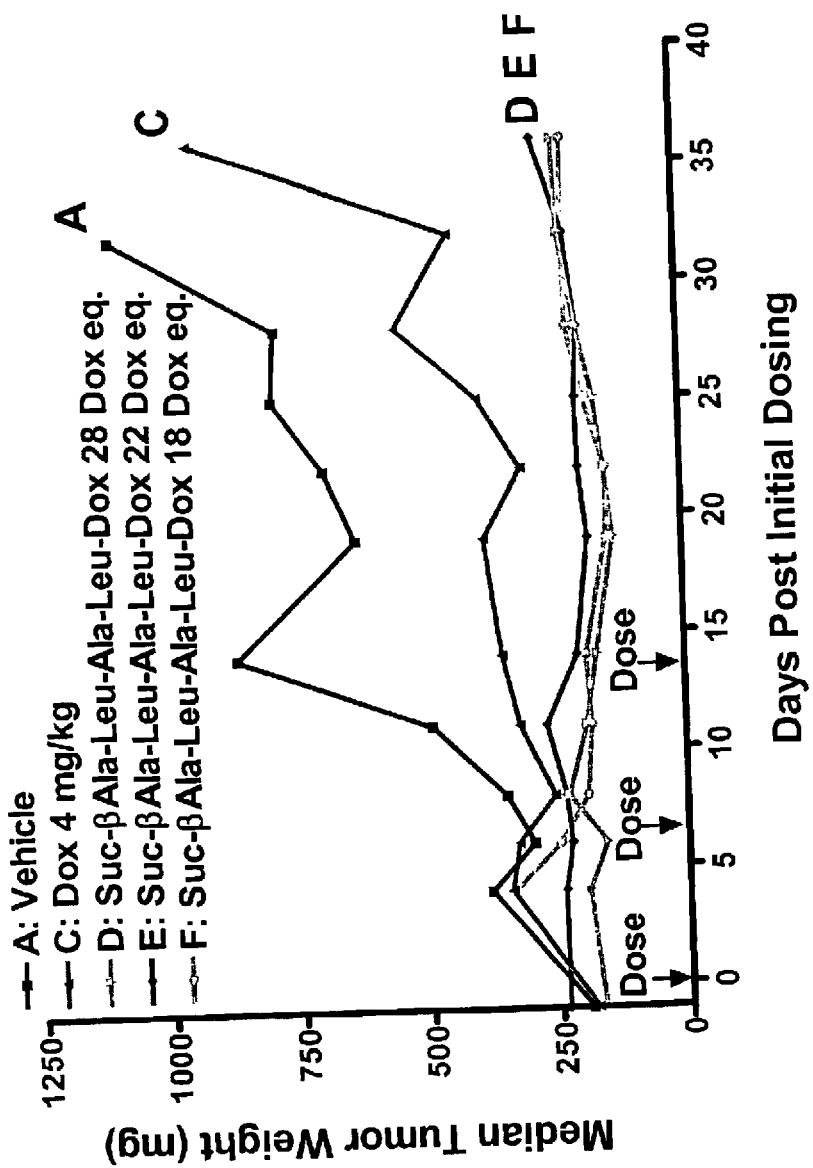
FIG. 30 is a graph of growth of LNCaP tumors in nude mice treated with Suc-βAla-Leu-Ala-Leu-Dox (SEQ ID NO: 41), doxorubicin, or vehicle.
Figure 31:
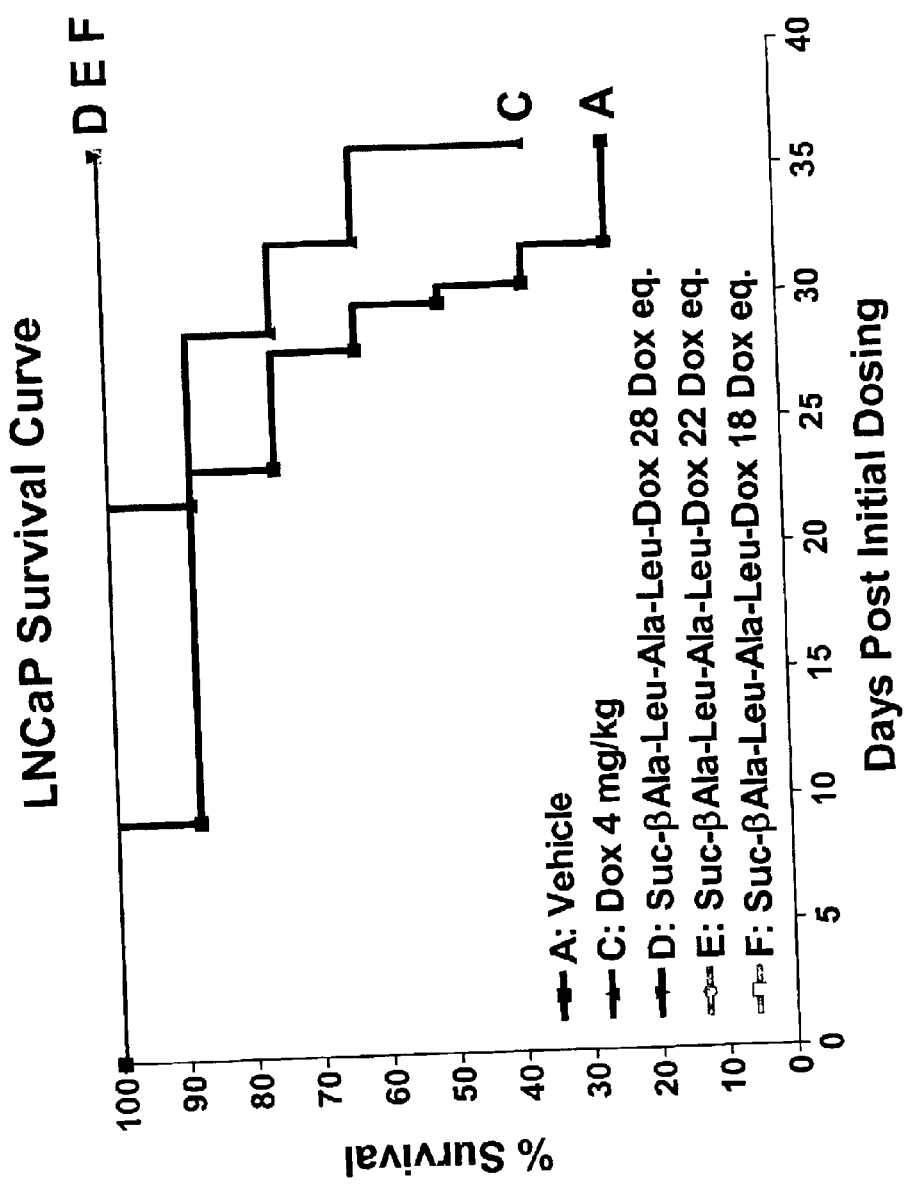
FIG. 31 is a graph of survival rate of nude mice containing xenografted LNCaP tumors treated with Suc-βAla-Leu-Ala-Leu-Dox (SEQ ID NO: 41), doxorubicin, or vehicle.

Suc-βAla-Leu-Ala-Leu-Dox SEQ ID NO: 41 at all three dose levels (molar equivalent of 18, 22 & 28 mg doxorubicin/kg) significantly inhibited tumor growth at Day 22, the last day of measurement on which all mice were alive (FIG. 30 and Table 29). No trend of dose-related increase in efficacy of Suc-βAla-Leu-Ala-Leu-Dox SEQ ID NO: 41 was observed, as the efficacy was maximal by 18 mg/kg Dox eq (FIG. 30). In addition, all three doses of Suc-βAla-Leu-Ala-Leu-Dox SEQ ID NO: 41 significantly inhibited tumor growth to a greater extent than doxorubicin dosed at 4 mg/kg. Doxorubicin at this dosing failed to achieve statistical significance from the control (Table 29). No tumors reached the >1 g predetermined cancer endpoint in all three dose groups of Suc-βAla-Leu-Ala-Leu-Dox SEQ ID NO: 41 (FIG. 31). Therefore, Suc-βAla-Leu-Ala-Leu-Dox SEQ ID NO: 41, but not doxorubicin, significantly prolonged survival of tumor-bearing mice compared to the control group (Table 29).

Toxicity

Figure 32:
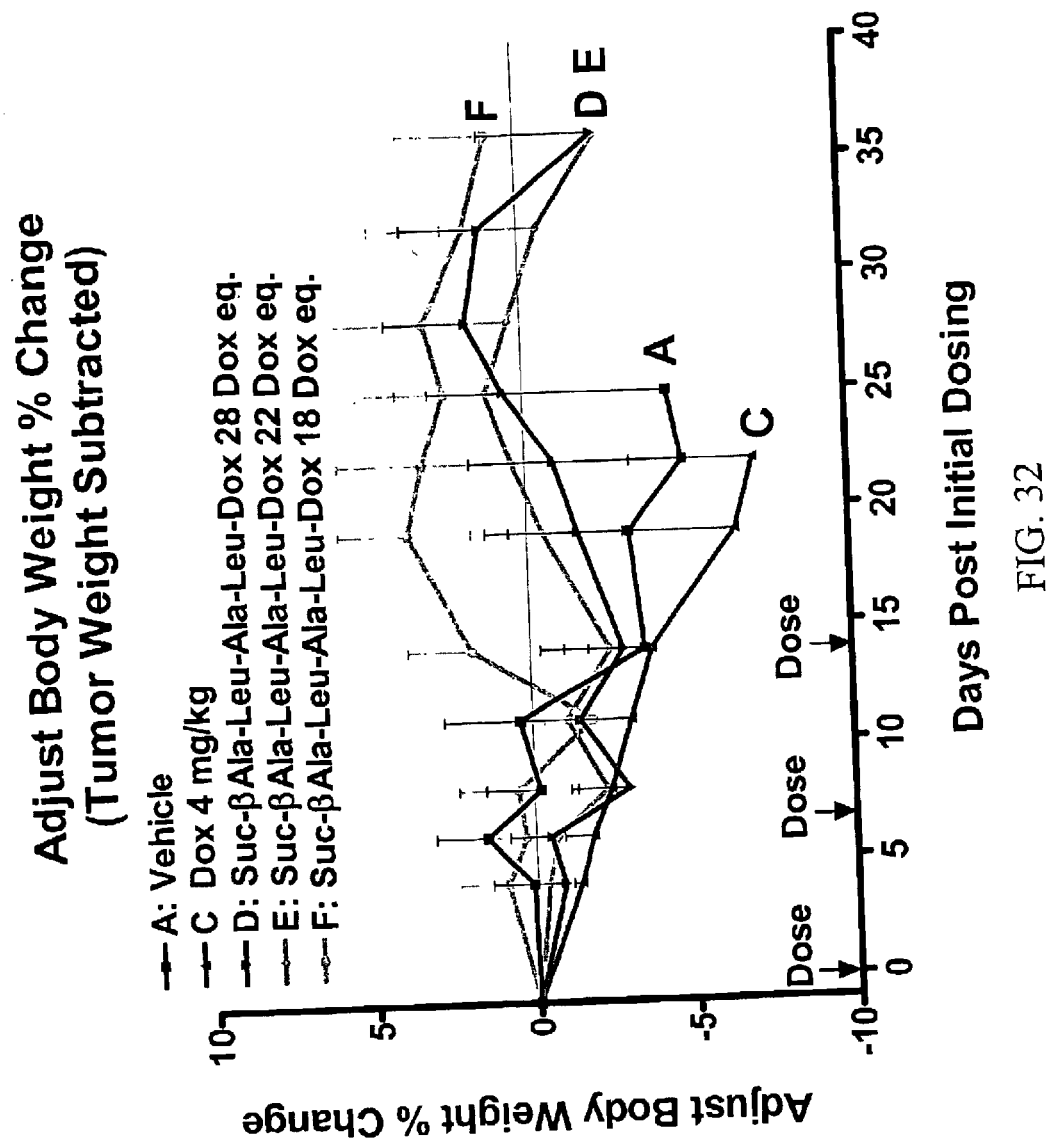
FIG. 32 is a graph of group mean adjusted body weight of nude mice containing xenografted LNCaP tumors treated with Suc-βAla-Leu-Ala-Leu-Dox (SEQ ID NO: 41), doxorubicin, or vehicle.

Furthermore, all three doses of Suc-βAla-Leu-Ala-Leu-Dox SEQ ID NO: 41 were very well tolerated with no toxic endpoints when the study was terminated at Day 36 and with maximal 3% loss of group mean adjusted body weight (tumor weight subtracted) (FIG. 32). Mice receiving 4 mg/kg of doxorubicin had one toxic endpoint (>20% weight loss) on Day 22 and about 7% loss of group mean adjusted body weight on Day 22. Control group mice also had slight weight loss (up to 5% loss of group mean adjusted body weight), and two toxic endpoints which could be a result of tumor growth (Table 29).

Example 31

Comparison of Tumor Growth Inhibition by Suc-βAla-Leu-Ala-Leu-Dox and Tripeptides Suc-βAla-Ile-Ala-Leu-Dox & Suc-Leu-Ala-Gly-Dox in the Doxorubicin-Sensitive LNCaP Prostate Carcinoma Model To further evaluate the in vivo roles of extracellular CD10 versus TOP (thimet oligopeptidase) in tumor activated prodrug compound cleavage, doxorubicin-containing prodrug compounds with distinct cleavage profiles for CD10 were tested in CD10 positive LNCaP xenografts grown in nude mice.

Suc-βAla-Leu-Ala-Leu-Dox SEQ ID NO: 41, a substrate for both TOP and CD10, and Suc-βAla-Ile-Ala-Leu-Dox

TABLE 29

Tumor Growth Inhibition and Survival Rates in LNCaP Prostate Carcinoma Xenograft Model

| Group | Compound | Dose # (mg/kg) | N | Tumor Weight (mg) | TGI | Survivor | Cancer Endpoint | Toxic Endpoint |
|---|---|---|---|---|---|---|---|---|
| A | Saline | – | 8 | D22: 677.4 ± 185.2 | – | D36: 2 | 4 | 2 |
| C | Doxorubicin | 4 | 8 | D22: 323.8 ± 60.8 | D22: 52.2 ± 28.8% | D36: 3 | 4 | 1 |
| D | Suc-βAla-Leu-Ala-Leu-Dox SEQ ID NO: 41 | 50 (28* Dox equi) | 8 | D22: 143.4 ± 19.0 | D22: 78.8 ± 27.5%* | D36: 8** | 0 | 0 |
| E | Suc-βAla-Leu-Ala-Leu-Dox SEQ ID NO: 41 | 40 (22* Dox equi) | 8 | D22: 180.1 ± 19.7 | D22: 73.4 ± 27.5%* | D36: 8** | 0 | 0 |
| F | Suc-βAla-Leu-Ala-Leu-Dox SEQ ID NO: 41 | 32 (18* Dox equi) | 8 | D22: 116.3 ± 30.2 | D22: 82.8 ± 27.7%* | D36: 8** | 0 | 0 |

All compounds were dosed Q7Dx3
Statistically different from the control and doxorubicin group (*p < 0.05; **p < 0.01)

Parmeters evaluated include (1) mean tumor weight at Day 22, the last time point before the first mouse reaching cancer and/or toxic endpoint; (2) TGI(tumor growth inhibition at Day 22 percent mean tumor weight inhibition over control); (3) Survivors at Day 36, (4) tumors reaching the predetermined cutoff size of 1000 mg (cancer endpoint), and (5) tolerability of the dosing regimen, by number of mice exhibiting toxic endpoint (>20% body weight loss).

In summary, in this slow-growing, doxorubicin-sensitive LNCaP model, all three doses of Suc-βAla-Leu-Ala-Leu-Dox SEQ ID NO: 41 significantly inhibited tumor growth, extended mouse survival and were very well tolerated (FIGS. 30–32). Suc-βAla-Leu-Ala-Leu-Dox SEQ ID NO: 41 is significantly better than approximately equitoxic doses of doxorubicin in inhibiting the growth of a slow-growing, relatively doxorubicin-sensitive prostate tumor. Doxorubicin dosed at around its maximum tolerated dose (one out of eight mice lost weight and reached the toxic endpoint on Day 22) was effective on the tumor but failed to achieve statistical significance from the control in tumor growth inhibition or survival extension. Therefore, Suc-βAla-Leu-Ala-Leu-Dox SEQ ID NO: 41 at all three levels significantly inhibited LNCaP tumor growth better than doxorubicin and a relatively wide therapeutic window was identified for Suc-βAla-Leu-Ala-Leu-Dox SEQ ID NO: 41 in the LNCaP human prostate tumor model. Furthermore, because of its sensitivity to doxorubicin, the model described in this example serves as a good indicator of release of doxorubicin from the remainder of the prodrug molecule.

Figure 33:
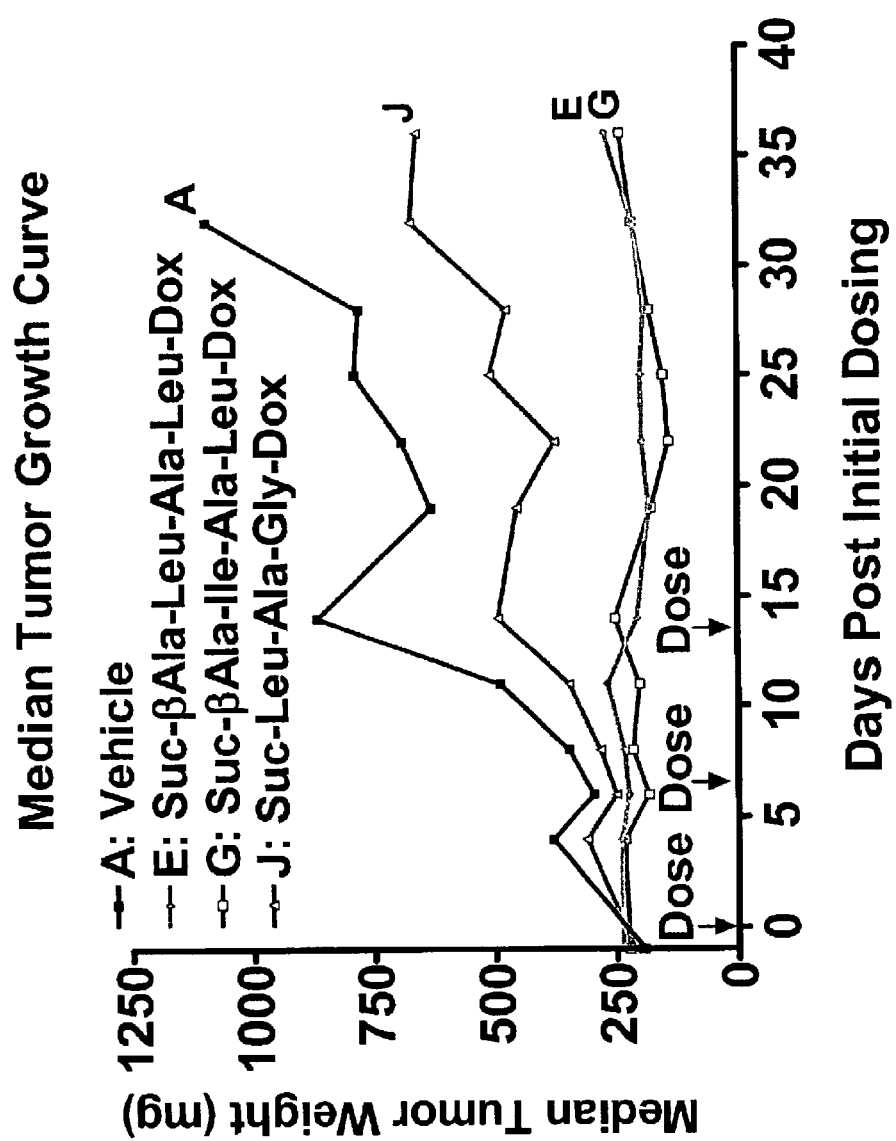
FIG. 33 is a graph of growth of LNCaP tumors in nude mice treated with Suc-βAla-Leu-Ala-Leu-Dox (SEQ ID NO: 41), Suc-βAla-Ile-Ala-Leu-Dox (SEQ ID NO: 39), Suc-Leu-Ala-Gly-Dox (SEQ ID NO: 46), or vehicle.
Figure 34:
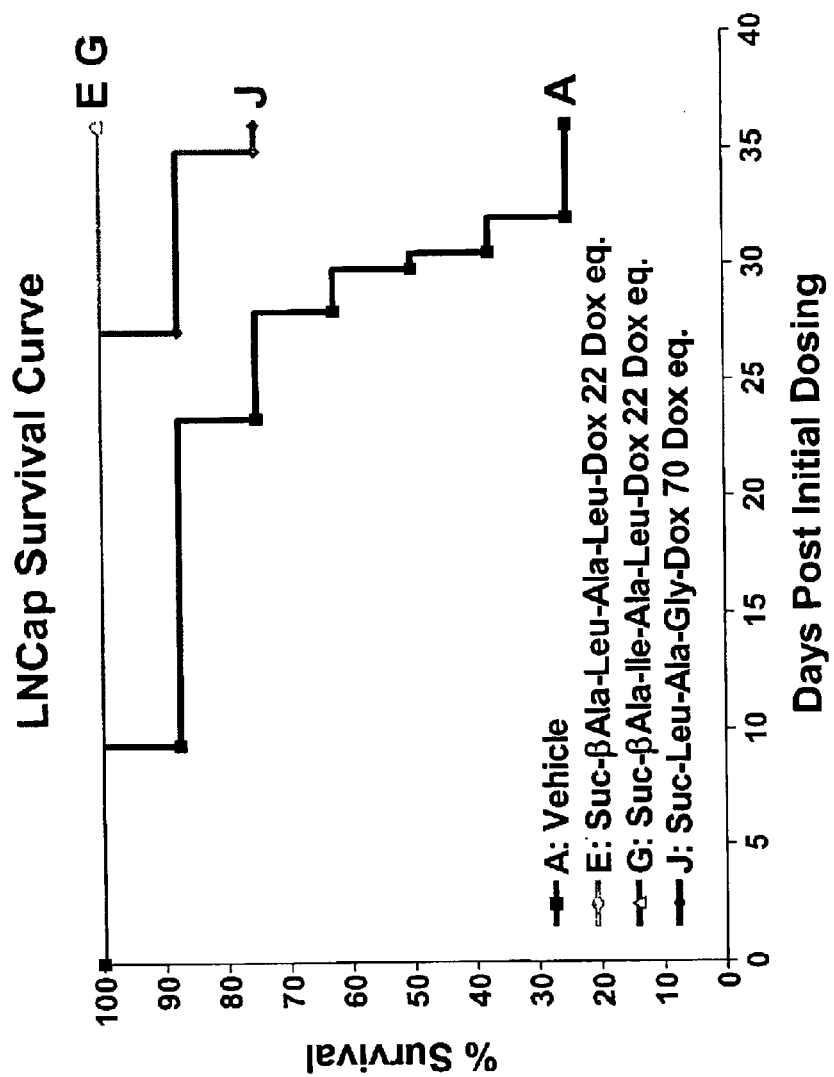
FIG. 34 is a graph of survival rate of nude mice containing xenografted LNCaP tumors treated with Suc-βAla-Leu-Ala-Leu-Dox (SEQ ID NO: 41), Suc-βAla-Ile-Ala-Leu-Dox (SEQ ID NO: 39), Suc-Leu-Ala-Gly-Dox (SEQ ID NO: 46), or vehicle.
Figure 35:
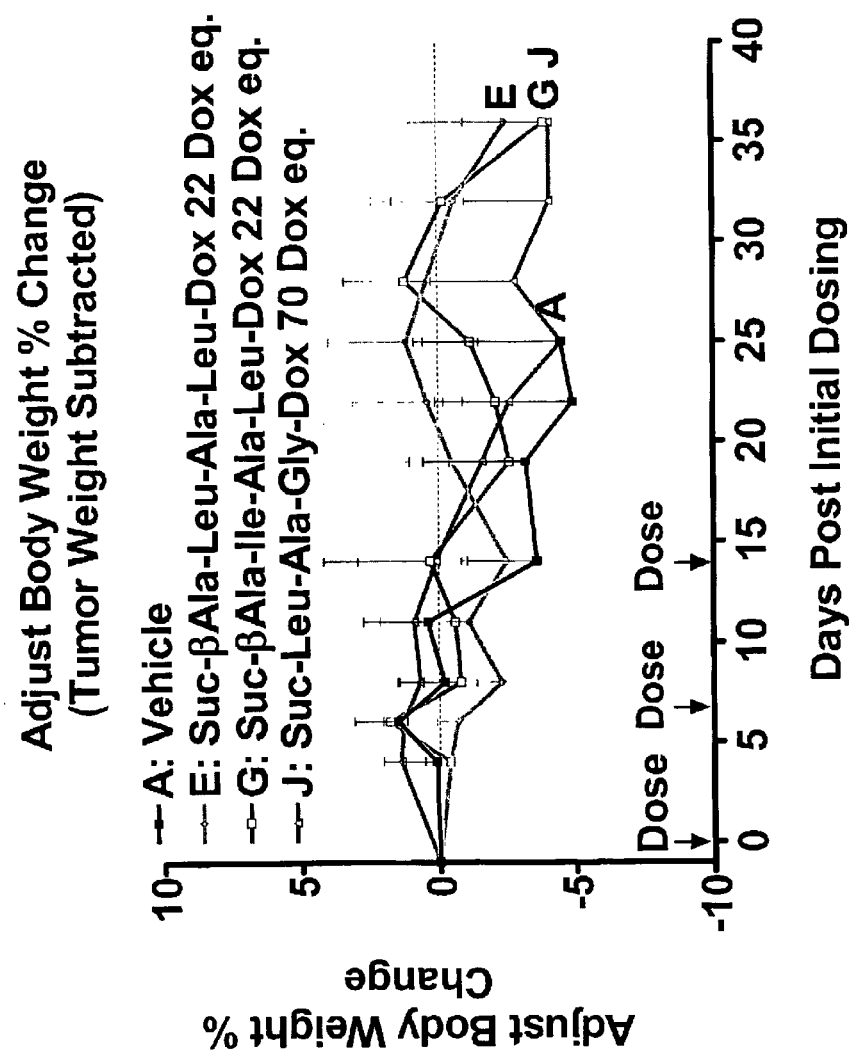
FIG. 35 is a graph of group mean adjusted body weight of nude mice containing xenografted LNCaP tumors treated with Suc-βAla-Leu-Ala-Leu-Dox (SEQ ID NO: 41), Suc-βAla-Ile-Ala-Leu-Dox (SEQ ID NO: 39), Suc-Leu-Ala-Gly-Dox (SEQ ID NO: 46), or vehicle.

SEQ ID NO: 39, a substrate for CD10, but a weaker substrate for TOP, were dosed equimolarly at 22 mg/kg Dox eq. Q7Dx3. Suc-Leu-Ala-Gly-Dox SEQ ID NO: 46, a substrate for TOP only, although a comparatively weaker substrate than Suc-βAla-Leu-Ala-Leu-Dox SEQ ID NO: 41 was dosed at 70 mg/kg Dox eq. Q7Dx3 (a level that is three times greater than the molar concentration dosage of Suc-βAla-Leu-Ala-Leu-Dox SEQ ID NO: 41 and Suc-βAla-Ile-Ala-Leu-Dox SEQ ID NO: 39). Suc-βAla-Leu-Ala-Leu-Dox SEQ ID NO: 41 and Suc-βAla-Ile-Ala-Leu-Dox SEQ ID NO: 39 greatly inhibited tumor growth (FIG. 33) and achieved over 70% TGI (tumor growth inhibition) on Day 22 compared to the control group (Table 30), a statistically significant increase in inhibition. Suc-Leu-Ala-Gly-Dox SEQ ID NO: 46 dosed at three times the molar concentration of Suc-βAla-Ile-Ala-Leu-Dox SEQ ID NO: 39, inhibited tumor growth to a lesser extent than Suc-βAla-Ile-Ala-Leu-Dox SEQ ID NO: 39 (TGI D22:39.7+29.5% vs. 77.5+ 27.5%) and failed to achieve statistical significance from control (Table 30). In addition, no tumors reached the >1 g predetermined cancer endpoint in both the Suc-βAla-Leu-Ala-Leu-Dox SEQ ID NO: 41 and the Suc-Leu-Ala-Gly-Dox SEQ ID NO: 46 groups (FIG. 34). All three compounds were very well tolerated with no toxic endpoints when the study was terminated at Day 36 (FIG. 35).

TABLE 30

Tumor Growth Inhibition and Survival Rates in LNCaP Prostate Carcinoma Xenograft Model

| Group | Compound | Dose # (mg/kg) | N | Tumor Weight (mg) | TGI | Survivor | Cancer Endpoint | Toxic Endpoint |
|---|---|---|---|---|---|---|---|---|
| A | Saline | – | 8 | D22: 677.4 ± 185.2 | – | D36: 2 | 4 | 2 |
| E | Suc-βAla-Leu-Ala-Leu-Dox SEQ ID NO: 41 | 40 (22* Dox equi) | 8 | D22: 180.1 ± 19.7 | D22: 73.4 ± 27.5%* | D36: 8** | 0 | 0 |
| G | Suc-βAla-Ile-Ala-Leu-Dox SEQ ID NO: 39 | 40 (22* Dox equi) | 8 | D22: 152.1 ± 19.3 | D22: 77.5 ± 27.5%* | D36: 8** | 0 | 0 |
| J | Suc-Leu-Ala-Gly-Dox SEQ ID NO: 46 | 110 (70* Dox equi) | 8 | D22: 408.8.1 ± 75.7 | D22: 39.7 ± 29.5% | D36: 6* | 2 | 0 |

All compounds were dosed Q7Dx3
Statistically different from the control and doxorubicin group (*p < 0.05; **p < 0.01)

Parameters evaluated include (1) mean tumor weight at Day 22, the last time point before the first mouse reaching cancer and/or toxic endpoint; (2) TGI (tumor growth inhibition at Day 22 percent mean tumor weight inhibition over control); (3) Survivors at Day 36, (4) tumors reaching the predetermined cutoff size of 1000 mg (cancer endpoint), and (5) tolerability of the dosing regimen, by number of mice exhibiting toxic endpoint (>20% body weight loss).

The dose efficacy response differentiation of Suc-βAla-Ile-Ala-Leu-Dox SEQ ID NO: 39 vs Suc-Leu-Ala-Gly-Dox SEQ ID NO: 46 strongly supports the critical in vivo role of CD10 in tumor activated prodrug compound cleavage in CD10$^+$ LNCaP tumors. That Suc-βAla-Leu-Ala-Leu-Dox SEQ ID NO: 41 and Suc-βAla-Ile-Ala-Leu-Dox SEQ ID NO: 39 have similar efficacy on LNCaP xenografts suggests that CD10 plays a more dominant role than TOP in tumor activated prodrug compound cleavage in CD10$^+$ LNCaP tumors.

Analytical Methods for the Remaining Examples

The peptide sequences, synthesized using either solid or solution phase approaches, were used without further purification if the analytical HPLC (methods A, B & D) showed the crude product to be greater than 80% pure. If the crude product was not greater than 80% pure, the product was further purified using preparative HPLC Method C.

HPLC Method A

Analytical HPLC analyses were performed on a Waters 2690 using a C-18 column (4 μm, 3.9×150 mm ID, flow rate 1 mL/min) eluting with a gradient of solvent A (0.1% TFA/H$_2$O) and solvent B (0.1% TFA/ACN) and the data was processed at λ254 nm using the Waters Millennium system. Analytical HPLC gradient started with 90% of solvent A and ended with 100% of solvent B over a period of 14 minutes (linear). Purity of the compounds for this method and the following ones was assessed as the relative percentage area under the curve of the peaks.

HPLC Method B

Analytical HPLC analyses were performed on a Waters 2690 using a C-8 column (3.5 μm, 4.6×150 mm ID, flow rate 1 mL/min) eluting with a gradient of solvent A (80% 20 mM ammonium formate and 20% acetonitrile) and solvent B (20% 20 mM ammonium formate and 80% acetonitrile) and the data was processed at λ254 nm using the Waters Millennium system. Analytical HPLC gradient started with 100% of solvent A to 100% of solvent B over a period of 30 minutes (linear).

HPLC Method C

Preparative purification of crude products was achieved using a Waters Delta Prep 4000 system using a C-4 column (15 μm, 40×100 mm ID, flow rate 30 mL/min) eluting with a gradient of solvent A (H$_2$O), and solvent B (MeOH). The preparatory HPLC gradient started with 80% of solvent A and goes to 100% of solvent B over a period of 70 minutes (linear). UV detection was at λ254 nm.

HPLC Method D

Analytical HPLC was accomplished on a Hewlett Packard instrument using a TSK superODS column (TosoHaas); solvent A (TFA 0.1% in water); solvent B (TFA 0.1% in acetonitrile); gradient: 30 to 36% of B in 2 minutes, 36 to 41% of B in 10 minutes, 41 to 90% of B in 3 minutes, 5 minutes at 90% B, detection wavelength λ 254 nm.

NMR and MS

Additional structural determinations were done by NMR and MS techniques and the results supported the claimed compounds.

TLC Method

TLC analysis was carried out on silica gel 60F-254 nm-0.25 mm plates (Merck) with DCM/MeOH/H$_2$O/Formic acid 88% 85/15/1/2 for elution.

Ninhydrin Test

A few milligrams of product were introduced in a test tube, and two drops of Solution A (50 mg/mL ninhydrin in ethanol), two drops of Solution B (4 mg/mL phenol in ethanol), then two drops of Solution C (2 mL 0.01M KSCN, aqueous in 100 mL pyridine) were added. The mixture was left in a boiling water bath for five minutes. In the presence of a free amine the solution becomes purple.

Specific Oligopeptide Synthetic Examples
Sources of Commercially Available Reagents Doxorubicin and Daunorubicin were supplied by Meiji (Japan), Pd(PPh$_3$)$_4$ by Strem chem (Newburyport, Mass.), PEG by Shearwater (Huntsville, Ala.), solvents, HATU by Aldrich (Milwaukee, Wis.); all resins and amino acids were supplied by ABI (Foster City, Calif.), Novabiochem (San Diego, Calif.), Advanced ChemTech (Louisville, Ky.), Peptide International (Louisville, Ky.), or SynPep (Dublin, Calif.).

Example 32

Synthesis of Fmoc-Ile-Ala-Leu-OH

Tripeptide (Fmoc-Ile-Ala-Leu-OH) was synthesized using solid-phase approach with standard Fmoc chemistry. A typical synthesis used Wang's alkoxy resin (0.60 mmol/gm loading). Fmoc-protected amino acids were used for solid-phase peptide synthesis.

For a scale of 1 mM peptide on resin, 3 equivalents of amino acid was pre-activated with HBTU as the activating agent for 5 minutes before being added to the resin together with 2 equivalents of DIEA. The coupling reaction was carried out for 2 h and then washed with DMF (25 mL×3) and DCM (25 mL×3). The coupling reaction was repeated using 2 equivalents of amino acid using similar conditions. The reaction progress was monitored using ninhydrin test and if the ninhydrin test indicated incomplete reaction after 2 h then the coupling step was repeated for a third time. Deprotection was accomplished using 20% piperidine in DMF for 15–20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at rt, the resin was filtered under reduced pressure and washed twice with TFA. Filtrates were combined and the peptide was precipitated by adding 400 mL of cold ether. The peptide was filtered under reduced pressure and dried to yield Fmoc-Ile-Ala-Leu-OH (92% HPLC purity by method A). Crude peptide was characterized by LC/MS and used for the next step without any further purification.

Example 33

Synthesis of Fmoc-β-Ala-Ile-Ala-Leu-OH

Tetrapeptide (Fmoc-β-Ala-Ile-Ala-Leu-OH SEQ ID NO: 37) was synthesized using solid-phase approach with standard Fmoc chemistry. A typical synthesis used Wang's alkoxy resin (0.60 mmol/gm loading). Fmoc-protected amino acids were used for solid-phase peptide synthesis. For a scale of 1 mM peptide on resin, 3 equivalents of amino acid was pre-activated with HBTU as the activating agent for 5 minutes before being added to the resin together with 2 equivalents of DIEA. The coupling reaction was carried out for 2 h and then washed with DMF (25 mL×3) and DCM (25 mL×3). The coupling reaction was repeated using 2 equivalents of amino acid using similar conditions. The reaction progress was monitored using ninhydrin test and if the ninhydrin test indicated incomplete reaction after 2 h then the coupling step was repeated for a third time. Deprotection was accomplished using 20% piperidine in DMF for 15–20 minutes. The coupling step was repeated with the next amino acid until the desired peptide was assembled on resin. The final cleavage of peptide from the resin was accomplished by treating the resin with a solution of 95% TFA and 5% water. After stirring the reaction mixture for 2 h at rt, the resin was filtered under reduced pressure and washed twice with TFA. Filtrates were combined and the peptide was precipitated by adding 400 mL of cold ether. The peptide was filtered under reduced pressure and dried to yield Fmoc-β-Ala-Ile-Ala-Leu-OH SEQ ID NO: 37 (92% HPLC purity by method A). Crude peptide was characterized by MS and used for the next step without any further purification.

Example 34

Synthesis of Fmoc-Ile-Ala-Leu-Dox

Doxorubicin.HCl (2.34 g, 4.03 mmol) and Fmoc-Ile-Ala-Leu-OH SEQ ID NO: 115 (2.4 g, 4.48 mmol) were dissolved at room temperature in anhydrous DMF (150 mL). To this rapidly stirred solution, DIEA (1.56 mL, 8.96 mmol) was added in one portion and the reaction mixture was stirred for 15 minutes at room temperature. The reaction mixture was cooled to 0° C. using an ice bath and 1.87 g (4.92 mmol) of HATU was added slowly over 10 minutes. The reaction mixture was stirred for another 60 minutes at room temperature. Ice cold water (200 mL) was added to the reaction mixture, which resulted in the formation of a red precipitate. The precipitate was collected over a coarse frit, washed with 3×50 mL water and 3×50 diethyl ether and dried under reduced pressure to yield Fmoc-Ile-Ala-Leu-Dox SEQ ID NO: 116 (89% yield, 94% HPLC purity by method A). This product was characterized by MS and used for the next step without any further purification.

Example 35

Synthesis of Fmoc-β-Ala-Ile-Ala-Leu-Dox

Doxorubicin.HCl (1.43 g, 2.5 mmol) and yield Fmoc-β-Ala-Ile-Ala-Leu-OH SEQ ID NO: 117 (1.6 g, 2.6 mmol) were dissolved at room temperature in anhydrous DMF (150 mL). To this rapidly stirred solution, DIEA (1 mL, 5.7 mmol) was added in one portion and the reaction mixture was stirred for 15 minutes at room temperature. The reaction mixture was cooled to 0° C. using an ice bath and 1.07 g (2.8 mmol) of HATU was added slowly over 10 minutes. The reaction mixture was stirred for another 60 minutes at room temperature. Ice cold water (200 mL) was added to the reaction mixture, which resulted in the formation of a red precipitate. The precipitate was collected over a coarse frit, washed with 3×50 mL water and 3×50 diethyl ether and dried under reduced pressure to yield Fmoc-β-Ala-Ile-Ala-Leu-Dox SEQ ID NO: 118 (88% yield, 92% HPLC purity by method A). This product was characterized by MS and used for the next step without any further purification.

Example 36

Synthesis of Suc-Ile-Ala-Leu-Dox from Fmoc-Ile-Ala-Leu-Dox

To a solution of Fmoc-Ile-Ala-Leu-Dox SEQ ID NO: 116 (4.4 g, 4.13 mmol) in 20 mL of dry DMF, piperidine (20.4 mL, 206 mmol) was added in one portion resulting in a color change from red to purple. The reaction mixture was stirred for 5 minutes at room temperature and then cooled to −20° C. using dry ice/acetone bath. 21.2 g (210 mmol) of succinic anhydride was then added to the cooled reaction mixture in one portion. The reaction was stirred rapidly at −5° C. for 5 minutes then at room temperature for another 90 minutes. 750 mL of anhydrous diethyl ether was added to the reaction mixture, which resulted in the formation of a red precipitate. This precipitate was isolated on a medium glass frit, washed with 2×50 mL of diethyl ether and dried under reduced pressure to yield Suc-Ile-Ala-Leu-Dox SEQ ID NO: 42 (80% yield, 88% HPLC purity by method B). The final product was purified using prep HPLC method C and characterized by LC/MS which gave a molecular weight of 939 (expected molecular weight 940).

Example 37

Synthesis of Suc-β-Ala-Ile-Ala-Leu-Dox from Fmoc-β-Ala-Ile-Ala-Leu-Dox

To a solution of Fmoc-β-Ala-Ile-Ala-Leu-Dox SEQ ID NO: 118 (4 g, 3.53 mmol) in 40 mL of dry DMF, piperidine (17.4 mL, 176 mmol) was added in one portion resulting in a color change from red to purple. The reaction mixture was stirred for 5 minutes at room temperature and then cooled to −20° C. using dry ice/acetone bath. 18 g (180 mmol) of succinic anhydride was then added to the cooled reaction mixture in one portion. The reaction was stirred rapidly at −5° C. for 5 minutes then at room temperature for another 90 minutes. 750 mL of anhydrous diethyl ether was added to the reaction mixture, which resulted in the formation of a red precipitate. This precipitate was isolated on a medium glass frit, washed with 2×50 mL of diethyl ether and dried under reduced pressure to yield Suc-βAla-Ile-Ala-Leu-Dox SEQ ID NO: 39 (78% yield, 86% HPLC purity by method B). The final product was purified using prep HPLC method C and characterized by LC/MS which gave a molecular weight of 1011 (expected molecular weight 1012).

Example 38

Synthesis of Fmoc-βAla-Ile-Ala-Leu-OBn

The Fmoc-β-Ala-Ile-Ala-Leu SEQ ID NO: 117 (24.34 g, 0.04 mol) is added into a round bottom flask with DMF (350 mL) and a magnetic stirrer. After the tetrapeptide is dissolved, benzyl bromide (4.76 mL, 0.04 mol), followed by cesium carbonate (13.04 g, 0.04 mol), is added to the solution with stirring. The reaction mixture is stirred at room temperature for 1.5 hrs. Then the reaction mixture is slowly poured into a flask with 450 mL of iced water. A large amount of white solid precipitates out which is collected by suction filtration. The product is washed with water (2×200 mL) and placed in a vacuum desiccator.

Example 39

Synthesis of β-Ala-Ile-Ala-Leu-OBn

In a round bottom flask (25 mL), Fmoc-β-Ala-Ile-Ala-Leu-OBn SEQ ID NO: 119 (0.7 g, 1.0 mmol) is dissolved in 5 mL of anhydrous DMF. Piperidine (1.2 mL, 12.1 mmol) is added to the solution and the mixture is stirred at room temperature for 25 minutes. The reaction is quenched with water (6 mL) and extracted with ethyl acetate (2×10 mL). The combined organic layer is further washed by water (2×5 mL), brine (5 mL) and dried over sodium sulfate. A white solid (0.8 g) is obtained after removal of solvent.

Example 40

Synthesis of MeOSuc-βAla-Ile-Ala-Leu-OBn

In a round bottom flask (250 mL), methyl hemisuccinate (3.19 g, 24.2 mmol) is dissolved in anhydrous DMF (50 mL). DIEA (4.22 mL, 24.2 mmol) followed by HBTU (9.17 g, 24.2 mmol) are added into the solution. The mixture is stirred at room temperature for 45 minutes. To this mixture is added a solution of βAla-Ile-Ala-Leu-OBn SEQ ID NO: 119 (crude, containing 10.14 g, 21.3 mmol) in anhydrous DMF (150 mL). The mixture is continually stirred at room temperature for 2.5 hrs. Then, the reaction mixture is slowly poured into a flask with 200 mL of iced water while stirring. A large amount of white solid precipitates out which is extracted by ethyl acetate (3×200 mL). The combined organic layer is further washed by water (2×200 mL), brine (200 mL) and dried over sodium sulfate.

Example 41

Synthesis of MeOSuc-βAla-Ile-Ala-Leu

MeOSuc-βAla-Ile-Ala-Leu-OBn SEQ ID NO: 120 (1.0 g; 1.46 mmol) is added into an Erlenmeyer flask with 100 mL of methanol. 50 mL of methanol is added. The solution is transferred into a hydrogenation reaction vessel. To this vessel, Pd—C (90 mg, 10% wet, 50% water; 0.042 mmol) is added. After hydrogenation for 2 hours at room temperature, the reaction is stopped and the catalyst is filtered.

Example 42

Coupling of MeOSuc-βAla-Ile-Ala-Leu and Doxorubicin Using the "Urea Method"

Under dry nitrogen atmosphere, 26.04 g (52.0 mmol) MeOSuc-βAla-Ile-Ala-Leu SEQ ID NO: 121 and 23.26 g (40.2 mmol) doxorubicin hydrochloride are suspended/dissolved in 800 mL dry, urea-saturated (~30% w/v) DMF and 19.948 mL DIEA. This mixture is cooled to 0–3° C. over ~25 minutes. At this point 21.2 g (56.0 mmol) HATU is added as a solution in ~100 mL urea saturated DMF over 10 minutes (the volume of this solution should be kept minimal). The reaction mixture is stirred for 10 minutes at −2 to 2° C. and poured into 4000 mL ice cold brine, containing 2% v/v acetic acid over approximately five minutes with vigorous stirring. The product is filtered off on a medium porosity fritted glass filter, washed generously with water and dried under reduced pressure.

Example 43

Synthesis of MeOSuc-βAla-Ile-Ala-Leu-Dox Therapeutic Agent

In a round bottom flask (50 mL), MeOSuc-βAla-Ile-Ala-Leu SEQ ID NO: 121 (0.25 g, 0.5 mmol) and doxorubicin (0.29 g, 0.5 mmol) are dissolved in anhydrous DMF (20 mL). After the mixture is stirred for 5 minutes, DIEA (0.17 mL, 1.0 mmol) followed by HBTU (0.19 g, 0.5 mmol) is added into the solution. The mixture is stirred at room temperature for 4 hrs. DMF is removed by a rotary evaporator and the residue is taken up in 4.0 mL 1:1 methylenechloride:methanol. To this solution, 40 mL of ether is slowly added while stirring. A precipitate is formed and collected by suction filtration. The solid is washed with ether (2×10 mL) and dried in a vacuum desiccator.

Example 44

Removal of Free Doxorubicin from MeOSuc-β-Ala-Ile-Ala-Leu-Dox

MeOSuc-β-Ala-Ile-Ala-Leu-Dox SEQ ID NO: 122 (200 mg, 0.194 mmol), DIEA (0.068 mL, 0.388 mmol) and anhydrous DMF (10 mL) are placed in a 50 ml flask equipped with a magnetic stir bar. When MeOSuc-β-Ala-Ile-Ala-Leu-Dox SEQ ID NO: 122 had completely dissolved, isocyanate resin (390 mg, 0.582, pre-swollen in 5 mL of dichloromethane for 5 minutes) is added and the resulting solution is stirred for 2 h at room temperature with periodic HPLC monitoring. The reaction mixture is then filtered through a frit to remove the resin when HPLC traces indicate that the Dox is completely removed. The resin is washed with 10 ml DMF and the DMF washes are combined with the filtered reaction mixture. The filtered reaction mixture washes are then concentrated on a rotary evaporator equipped with a high vacuum pump and a 30° C. water bath. The residue is suspended in 5 ml of DMF and the solution is then slowly added into a rapidly stirred anhydrous diethylether solution. The product is then filtered over a frit and washed with diethylether and dried under reduced pressure to give MeOSuc-β-Ala-Ile-Ala-Leu-Dox SEQ ID NO: 122.

Example 45

Hydrolysis of the MeOSuc-βAla-Ile-Ala-Leu-Dox Therapeutic Agent via Use of Cross Linked Enzyme MeOSuc-βAla-Ile-Ala-Leu-Dox SEQ ID NO: 122 therapeutic agent (1.0 g, 0.975 mmol) and 100 mL DMF are placed in a 500 mL flask. The suspension is vigorously agitated with a magnetic stirrer. When the MeOSuc-βAla-Ile-Ala-Leu-Dox SEQ ID NO: 122 therapeutic agent has completely dissolved, 400 mL deionized water is added and the resulting solution stirred at 35° C. A slurry of 1 g washed CLEC-PC (Altus Biologics) the immobilized enzyme is rinsed in three aliquots of deionized water then resuspended in 10 mL 20% aqueous DMF prior to use. The resulting suspension is stirred at 35° C. with periodic HPLC monitoring. When all of the MeOSuc-βAla-Ile-Ala-Leu-Dox SEQ ID NO: 122 therapeutic agent has been consumed, the reaction mixture is filtered through a 0.45 µM nylon membrane filter to remove the CLEC-PC enzyme. The CLEC-PC cake is washed with 3×10 mL methanol and the methanol washes are combined with the filtered reaction mixture. The filtered reaction mixture plus methanol washes are then concentrated to a red gum on a rotary evaporator equipped with a high vacuum pump and a 30° C. water bath. The red gum is then suspended in 50 mL deionized water at room temperature and rapidly stirred via mechanical stirrer. To this suspension a solution of 77.8 mg sodium bicarbonate (0.926 mmol, 0.95 eq.) in 100 mL deionized water is added over 2 minutes. The suspension is stirred at room temperature 20 minutes. The reaction mixture is filtered through a 0.45 µM nylon membrane filter and lyophilized.

Example 46

Hydrolysis of the MeOSuc-βAla-Ile-Ala-Leu-Dox Therapeutic Agent via Use of Soluble Enzyme 11.0 g (10.72 mmol) MeOSuc-βAla-Ile-Ala-Leu-Dox SEQ ID NO: 122 therapeutic agent is suspended in 800 mL HPLC-grade water and homogenized for 60 minutes with an Ultraturrax T8 homogenizer to yield a finely divided suspension. This suspension is stirred (500 rpm) at 35° C. and adjusted to pH=6.05 with aq. 76 mM NaHCO$_3$. 1.0 g *C. Antarctica* "B" lipase (Altus Biologics) is then added and the reaction mixture stirred at 35° C. for 48 hours. During the 48 hr reaction time, pH is maintained between 5.3 and 6.2 by periodic addition of 76 mM NaHCO$_3$ and the reaction is periodically monitored by HPLC. After the reaction is nearly complete, the reaction mixture is then adjusted to pH=7 with aq. 76 mM NaHCO$_3$ and filtered through a pad of Celite 521. The clarified reaction mixture is then acidified to ca. pH 3 with 5 mL glacial acetic acid. The precipitate is isolated by Celite 521 filtration, subsequently rinsing the Celite pad with methanol. The methanol solution is filtered through a 10–20 µM fritted glass filter and is dried by rotary evaporation. This product is converted to the sodium salt by dissolution in 70 mL 76 mM NaHCO$_3$ (0.95 eq.) and lyophilized. The product is identical to that of Example 45.

Example 47

Immobilized *Candida Antarctica* "B" Lipase Hydrolysis of MeOSuc-βAla-Ile-Ala-Leu-Dox Therapeutic Agent 30.0 g *Candida Antarctica* "B" lipase (Altus Biologics) is dissolved in 300 mL water and dialyzed against 3×4 l of 50 mM aq. NaHCO$_3$ (pH=6.4). 360 mL of Pharmacia NHS-Activated Sepharose 4 Fast Flow is placed in a coarse glass fritted funnel and rinsed with 5×450 mL ice-cold 1 mM aq. HCl. The rinsed NHS-Activated Sepharose is then combined with the dialyzed enzyme solution. The resulting suspension is stirred at ambient temperature (ca. 22° C.) for 2.0 hours. The Sepharose/enzyme conjugate is then isolated on a coarse fritted glass filter and then stirred in 1000 mL 100 mM aq. TRIS (pH=7.45) for 15 minutes. This suspension is filtered and incubated with another 1000 mL 100 mM aqueous TRIS buffer (pH=7.45) at 4° C., overnight. In the morning, the immobilized enzyme is filtered off and after washing with water, is placed into a 2000 mL three necked, round bottomed flask. 43 g MeOSuc-βAla-Ile-Ala-Leu-Dox SEQ ID NO: 122 therapeutic agent is added and the solids are suspended in 800 mL deionized water. The flask is fitted with an overhead stirrer, and a pH-stat set to keep the pH of the reaction mixture between 5.9–6.2 by controlling a syringe pump. The syringe pump is charged 0.1 M NaHCO$_3$. Progress of the reaction is followed by HPLC. After the reaction is nearly complete, the immobilized enzyme is filtered off and the liquid phase is lyophilized. The dry solids are then suspended in about 11 mL dry THF and filtered off.

Example 48

Large Scale Synthesis of Methyl Succinyl-N-Cap Form of βAla-Leu-Ala-Leu-Dox Therapeutic Agent 69.6 g Doxorubicin.HCl (120 mmol) and 100 g MeOSuc-βAla-Leu-Ala-Leu SEQ ID NO: 123 (199 mmol) were dissolved in anhydrous DMF (10 L) under nitrogen. 76 mL DIEA (434 mmol) was added to the reaction mixture and the reaction mixture was stirred for 10 minutes at room temperature under nitrogen. The reaction mixture was then cooled to 0° C. over 10 minutes. In a separate flask a solution of 864 g HATU (220 mmol) in DMF (500 mL) was prepared. The HATU solution was added slowly over 20 minutes to the reaction mixture while the reaction mixture was maintained at 0° C. The reaction mixture was stirred at 0° C. for 30 minutes.

A solution of NaCl (7.5 Kg, at least 30% w/v) in water (25 L) was prepared and cooled to 0° C. The reaction mixture was then slowly added to the cooled brine solution with vigorous stirring over 120 minutes. The color of the solution remained red, a blue solution would have indicated that the pH needed adjustment immediately to between 5.8–6.0 by adding acetic acid. The temperature was maintained at approximately 5° C. The red precipitate was filtered off on a medium porosity fritted glass filter, washed with water and dried under vacuum pressure over P$_2$O$_5$ to yield 115 g of MeOSuc-βAla-Leu-Ala-Leu-Dox SEQ ID NO: 124.

Example 49

Treatment of MeOSuc-βAla-Leu-Ala-Leu-Dox with Ps-Isocyanate Beads to Remove Traces of Doxorubicin 146.4 g PS-isocyanate beads (240 mmol; supplied by Argonaut Lab, San Carlos, Calif.) were dissolved in 1.5 L of anhydrous DMF and allowed to swell for 5–10 minutes at room temperature. The swelled beads were filtered through a glass-fritted funnel and washed with additional 500 mL of anhydrous DMF. 115 g MeOSuc-βAla-Leu-Ala-Leu-Dox SEQ ID NO: 124 (112 mmol) was dissolved in 1000 mL of anhydrous DMF and 2.1 mL DIEA (12 mmol) was added followed by the swelled PS-isocyanate beads. The reaction mixture was stirred at room temperature and was monitored using HPLC until the amount of doxorubicin peak was less than 0.1%. It takes anywhere from 2–12 h depending upon the size of the batch. Analytical HPLC analyses were performed using Water 2690 Column: Waters Symmetry Shield C$_8$ 3.5 µM 4.6×150 mm (cat # WAT094269), solvent: A-80% aqueous 20 mM ammonium formate (pH=4.5) 20% acetonitrile, solvent: B-20% aqueous 20 mM ammonium formate (pH=4.5) 80% acetonitrile. Column temperature: controlled room temperature, sample temperature: 4° C., Run time: 37.5 minutes, detector: 254 nm, Flow rate: 1.0 mL/min, Injection amount 10 μg (0.5 mg/mL×0.02 mL), Mobile Phase A and B. Gradient: 37.5 minute linear gradient from 100% mobile phase A to 100% mobile phase B with a 7.5 minute equilibration delay.

At six hours the amount of doxorubicin peak was less than 0.1%, the reaction mixture was filtered through a coarse sintered glass funnel to remove the beads. A brine solution (at least 30% w/v) of 1.1 kg NaCl in 3.5 L water was prepared and cooled to 0° C. The filtered reaction mixture was then slowly added to the cooled brine solution with vigorous stirring over 45 minutes. The color of the solution remained red, a blue solution would have indicated that the pH needed adjustment immediately to between 5.8–6.0 by adding acetic acid. The red precipitate was filtered through a medium sintered glass funnel, washed with water and dried under vacuum pressure over $P_2O_5$ to yield MeOSuc-βAla-Leu-Ala-Leu-Dox SEQ ID NO: 124 free of any residual doxorubicin.

MeOSuc-βAla-Leu-Ala-Leu-Dox SEQ ID NO: 124 was dissolved in 1 L MeOH and the methanol solution was then slowly added to 14 L of cooled ethyl ether with vigorous stirring over 60 minutes. The red precipitate was filtered through a medium sintered glass funnel, washed with ether (1 L) and dried under vacuum pressure to yield 110 g MeOSuc-βAla-Leu-Ala-Leu-Dox SEQ ID NO: 124. The purity was determined to be 96.5% by HPLC, as described in Example 37. MS m/z calcd. for $C_{50}H_{67}N_5O_{18}$ 1025, found 1048 (M++Na).

Example 50

Enzymatic Hydrolysis of MeOSuc-βAla-Leu-Ala-Leu-Dox to Yield Suc-βAla-Leu-Ala-Leu-Dox The CLEC-CAB (*Candida Antartica* "B" Lipase) enzyme was purchased (from Altus Biologics., Boston, Mass.) in solution form, where the concentration of the enzyme is defined by the weight of dry enzyme per milliliter of solution. The crude enzyme suspension was shaken for a few minutes to obtain a homogenous solution. 504 mL (328 mmol) of this homogenous solution was aliquoted into a flask. 2.5 L of deionized water was added and the slurry was stirred for 10 minutes using a magnetic stirrer. The enzyme solution was filtered using a coarse glass fritted funnel, without taking the enzyme to dryness. The enzyme was transferred back into a flask. The enzyme is suspended in water and filtered three more times.

The enzyme cake was resuspended into 550 mL of deionized water and transferred into a RB flask. To this suspension, 109 g MeOSuc-βAla-Leu-Ala-Leu-Dox SEQ ID NO: 124 (106 mmol) was added and the reaction mixture was stirred at room temperature (25° C.). The pH of the reaction mixture was maintained between 5.8 and 6.1 by a pH-stat equipped with a syringe pump charged with 1 N $NaHCO_3$ solution. Progress of the reaction was followed with periodic HPLC monitoring, as described in Example 49. After 24 hours, the reaction seems to be 94% complete, as determined by HPLC.

To speed up the reaction, additional CLEC enzyme was required after 24 hours. 168 mL of the CLEC enzyme (homogenous solution) was washed in a column format as described above. The enzyme cake was resuspended into 1.1 L of deionized water and added to the reaction mixture. The reaction mixture was stirred at room temperature with periodic HPLC monitoring and the pH was maintained between 5.8 and 6.1. After 60 hours, the reaction was 99.9% complete, as monitored by HPLC.

The CLEC enzyme was removed from the reaction mixture by filtration through a 0.2 μM filter and rinsed with 500 mL of deionized water. The filtrate was then lyophilized to yield 95.2 g Suc-βAla-Leu-Ala-Leu-Dox.Na SEQ ID NO: 41, 87% physical yield, MS m/z calcd. for $C_{49}H_{65}N_5O_{18}$ 1011, found 1034 (M+ +Na).

The prodrug compound, Suc-βAla-Leu-Ala-Leu-Dox SEQ ID NO: 41, was fully characterized by mass spectrum analysis, FTIR, NMR.

Mass spectrum analysis of Suc-βAla-Leu-Ala-Leu-Dox SEQ ID NO: 41 clearly shows the presence of the molecular ion peak (m/z) at 1034 (M+ +Na) which matches with the calculated m/z for Suc-βAla-Leu-Ala-Leu-Dox SEQ ID NO: 41 ($C_{49}H_{65}N_5O_{18}Na$) at 1033.

The sample of Suc-βAla-Leu-Ala-Leu-Dox SEQ ID NO: 41 was also analyzed by FTIR. The spectrum matched that of a reference standard of the above material. Assignments for major absorptions are as follow:

| Hydroxyl | 3379 cm$^{-1}$ |
|---|---|
| C—H | 3000–2700 |
| Carbonyls | 1650–1725 |

Figure 28:
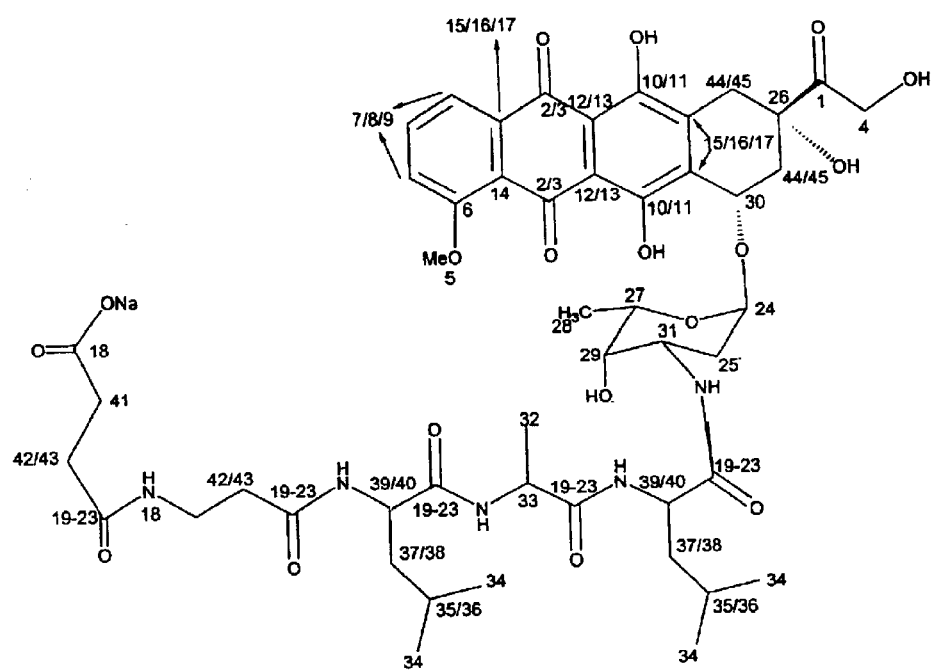
FIG. 28 illustrates the NMR assignment for MeOSuc-βAla-Leu-Ala-Leu-Dox (SEQ ID NO: 47), a typical compound of the invention.

Finally the sample was analyzed by NMR. The chemical shifts and assignments are listed in Table 31 and illustrated in FIG. 28. There are three carbons in the ketone region, at 215.2, 187.7, 187.4 ppm, consistent with the structure of Suc-βAla-Leu-Ala-Leu-Dox SEQ ID NO: 41. The latter two have similar chemical shifts, so are assigned to (2) and (3), at 187.7 and 187.4 ppm. The remaining ketone is therefore (1). Further evidence from these assignments arise from the HMQC and HMBC spectra; none of these three show any HMQC peaks, so are nonprotonated, and only (1) has a long-range C—H coupling (HMBC), to the proton at 4.77 ppm, which is a two-proton singlet, which is therefore (4). From the HMQC spectrum, the carbon at 65.7 ppm is linked to these protons.

The $^1H$ NMR signal at 3.96 ppm has the chemical shift and the area of a methoxy group; these protons are coupled to the carbon at 57.2 ppm, and are assigned to the only methoxy in the structure (5). The $^{13}C$ chemical shift is also consistent with a methoxy. The long-range C—H coupling of the protons is to the carbon at 162.3 ppm, which must be (6).

The HMQC spectrum shows that there are three protonated aromatic carbons at 120.5, 120.3 and 137.2 ppm; the aromatic protons did not show any long-range C—H coupling, nor any coupling between adjacent protons. The aromatic protons signals are very broad, indicating a short $T_2$ relaxation time, which explains the lack of any observed coupling. Given this lack of coupling, it is not possible to assign these three sites uniquely, and are collectively assigned to (7), (8) and (9).

The two non-protonated aromatic carbons at 157.2 and 156.1 ppm have chemical shifts consistent with (10) and (11), i.e., aromatic carbons attached to oxygen. No long-range coupling is observed.

The 13C NMR signals at 112.3 and 112.0 ppm are consistent with aromatic carbons ortho to oxygen substitution, and are assigned to (12) and (13). The 13C NMR signal at 121.3 also shows this effect, so is assigned to (14). The remaining three non-protonated aromatic carbons are assigned to the last three carbons in the region, (15), (16) and (17).

The lack of any long-range C—H coupling to any of the aromatic carbons is unexpected, and indicates that the coupling is very small or non-existent, either due to short $T_2$ relaxation times or a planar configuration.

There are six carbonyl carbons at 181 to 174 ppm; of these, the one at 180.6 ppm is the only one with a chemical shift consistent with a sodium salt, so is assigned to (18). This peak shows long-range C—H coupling to the protons at 2.4 ppm, which are unresolved. The remaining five carbonyl carbons are all within a one ppm chemical shift range, and are not possible (19), (20), (21), (22), (23).

The carbon at 102.3 ppm has a chemical shift consistent with a carbon bound to two separate oxygen, so must be (24). This has long-range C—H coupling to the proton at 1.74 ppm, which is assigned to (25). This proton is coupled to the carbon at 30.6 ppm. Of the carbons in the C—O region (80 to 60 ppm), only one is protonated, at 77.4 ppm, so must be (26). This has no long-range C—H coupling, to either the proton or the carbon.

There are three carbons not yet assigned in the 80 to 60 ppm region, all methines attached to oxygen. They all have similar chemical shifts (71.2, 69.9 and 68.8 ppm), but it seems clear that the carbon at 68.8 ppm shows long-range coupling to the methyl to (28). The carbon at 69.9 also shows long-range coupling to the methyl at (28), so must be adjacent to (27), and is assigned to (29). The remaining methine is therefore (30).

The proton at 3.6 ppm (29) shows long-range C—H coupling to only one carbon, at 47.3 ppm. The only adjacent unassigned carbon must be (31). The protons of (31) overlap other protons and long-range correlations are not possible.

The remaining four methyls are in the isopropyl region, and one is at 1.25/1.34 ppm, and must correspond to the last remaining methyl, (32). The protons of this methyl show long-range coupling to only one carbon, at 51.3 ppm, which must be (33). The protons of (33) overlap severely with other protons and can not be used for any long-range correlations.

The remaining four methyls must all arise from the isopropyl methyls, collectively labeled (34). The protons of (34) show long-range coupling between the paired methyls, and to the carbons at 25.9/25.8 and 41.6/41.7 ppm; the methines are assigned (35)/(36) and the methylenes (37)/(38). All of these protons overlap at 1.5 to 1.8 ppm, but show long-range coupling to the methines at 54.7/53.5 ppm, which must be the ones adjacent to the amides, and are assigned (39)/(40).

The remaining five carbons, all methylenes, show long-range coupling to carbonyls, so must be adjacent to such, and are assigned (41), (42) and (43); the $^1$H NMR chemical shifts all overlap at 2.4 ppm, and correspondence to carbons at 37.2, 34.4 and 33.8 ppm. Since the carbon at 37.2 is the most difference, it is assigned to the sodium salt carbonyl (41), and the other two to the amide carbonyls (42), (43). The remaining two methylenes are too similar for specific assignment (44), (45).

There is one site unassigned. There are thirty protons in the 5.5 to 1.5 ppm region, consistent with the structure, including this assigned site. Therefore it is likely that the carbon signal is hidden under the solvent signal at about 50 ppm, which would be consistent for methylene adjacent to a nitrogen.

TABLE 31

| $^{13}$C and $^1$H Chemical Shifts | HMOC to $^1$H | Assignment |
| --- | --- | --- |
| 215.2 | | 1 |
| 187.7 | | 2/3 |
| 187.4 | | 2/3 |
| 180.6 | | 18 |
| 176.1 | | 19–23 |
| 175.8 | | 19–23 |
| 175.4 | | 19–23 |
| 175.2 | | 19–23 |
| 174.1 | | 19–23 |
| 162.3 | | 6 |
| 157.2 | | 10/11 |
| 156.1 | | 10/11 |
| 137.2 | 7.68 | 7/8/9 |
| 136.1 | | 15/16/17 |
| 135.6 | | 15/16/17 |
| 135 | | 15/16/17 |
| 121.3 | | 14 |
| 120.5 | 7.68 | 7/8/9 |
| 120.3 | 7.42 | 7/8/9 |
| 112.3 | | 12/13 |
| 112 | | 12/13 |
| 102.3 | 5.34 | 24 |
| 77.4 | | 26 |
| 71.2 | 4.97 | 30 |
| 69.9 | 3.6 | 29 |
| 68.8 | 4.24 | 27 |
| 65.7 | 4.77 | 4 |
| 57.2 | 3.96 | 5 |
| 54.7 | 4.24 | 39/40 |
| 53.5 | 4.32 | 39/40 |
| 51.3 | 4.24 | 33 |
| 47.3 | 4.15/4.12 | 31 |
| 41.6 | 1.6 | 35/36 |
| 41.5 | 1.6 | 35/36 |
| 37.2 | 2.4 | 41 |
| 37 | 3.45 | 44/45 |
| 34.4 | 2.4 | 42/43 |
| 34 | 3–2.7 | 44/45 |
| 33.8 | 2.4 | 42/43 |
| 30.6 | 1.75 | 25 |
| 25.9 | 1.6 | 37/38 |
| 25.8 | 1.6 | 37/38 |
| 23.5 | 0.9 | 34 |
| 23.3 | 0.9 | 34 |
| 22.1 | 0.9 | 34 |
| 21.7 | 0.9 | 34 |
| 17.4 | 1.35/1.34 | 32 |
| 17.5 | 1.29/1.27 | 28 |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of designing a prodrug, the method comprising:

(1) providing an oligopeptide of the formula $(AA)_n$-$AA^{P2}$-$AA^{P1}$-$AA^{P1'}$-$(AA)_m$, wherein:
n and m are integers,
$AA^{P2}$ represents any amino acid,
$AA^{P1}$ represents any ammo acid,
$AA^{P1'}$ represents any amino acid, and
each AA independently represents an amino acid, (2) linking the oligopeptide at a first attachment site of the oligopeptide to a stabilizing group that hinders cleavage of the oligopeptide by enzymes present in whole blood, and (3) directly or indirectly linking the oligopeptide to a therapeutic agent at a second attachment site of the oligopeptide, wherein steps (2) and (3) may be performed in any order or concurrently and further wherein a conjugate is formed by performance of steps (1) through (3), (4) testing if the conjugate is cleavable by CD10, and (5) selecting the conjugate as a prodrug if the conjugate is cleavable by CD10.

2. The method of claim 1 wherein n is 0 to 3, m is 0 to 3, and m+n is no more than 3 of the oligopeptide of the formula $(AA)_n$-$AA^{P2}$-$AA^{P1}$-$AA^{P1'}$-$(AA)_m$.

3. The method of claim 1 wherein the first attachment site is the N-terminus of the oligopeptide.

4. The method of claim 1 wherein the second attachment site is the C-terminus of the oligopeptide.

5. The method of claim 1 wherein the first attachment site is the C-terminus of the oligopeptide.

6. The method of claim 1 wherein the second attachment site is the N-terminus of the oligopeptide.

7. The method of claim 1 wherein the conjugate is further tested for cleavage by thimet oligopeptidase (TOP).

8. The method of claim 1, wherein the conjugate is further tested for cleavage by prostate specific antigen (PSA).

9. The method claim 1, wherein the conjugate is further tested for stability in whole blood.

10. The method of claim 1, wherein the conjugate is tested for cleavage by CD10 by incubating the conjugate with porcine kidney CD10.

* * * * *

SEQUENCE LISTING

<160> NUMBER OF SEQ ID NOS: 126

<210> SEQ ID NO 1
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 1

Xaa Ile Ala Phe
1

<210> SEQ ID NO 2
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 2

Xaa Ile Ala Ile
1

<210> SEQ ID NO 3
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Tetrahydroisoquinoline-3-carboxylic acid

<400> SEQUENCE: 3

Xaa Ile Ala Leu
1

<210> SEQ ID NO 4
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 2-Thienylalanine

<400> SEQUENCE: 4

Xaa Ile Ala Leu
1

<210> SEQ ID NO 5
<211> LENGTH: 4
<212> TYPE: PRT
<213> ORGANISM: Artificial Sequence
<220> FEATURE:
<223> OTHER INFORMATION: chemically synthesized

```
<220> FEATURE:
<221> NAME/KEY: MISC_FEATURE
<222> LOCATION: (1)..(1)
<223> OTHER INFORMATION: 2-Naphthylalanine

<400> SEQUENCE: 5

Xaa Ile Ala Leu
1

<210> SEQ ID NO 6
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 4-(Aminomethyl)benzoic acid

<400> SEQUENCE: 6

Xaa Ile Ala Leu
1

<210> SEQ ID NO 7
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Aminoisobutyric acid

<400> SEQUENCE: 7

Xaa Ile Ala Leu
1

<210> SEQ ID NO 8
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 8

Xaa Ile Ala Leu
1

<210> SEQ ID NO 9
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 2-Thienylalanine
<220> FEATURE:
<221> NAME/KEY: MISC_FEATURE
<222> LOCATION: (3)..(3)
<223> OTHER INFORMATION: Aminoisobutyric acid

<400> SEQUENCE: 9
```

```
Xaa Ile Xaa Leu
1

<210> SEQ ID NO 10
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 2-Naphthylalanine
<220> FEATURE:
<221> NAME/KEY: MISC_FEATURE
<222> LOCATION: (3)..(3)
<223> OTHER INFORMATION: Aminoisobutyric acid

<400> SEQUENCE: 10

Xaa Ile Xaa Leu
1

<210> SEQ ID NO 11
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (3)..(3)
<223> OTHER INFORMATION: Aminoisobutyric acid

<400> SEQUENCE: 11

Xaa Ile Xaa Leu
1

<210> SEQ ID NO 12
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 4-(Aminomethyl)benzoic acid
<220> FEATURE:
<221> NAME/KEY: MISC_FEATURE
<222> LOCATION: (3)..(3)
<223> OTHER INFORMATION: Aminoisobutyric acid

<400> SEQUENCE: 12

Xaa Ile Xaa Leu
1

<210> SEQ ID NO 13
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Aminoisobutyric acid
<220> FEATURE:
<221> NAME/KEY: MISC_FEATURE
```

```
<222> LOCATION: (3)..(3)
<223> OTHER INFORMATION: Aminoisobutyric acid

<400> SEQUENCE: 13

Xaa Ile Xaa Leu
1

<210> SEQ ID NO 14
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 14

Xaa Ile Gly Phe
1

<210> SEQ ID NO 15
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 15

Xaa Ile Gly Ile
1

<210> SEQ ID NO 16
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Tetrahydroisoquinoline-3-carboxylic acid

<400> SEQUENCE: 16

Xaa Ile Gly Leu
1

<210> SEQ ID NO 17
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 2-Thienylalanine

<400> SEQUENCE: 17

Xaa Ile Gly Leu
1

<210> SEQ ID NO 18
<211> LENGTH: 4
```

```
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 2-Naphthylalanine

<400> SEQUENCE: 18

Xaa Ile Gly Leu
1

<210> SEQ ID NO 19
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 19

Xaa Ile Gly Leu
1

<210> SEQ ID NO 20
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 4-(Aminomethyl)benzoic acid

<400> SEQUENCE: 20

Xaa Ile Gly Leu
1

<210> SEQ ID NO 21
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Aminoisobutyric acid

<400> SEQUENCE: 21

Xaa Ile Gly Leu
1

<210> SEQ ID NO 22
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 22
```

```
Xaa Ile Thr Ile
1

<210> SEQ ID NO 23
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 23

Xaa Ile Tyr Ile
1

<210> SEQ ID NO 24
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 24

Xaa Ile Ala Gly
1

<210> SEQ ID NO 25
<211> LENGTH: 3
<212> TYPE: PRT
<213> ORGANISM: Artificial Sequence
<220> FEATURE:
<223> OTHER INFORMATION: chemically synthesized

<400> SEQUENCE: 25

Ile Ala Leu
1

<210> SEQ ID NO 26
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: N-methyl-Alanine

<400> SEQUENCE: 26

Ile Xaa Leu
1

<210> SEQ ID NO 27
<211> LENGTH: 3
<212> TYPE: PRT
<213> ORGANISM: Artificial sequence
<220> FEATURE:
<223> OTHER INFORMATION: chemically synthesized

<400> SEQUENCE: 27

Ile Ala Phe
1
```

```
<210> SEQ ID NO 28
<211> LENGTH: 3
<212> TYPE: PRT
<213> ORGANISM: Artificial sequence
<220> FEATURE:
<223> OTHER INFORMATION: chemically synthesized

<400> SEQUENCE: 28

Ile Ala Ile
1

<210> SEQ ID NO 29
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: Aminoisobutyric acid

<400> SEQUENCE: 29

Ile Xaa Leu
1

<210> SEQ ID NO 30
<211> LENGTH: 3
<212> TYPE: PRT
<213> ORGANISM: Artificial sequence
<220> FEATURE:
<223> OTHER INFORMATION: chemically synthesized

<400> SEQUENCE: 30

Ile Gly Phe
1

<210> SEQ ID NO 31
<211> LENGTH: 3
<212> TYPE: PRT
<213> ORGANISM: Artificial sequence
<220> FEATURE:
<223> OTHER INFORMATION: chemically synthesized

<400> SEQUENCE: 31

Ile Gly Ile
1

<210> SEQ ID NO 32
<211> LENGTH: 3
<212> TYPE: PRT
<213> ORGANISM: Artificial sequence
<220> FEATURE:
<223> OTHER INFORMATION: chemically synthesized

<400> SEQUENCE: 32

Ile Gly Leu
1

<210> SEQ ID NO 33
<211> LENGTH: 3
<212> TYPE: PRT
<213> ORGANISM: Artificial sequence
<220> FEATURE:
<223> OTHER INFORMATION: chemically synthesized

<400> SEQUENCE: 33
```

```
Ile Thr Ile
1

<210> SEQ ID NO 34
<211> LENGTH: 3
<212> TYPE: PRT
<213> ORGANISM: Artificial Sequence
<220> FEATURE:
<223> OTHER INFORMATION: chemically synthesized

<400> SEQUENCE: 34

Ile Ala Gly
1

<210> SEQ ID NO 35
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 35

Xaa Ile Tyr Leu
1

<210> SEQ ID NO 36
<211> LENGTH: 4
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 36

Xaa Ile Tyr Gly
1

<210> SEQ ID NO 37
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 9-Fluorenylmethyloxycarbonyl-Beta-Alanine

<400> SEQUENCE: 37

Xaa Ile Ala Leu
1

<210> SEQ ID NO 38
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Methyl-succinyl-Beta-Alanine
```

```
<400> SEQUENCE: 38

Xaa Ile Ala Leu
1

<210> SEQ ID NO 39
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 39

Xaa Ile Ala Xaa
1

<210> SEQ ID NO 40
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (4)..(4)
<223> OTHER INFORMATION: Leucine-Doxorubicin

<400> SEQUENCE: 40

Xaa Ile Ala Xaa
1

<210> SEQ ID NO 41
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 41

Xaa Leu Ala Xaa
1

<210> SEQ ID NO 42
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
```

```
<223> OTHER INFORMATION: Succinyl-Isoleucine
<220> FEATURE:
<221> NAME/KEY: MISC_FEATURE
<222> LOCATION: (3)..(3)
<223> OTHER INFORMATION: Leucine-doxorubicin

<400> SEQUENCE: 42

Xaa Ala Xaa
1

<210> SEQ ID NO 43
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Leucine
<220> FEATURE:
<221> NAME/KEY: MISC_FEATURE
<222> LOCATION: (3)..(3)
<223> OTHER INFORMATION: Leucine-doxorubicin

<400> SEQUENCE: 43

Xaa Tyr Xaa
1

<210> SEQ ID NO 44
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 44

Xaa Leu Tyr Xaa
1

<210> SEQ ID NO 45
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Leucine
<220> FEATURE:
<221> NAME/KEY: MISC_FEATURE
<222> LOCATION: (3)..(3)
<223> OTHER INFORMATION: Leucine-doxorubicin

<400> SEQUENCE: 45

Xaa Ala Xaa
1

<210> SEQ ID NO 46
<211> LENGTH: 3
<212> TYPE: PRT
<213> ORGANISM: Artificial sequence
```

```
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Leucine
<220> FEATURE:
<221> NAME/KEY: MISC_FEATURE
<222> LOCATION: (3)..(3)
<223> OTHER INFORMATION: Glycine-doxorubicin

<400> SEQUENCE: 46

Xaa Ala Xaa
1

<210> SEQ ID NO 47
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Methyl-hemisuccinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 47

Xaa Leu Ala Xaa
1

<210> SEQ ID NO 48
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 48

Xaa Leu Ala Leu
1

<210> SEQ ID NO 49
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine

<400> SEQUENCE: 49

Xaa Leu Ala Leu
1

<210> SEQ ID NO 50
<211> LENGTH: 4
<212> TYPE: PRT
<213> ORGANISM: Artificial sequence
<220> FEATURE:
<223> OTHER INFORMATION: chemically synthesized
<220> FEATURE:
```

```
<221> NAME/KEY: MISC_FEATURE
<222> LOCATION: (1)..(1)
<223> OTHER INFORMATION: Succinyl-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 50

Xaa Leu Ala Xaa
1

<210> SEQ ID NO 51
<211> LENGTH: 5
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: p-Glutamate
<220> FEATURE:
<221> NAME/KEY: MISC_FEATURE
<222> LOCATION: (5)..(5)
<223> OTHER INFORMATION: Leucine-doxorubicin

<400> SEQUENCE: 51

Xaa Ala Leu Ala Xaa
1               5

<210> SEQ ID NO 52
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: D-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 52

Xaa Leu Ala Xaa
1

<210> SEQ ID NO 53
<211> LENGTH: 5
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: D-Leucine
<220> FEATURE:
<221> NAME/KEY: MISC_FEATURE
<222> LOCATION: (5)..(5)
<223> OTHER INFORMATION: Leucine-daunorubicin

<400> SEQUENCE: 53

Xaa Ala Leu Ala Xaa
1               5

<210> SEQ ID NO 54
<211> LENGTH: 5
```

```
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: D-Leucine
<220> FEATURE:
<221> NAME/KEY: MISC_FEATURE
<222> LOCATION: (2)..(2)
<223> OTHER INFORMATION: D-Alanine
<220> FEATURE:
<221> NAME/KEY: MISC_FEATURE
<222> LOCATION: (5)..(5)
<223> OTHER INFORMATION: Leucine-daunorubicin

<400> SEQUENCE: 54

Xaa Xaa Leu Ala Xaa
1               5

<210> SEQ ID NO 55
<211> LENGTH: 6
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Acetyl-Histidine
<220> FEATURE:
<221> NAME/KEY: MISC_FEATURE
<222> LOCATION: (6)..(6)
<223> OTHER INFORMATION: Glutamine-doxorubicin

<400> SEQUENCE: 55

Xaa Ser Ser Lys Leu Xaa
1               5

<210> SEQ ID NO 56
<211> LENGTH: 7
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Morpholinocarbonyl-Histidine
<220> FEATURE:
<221> NAME/KEY: MISC_FEATURE
<222> LOCATION: (7)..(7)
<223> OTHER INFORMATION: Leucine-doxorubicin

<400> SEQUENCE: 56

Xaa Ser Ser Lys Leu Gln Xaa
1               5

<210> SEQ ID NO 57
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: N-(2-hydroxypropyl)methacrylamide-Glycine
<220> FEATURE:
<221> NAME/KEY: MISC_FEATURE
<222> LOCATION: (4)..(4)
<223> OTHER INFORMATION: Glycine-doxorubicin
```

```
<400> SEQUENCE: 57

Xaa Phe Leu Xaa
1

<210> SEQ ID NO 58
<211> LENGTH: 6
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: N-glutaryl-(4-hydroxyprolyl)-Alanine
<220> FEATURE:
<221> NAME/KEY: MISC_FEATURE
<222> LOCATION: (3)..(3)
<223> OTHER INFORMATION: Cyclohexylglycine
<220> FEATURE:
<221> NAME/KEY: MISC_FEATURE
<222> LOCATION: (6)..(6)
<223> OTHER INFORMATION: Leucine-doxorubicin

<400> SEQUENCE: 58

Xaa Ser Xaa Gln Ser Xaa
1               5

<210> SEQ ID NO 59
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: N-Cbz-Glycine
<220> FEATURE:
<221> NAME/KEY: MISC_FEATURE
<222> LOCATION: (4)..(4)
<223> OTHER INFORMATION: Leucine-doxorubicin

<400> SEQUENCE: 59

Xaa Phe Ala Xaa
1

<210> SEQ ID NO 60
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: N-Cbz-Glycine
<220> FEATURE:
<221> NAME/KEY: MISC_FEATURE
<222> LOCATION: (4)..(4)
<223> OTHER INFORMATION: Leucine-PABC-doxorubicin

<400> SEQUENCE: 60

Xaa Phe Ala Xaa
1

<210> SEQ ID NO 61
<211> LENGTH: 4
<212> TYPE: PRT
<213> ORGANISM: Artificial sequence
<220> FEATURE:
```

```
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 61

Xaa Leu Ala Xaa
1

<210> SEQ ID NO 62
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 62

Xaa Ile Ala Xaa
1

<210> SEQ ID NO 63
<211> LENGTH: 6
<212> TYPE: PRT
<213> ORGANISM: Artificial sequence
<220> FEATURE:
<223> OTHER INFORMATION: chemically synthesized

<400> SEQUENCE: 63

Phe Phe Gly Phe Leu Ala
1               5

<210> SEQ ID NO 64
<211> LENGTH: 5
<212> TYPE: PRT
<213> ORGANISM: Artificial sequence
<220> FEATURE:
<223> OTHER INFORMATION: chemically synthesized

<400> SEQUENCE: 64

Tyr Gly Gly Phe Leu
1               5

<210> SEQ ID NO 65
<211> LENGTH: 11
<212> TYPE: PRT
<213> ORGANISM: Artificial sequence
<220> FEATURE:
<223> OTHER INFORMATION: chemically synthesized

<400> SEQUENCE: 65

Arg Pro Lys Pro Gln Gln Phe Phe Gly Leu Met
1               5                   10

<210> SEQ ID NO 66
<211> LENGTH: 13
<212> TYPE: PRT
```

<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Pyroglutamic acid

<400> SEQUENCE: 66

Xaa Leu Tyr Glu Asn Lys Pro Arg Arg Pro Tyr Ile Leu
1               5                   10

<210> SEQ ID NO 67
<211> LENGTH: 8
<212> TYPE: PRT
<213> ORGANISM: Artificial sequence
<220> FEATURE:
<223> OTHER INFORMATION: chemically synthesized

<400> SEQUENCE: 67

Asp Tyr Met Gly Trp Met Asp Phe
1               5

<210> SEQ ID NO 68
<211> LENGTH: 4
<212> TYPE: PRT
<213> ORGANISM: Artificial sequence
<220> FEATURE:
<223> OTHER INFORMATION: chemically synthesized fluorogenic substrate
<220> FEATURE:
<221> NAME/KEY: MISC_FEATURE
<222> LOCATION: (1)..(1)
<223> OTHER INFORMATION: Dansyl-D-Alanine
<220> FEATURE:
<221> NAME/KEY: MISC_FEATURE
<222> LOCATION: (3)..(3)
<223> OTHER INFORMATION: pN02-Phenylalanine

<400> SEQUENCE: 68

Xaa Gly Xaa Gly
1

<210> SEQ ID NO 69
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (4)..(4)
<223> OTHER INFORMATION: Leucine-benzyl ester

<400> SEQUENCE: 69

Xaa Ile Ala Xaa
1

<210> SEQ ID NO 70
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine

```
<400> SEQUENCE: 70

Xaa Ile Ala Leu
 1

<210> SEQ ID NO 71
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Allyl-succinyl-Beta-Alanine

<400> SEQUENCE: 71

Xaa Ile Ala Leu
 1

<210> SEQ ID NO 72
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Allyl-succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 72

Xaa Ile Ala Xaa
 1

<210> SEQ ID NO 73
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Methionine
<220> FEATURE:
<221> NAME/KEY: MISC_FEATURE
<222> LOCATION: (3)..(3)
<223> OTHER INFORMATION: Leucine-doxorubicin

<400> SEQUENCE: 73

Xaa Ala Xaa
 1

<210> SEQ ID NO 74
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Phenylalanine
<220> FEATURE:
<221> NAME/KEY: MISC_FEATURE
<222> LOCATION: (3)..(3)
```

```
<223> OTHER INFORMATION: Leucine-doxorubicin

<400> SEQUENCE: 74

Xaa Ala Xaa
1

<210> SEQ ID NO 75
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-pNA

<400> SEQUENCE: 75

Xaa Leu Ala Xaa
1

<210> SEQ ID NO 76
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 76

Xaa Leu Ala Xaa
1

<210> SEQ ID NO 77
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Phenylalanine-daunorubicin

<400> SEQUENCE: 77

Xaa Ile Ala Xaa
1

<210> SEQ ID NO 78
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
```

```
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 78

Xaa Ile Ala Xaa
1

<210> SEQ ID NO 79
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Tetrahydroisoquinoline-3-carboxylic
      acid
<220> FEATURE:
<221> NAME/KEY: MISC_FEATURE
<222> LOCATION: (4)..(4)
<223> OTHER INFORMATION: Leucine-daunorubicin

<400> SEQUENCE: 79

Xaa Ile Ala Xaa
    1

<210> SEQ ID NO 80
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-2-Thienylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 80

Xaa Ile Ala Xaa
1

<210> SEQ ID NO 81
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-2-Naphthylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 81

Xaa Ile Ala Xaa
1

<210> SEQ ID NO 82
<211> LENGTH: 4
```

```
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 82

Xaa Ile Ala Xaa
1

<210> SEQ ID NO 83
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-4-(Aminomethyl)benzoic acid
<220> FEATURE:
<221> NAME/KEY: MISC_FEATURE
<222> LOCATION: (4)..(4)
<223> OTHER INFORMATION: Leucine-daunorubicin

<400> SEQUENCE: 83

Xaa Ile Ala
1

<210> SEQ ID NO 84
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 84

Xaa Ile Ala Xaa
1

<210> SEQ ID NO 85
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 85

Xaa Ile Ala Xaa
```

```
<210> SEQ ID NO 86
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-2-Thienylalanine
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 86

Xaa Ile Xaa Xaa
1

<210> SEQ ID NO 87
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-2-Naphthylalanine
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 87

Xaa Ile Xaa Xaa
1

<210> SEQ ID NO 88
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 88

Xaa Ile Xaa Xaa
1

<210> SEQ ID NO 89
```

```
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-4-(Aminomethyl)benzoic acid
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-doxorubicin

<400> SEQUENCE: 89

Xaa Ile Xaa Xaa
1

<210> SEQ ID NO 90
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Aminoisobutyric acid
<220> FEATURE:
<221> NAME/KEY: MISC_FEATURE
<222> LOCATION: (3)..(3)
<223> OTHER INFORMATION: Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 90

Xaa Ile Xaa Xaa
1

<210> SEQ ID NO 91
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Phenylalanine-daunorubicin

<400> SEQUENCE: 91

Xaa Ile Gly Xaa
1

<210> SEQ ID NO 92
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
```

```
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 92

Xaa Ile Gly Xaa
1

<210> SEQ ID NO 93
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Tetrahydroisoquinoline-3-carboxylic
      acid
<220> FEATURE:
<221> NAME/KEY: MISC_FEATURE
<222> LOCATION: (4)..(4)
<223> OTHER INFORMATION: Leucine-daunorubicin

<400> SEQUENCE: 93

Xaa Ile Gly Xaa
1

<210> SEQ ID NO 94
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-2-Thienylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 94

Xaa Ile Gly Xaa
1

<210> SEQ ID NO 95
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-2-Naphthylalanine
<220> FEATURE:
<221> NAME/KEY: MISC_FEATURE
<222> LOCATION: (4)..(4)
<223> OTHER INFORMATION: Leucine-daunorubicin

<400> SEQUENCE: 95

Xaa Ile Gly Xaa
1

<210> SEQ ID NO 96
<211> LENGTH: 4
<212> TYPE: PRT
```

```
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 96

Xaa Ile Gly Xaa
1

<210> SEQ ID NO 97
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-4-(Aminomethyl)benzoic acid
<220> FEATURE:
<221> NAME/KEY: MISC_FEATURE
<222> LOCATION: (4)..(4)
<223> OTHER INFORMATION: Leucine-daunorubicin

<400> SEQUENCE: 97

Xaa Ile Gly Xaa
1

<210> SEQ ID NO 98
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Aminoisobutyric acid
<220> FEATURE:
<221> NAME/KEY: MISC_FEATURE
<222> LOCATION: (4)..(4)
<223> OTHER INFORMATION: Leucine-daunorubicin

<400> SEQUENCE: 98

Xaa Ile Gly Xaa
1

<210> SEQ ID NO 99
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 99

Xaa Ile Thr Xaa
1
```

<210> SEQ ID NO 100
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Isoleucine-daunorubicin

<400> SEQUENCE: 100

Xaa Ile Tyr Xaa
1

<210> SEQ ID NO 101
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Leucine-daunorubicin

<400> SEQUENCE: 101

Xaa Ile Tyr Xaa
1

<210> SEQ ID NO 102
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Beta-Alanine
<220> FEATURE:
<221> NAME/KEY: MISC_FEATURE
<222> LOCATION: (4)..(4)
<223> OTHER INFORMATION: Glycine-doxorubicin

<400> SEQUENCE: 102

Xaa Ile Tyr Xaa
1

<210> SEQ ID NO 103
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Isoleucine
<220> FEATURE:
<221> NAME/KEY: MISC_FEATURE
<222> LOCATION: (3)..(3)
<223> OTHER INFORMATION: Leucine-doxorubicin

```
<400> SEQUENCE: 103

Xaa Ala Xaa
1

<210> SEQ ID NO 104
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: N-methyl-Alanine
<220> FEATURE:
<221> NAME/KEY: MISC_FEATURE
<222> LOCATION: (1)..(1)
<223> OTHER INFORMATION: Succinyl-Isoleucine
<220> FEATURE:
<221> NAME/KEY: MISC_FEATURE
<222> LOCATION: (3)..(3)
<223> OTHER INFORMATION: Leucine-doxorubicin

<400> SEQUENCE: 104

Xaa Xaa Xaa
1

<210> SEQ ID NO 105
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Isoleucine
<220> FEATURE:
<221> NAME/KEY: MISC_FEATURE
<222> LOCATION: (2)..(2)
<223> OTHER INFORMATION: N-methyl-Alanine
<220> FEATURE:
<221> NAME/KEY: MISC_FEATURE
<222> LOCATION: (3)..(3)
<223> OTHER INFORMATION: Leucine-doxorubicin

<400> SEQUENCE: 105

Xaa Xaa Xaa
1

<210> SEQ ID NO 106
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Leucine
<220> FEATURE:
<221> NAME/KEY: MISC_FEATURE
<222> LOCATION: (2)..(2)
<223> OTHER INFORMATION: N-methyl-Alanine
<220> FEATURE:
<221> NAME/KEY: MISC_FEATURE
<222> LOCATION: (3)..(3)
<223> OTHER INFORMATION: Leucine-doxorubicin

<400> SEQUENCE: 106

Xaa Xaa Xaa
```

```
<210> SEQ ID NO 107
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Isoleucine
<220> FEATURE:
<221> NAME/KEY: MISC_FEATURE
<222> LOCATION: (3)..(3)
<223> OTHER INFORMATION: Leucine-doxorubicin

<400> SEQUENCE: 107

Xaa Pro Xaa
1

<210> SEQ ID NO 108
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Succinyl-Leucine
<220> FEATURE:
<221> NAME/KEY: MISC_FEATURE
<222> LOCATION: (3)..(3)
<223> OTHER INFORMATION: Glycine-doxorubicin

<400> SEQUENCE: 108

Xaa Tyr Xaa
1

<210> SEQ ID NO 109
<211> LENGTH: 39
<212> TYPE: DNA
<213> ORGANISM: Artificial sequence
<220> FEATURE:
<223> OTHER INFORMATION: chemically synthesized primer

<400> SEQUENCE: 109
aagcttgccg ccaccatggg caagtcagaa agtcagatg                              39

<210> SEQ ID NO 110
<211> LENGTH: 30
<212> TYPE: DNA
<213> ORGANISM: Artificial sequence
<220> FEATURE:
<223> OTHER INFORMATION: chemically synthesized primer

<400> SEQUENCE: 110
tctagaaggg aggccaagtc gaggttggtc                                        30

<210> SEQ ID NO 111
<211> LENGTH: 30
<212> TYPE: DNA
<213> ORGANISM: Artificial sequence
<220> FEATURE:
<223> OTHER INFORMATION: chemically synthesized primer

<400> SEQUENCE: 111
tctagagatt actatgaatg cactggaatc                                        30
```

```
<210> SEQ ID NO 112
<211> LENGTH: 30
<212> TYPE: DNA
<213> ORGANISM: Artificial sequence
<220> FEATURE:
<223> OTHER INFORMATION: chemically synthesized primer

<400> SEQUENCE: 112
ctcgaggtac tcattattca gtttgttatc                                     30

<210> SEQ ID NO 113
<211> LENGTH: 30
<212> TYPE: DNA
<213> ORGANISM: Artificial sequence
<220> FEATURE:
<223> OTHER INFORMATION: chemically synthesized primer

<400> SEQUENCE: 113
ctcgagttga actacaaaga agatgaatac                                     30

<210> SEQ ID NO 114
<211> LENGTH: 32
<212> TYPE: DNA
<213> ORGANISM: Artificial sequence
<220> FEATURE:
<223> OTHER INFORMATION: chemically synthesized primer

<400> SEQUENCE: 114
ttaattaatc accaaacccg gcacttcttt tc                                  32

<210> SEQ ID NO 115
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 9-Fluorenylmethyloxycarbonyl-Isoleucine

<400> SEQUENCE: 115

Xaa Ala Leu
1

<210> SEQ ID NO 116
<211> LENGTH: 3
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 9-Fluorenylmethyloxycarbonyl-Isoleucine
<220> FEATURE:
<221> NAME/KEY: MISC_FEATURE
<222> LOCATION: (3)..(3)
<223> OTHER INFORMATION: Leucine-doxorubicin

<400> SEQUENCE: 116

Xaa Ala Xaa
1

<210> SEQ ID NO 117
<211> LENGTH: 4
<212> TYPE: PRT
```

```
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 9-Fluorenylmethyloxycarbonyl-Beta-Alanine

<400> SEQUENCE: 117

Xaa Ile Ala Leu
1

<210> SEQ ID NO 118
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 9-Fluorenylmethyloxycarbonyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 118

Xaa Ile Ala Xaa
1

<210> SEQ ID NO 119
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: 9-Fluorenylmethyloxycarbonyl-Beta-Alanine
<220> FEATURE:
<221> NAME/KEY: MISC_FEATURE
<222> LOCATION: (4)..(4)
<223> OTHER INFORMATION: Leucine-OBn

<400> SEQUENCE: 119

Xaa Ile Ala Xaa
1

<210> SEQ ID NO 120
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Methyl-hemisuccinyl-Beta-Alanine
<220> FEATURE:
<221> NAME/KEY: MISC_FEATURE
<222> LOCATION: (4)..(4)
<223> OTHER INFORMATION: Leucine-OBn

<400> SEQUENCE: 120

Xaa Ile Ala Xaa
1

<210> SEQ ID NO 121
<211> LENGTH: 4
```

```
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Methyl-hemisuccinyl-Beta-Alanine

<400> SEQUENCE: 121

Xaa Ile Ala Leu
1

<210> SEQ ID NO 122
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Methyl-hemisuccinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 122

Xaa Ile Ala Xaa
1

<210> SEQ ID NO 123
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Methyl-hemisuccinyl-Beta-Alanine

<400> SEQUENCE: 123

Xaa Leu Ala Leu
1

<210> SEQ ID NO 124
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Methyl-hemisuccinyl-Beta-Alanine
<220> FEATURE:
<221> NAME/KEY: MISC_FEATURE
<222> LOCATION: (4)..(4)
<223> OTHER INFORMATION: Leucine-doxorubicin

<400> SEQUENCE: 124

Xaa Leu Ala Xaa
1

<210> SEQ ID NO 125
<211> LENGTH: 4
<212> TYPE: PRT
<213> ORGANISM: Artificial sequence
<220> FEATURE:
```

-continued

```
<223> OTHER INFORMATION: chemically synthesized
<220> FEATURE:
<221> NAME/KEY: MISC_FEATURE
<222> LOCATION: (1)..(1)
<223> OTHER INFORMATION: Beta-Alanine

<400> SEQUENCE: 125

Xaa Leu Ala Leu
1

<210> SEQ ID NO 126
<211> LENGTH: 4
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Allyl-Succinyl-Beta-Alanine
<220> FEATURE:
<221> NAME/KEY: MISC_FEATURE
<222> LOCATION: (4)..(4)
<223> OTHER INFORMATION: Leucine-Doxorubicin

<400> SEQUENCE: 126

Xaa Ile Ala Xaa
1
```